United States Patent
Caldarelli et al.

(10) Patent No.: US 8,975,267 B2
(45) Date of Patent: Mar. 10, 2015

(54) TRICYCLIC PYRROLO DERIVATIVES, PROCESS FOR THEIR PREPARATION AND THEIR USE AS KINASE INHIBITORS

(75) Inventors: Marina Caldarelli, Milan (IT); Mauro Angiolini, Gavirate (IT); Italo Beria, Nerviano (IT); Maria Gabriella Brasca, Nerviano (IT); Francesco Casuscelli, Dairago (IT); Roberto D'Alessio, Cinisello Balsamo (IT); Andrea Lombardi Borgia, Paullo (IT)

(73) Assignee: Nerviano Medical Sciences S.r.l., Nerviano (MI) (IT)

( * ) Notice: Subject to any disclaimer, the term of this patent is extended or adjusted under 35 U.S.C. 154(b) by 0 days.

(21) Appl. No.: 13/980,168

(22) PCT Filed: Jan. 19, 2012

(86) PCT No.: PCT/EP2012/050773
§ 371 (c)(1),
(2), (4) Date: Jul. 17, 2013

(87) PCT Pub. No.: WO2012/101032
PCT Pub. Date: Aug. 2, 2012

(65) Prior Publication Data
US 2013/0296305 A1 Nov. 7, 2013

(30) Foreign Application Priority Data
Jan. 26, 2011 (EP) ..................................... 11152190

(51) Int. Cl.
A61K 31/519 (2006.01)
C07D 487/04 (2006.01)
A61K 31/55 (2006.01)
A61K 45/06 (2006.01)

(52) U.S. Cl.
CPC ............. *C07D 487/04* (2013.01); *A61K 31/519* (2013.01); *A61K 31/55* (2013.01); *A61K 45/06* (2013.01)
USPC .......................................... 514/267; 544/250

(58) Field of Classification Search
CPC .............................. C07D 487/04; A61K 31/519
USPC .......................................... 514/267; 544/250
See application file for complete search history.

(56) References Cited

U.S. PATENT DOCUMENTS

| 5,750,769 A | 5/1998 | Bowden |
| 2010/0160318 A1 | 6/2010 | Tang et al. |

FOREIGN PATENT DOCUMENTS

| WO | WO2005037843 A1 | 4/2005 | |
| WO | WO 2008/065054 | * 6/2008 | ........... C07D 471/04 |
| WO | WO2008065054 A1 | 6/2008 | |
| WO | WO2009089305 A1 | 7/2009 | |
| WO | WO2009156315 A1 | 12/2009 | |

OTHER PUBLICATIONS

International Search Report dated Mar. 16, 2012 issued in PCT/EP2012/050773.
Amaravadi R. et al., "The Survival Kinases Akt and Pim as Potential Pharmacological Targets", The Journal of Clinical Investigation 115(10):2618-2624 (Oct. 2005).
Arostegui J.L. et al., "A Novel G6PC3 Homozygous 1-BP Deletion as a Cause of Severe Congenital Neutropenia", Blood 114(8):1718-1719 (Aug. 20, 2009).
Bertheau P. et al., "Exquisite Sensitivity of TP53 Mutant and Basal Breast Cancers to a Dose-Dense Epirubicin-Cyclophosphamide Regimen", PLoS Medicine 4(3):0585-0594 (Mar. 2007).
Brannock K.C. et al., "Cycloaddition Reactions of Enamines Derived from Aldehydes and Acyclic Ketones", Enamine Chemistry IV 29:801-812 (Apr. 1964).
Brault L. et al., "PIM Serine/Threonine Kinases in the Pathogenesis and Therapy of Hematologic Malignancies and Solid Cancers", Haematologica 95(6):1004-1015 (2010).
Carter S.L. et al., "A Signature of Chromosomal Instability Inferred from Gene Expression Profiles Predicts Clinical Outcome in Multiple Human Cancers", Nature Genetics 38(9):1043-1048 (Sep. 2006).
Choudhary C. et al., "Mislocalized Activation of Oncogenic RTKs Switches Downstream Signaling Outcomes", Molecular Cell 36:326-339 (Oct. 23, 2009).
Ciufolini M.A. et al., "Practical Synthesis of (+)-Chlorovulone II", J. Org. Chem. 63:1668-1675 (1998).
Cohen A.M. et al., "Increased Expression of the hPim-2 Gene in Human Chronic Lymphocytic Leukemia and Non-Hodgkin Lymphoma", Leukemia & Lymphoma 45(5):951-955 (May 2004).
Cohen P., "The Development and Therapeutic Potential of Protein Kinase Inhibitors", Current Opinion in Chemical Biology 3:459-465 (1999).
Colombo M. et al., "A Fully Automated Method for Accurate Mass Determination Using High-Performance Liquid Chromatography with a Quadrupole/Orthogonal Acceleration Time-of-Flight Mass Spectrometer", Rapid Communications in Mass Spectrometry 18:511-517 (2004).
De Carcer G. et al., "Targeting Cell Cycle Kinases for Cancer Therapy", Current Medicinal Chemistry 14:969-985 (2007).

(Continued)

*Primary Examiner* — Erich A Leeser
(74) *Attorney, Agent, or Firm* — Scully, Scott, Murphy & Presser, P.C.

(57) ABSTRACT

The present invention relates to tricyclic pyrrolo derivatives of Formula (I), which modulate the activity of protein kinases and are therefore useful in treating diseases caused by dysregulated protein kinase activity. The present invention also provides methods for preparing these compounds, pharmaceutical compositions comprising these compounds, and methods of treating diseases utilizing such these compounds or the pharmaceutical compositions containing them.

(I)

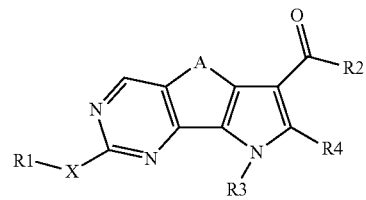

14 Claims, No Drawings

(56) References Cited

OTHER PUBLICATIONS

Huttmann A. et al., "Gene Expression Signatures Separate B-Cell Chronic Lymphocytic Leukaemia Prognostic Subgroups Defined by ZAP-70 and CD38 Expression Status", Leukemia 20:1774-1782 (2006).

Jelluma N. et al., "Chromosomal Instability by Inefficient Mps1 Auto-Activation Due to a Weakened Mitotic Checkpoint and Lagging Chromosomes", PLoS One 3(6):1-8 (Jun. 2008).

Jelluma N. et al., "Mps1 Phosphorylates Borealin to Control Aurora B Activity and Chromosome Alignment", Cell 132:233-246 (Jan. 25, 2008).

Jones M.H. et al., "Chemical Genetics Reveals a Role for Mps1 Kinase in Kinetochore Attachment During Mitosis", Current Biology 15:160-165 (Jan. 26, 2005).

Kim K-T et al., "Pim-1 is Up-Regulated by Constitutively Activated FLT3 and Plays a Role in FLT3-Mediated Cell Survival", Blood 105(4):1759-1767 (Feb. 15, 2005).

Kops G.J.P.L. et al., "On the Road to Cancer: Aneuploidy and the Mitotic Checkpoint", Nature Reviews—Cancer 5:773-785 (Oct. 2005).

Kumar A. et al., "Crystal Structures of Proto-Oncogene Kinase Pim1: A Target of Aberrant Somatic Hypermutations in Diffuse Large Cell Lymphoma", J. Mol. Biol. 348:183-193 (2005).

Musacchio A. et al., "The Spindle-Assembly Checkpoint in Space and Time", Nature Reviews—Molecular Cell Biology 8:379-393 (May 2007).

Rosillo M. et al., "Combination of RCM and the Pauson-Khand Reaction: One-Step Synthesis of Tricyclic Structures", Eur. J. Org. Chem. 23:3917-3927 (2008).

Schmidt M. et al., "Ablation of the Spindle Assembly Checkpoint by a Compound Targeting Mps1", EMBO reports 6(9):866-872 (2005).

Shah N. et al., "Potential Roles for the PIM1 Kinase in Human Cancer—A Molecular and Therapeutic Appraisal", European Journal of Cancer 44:2144-2151 (2008).

Stucke V.M. et al., "Human Mps1 Kinase is Required for the Spindle Assembly Checkpoint but not for Centrosome Duplication", The EMBO Journal 21(7):1723-1732 (2002).

Tighe A. et al., "Mps1 Kinase Activity Restrains Anaphase During an Unperturbed Mitosis and Targets Mad2 to Kinetochores", J. Cell Biol. 181(6):893-901 (2008).

Velculescu V.E., "Defining the Blueprint of the Cancer Genome", Carcinogenesis 29(6):1087-1091 (2008).

Weaver B.A.A. et al., "Aneuploidy Acts Both Oncogenically and as a Tumor Suppressor", Cancer Cell 11:25-36 (Jan. 2007).

Weiss E. et al., "The Saccharomyces Cerevisiae Spindle Pole Body Duplication Gene MPS1 is Part of a Mitotic Checkpoint", The Journal of Cell Biology 132(1-2):111-123 (Jan. 1996).

Winey M. et al., "MPS1 and MPS2: Novel Yeast Genes Defining Distinct Steps of Spindle Pole Body Duplication", The Journal of Cell Biology 114(4):745-754 (Aug. 1991).

Yuan B. et al., "Increased Expression of Mitotic Checkpoint Genes in Breast Cancer Cells with Chromosomal Instability", Clin Cancer Res 12(2):405-410 (Jan. 15, 2006).

* cited by examiner

TRICYCLIC PYRROLO DERIVATIVES, PROCESS FOR THEIR PREPARATION AND THEIR USE AS KINASE INHIBITORS

The present invention relates to tricyclic pyrrolo derivatives, to a process for their preparation, to pharmaceutical compositions comprising them, and to their use as therapeutic agents, particularly in the treatment of cancer and cell proliferation disorders.

The compounds of this invention are therefore useful in treating diseases caused by dysregulated protein kinase activity. The present invention also provides methods for preparing these compounds, pharmaceutical compositions comprising these compounds, and methods of treating diseases utilizing pharmaceutical compositions comprising these compounds.

The malfunctioning of protein kinases (PKs) is the hallmark of numerous diseases. A large share of the oncogenes and proto-oncogenes involved in human cancers encode for PKs. The enhanced activities of PKs are also implicated in many non-malignant diseases, such as benign prostate hyperplasia, familial adenomatosis, polyposis, neuro-fibromatosis, psoriasis, vascular smooth cell proliferation associated with atherosclerosis, pulmonary fibrosis, arthritis glomerulonephritis and post-surgical stenosis and restenosis.

PKs are also implicated in inflammatory conditions and in the multiplication of viruses and parasites. PKs may also play a major role in the pathogenesis and development of neurodegenerative disorders.

For a general reference to PKs malfunctioning or deregulation see, for instance, Current Opinion in Chemical Biology 1999, 3, 459-465 and Carcinogenesis 2008, 29, 1087-1091.

The use of mitotic inhibitors in cancer therapy is a widely accepted clinical strategy for the treatment of a broad range of human cancers. Taxanes (Paclitaxel and Docetaxel) and Vinca Alkaloids (Vincristine and Vinblastine) work by either stabilizing or destabilizing microtubules with catastrophic consequences in cells progressing through mitosis. They are first line therapeutics for several tumour types and second line in cisplatin-refractory ovarian, breast, lung, bladder and esophagus cancers (Taxanes). However, due to the role of microtubules in processes such as cell movement, phagocytosis and axonal transport certain toxicities such as peripheral neuropathy are frequently observed with these agents. Progression through mitosis is a requirement of all proliferating cells and hence cancer therapies that have targets in mitosis are generally applicable to a wide range of tumour types.

Several protein kinases play key roles in the orchestration of the cell cycle and some of them are already subject to targeted therapies in the oncology setting including Cdk-2 and Aurora-A. The fidelity of mitosis is of paramount importance and several "checkpoints" exist in normal cells to maintain chromosome integrity during the cell cycle.

The Spindle Assembly Checkpoint (SAC) is specifically required for proper chromosomal segregation into the two daughter cells upon cellular division. It ensures that sister chromatids aligned at the metaphase plate do not separate prior to the bipolar attachment of all duplicated chromosomes to the mitotic spindle (Reviewed in Musacchio A. and Salmon D. Nat Rev Mol Cell Biol, May; 8(5): 379-93, 2007).

Even a single un-aligned chromosome is sufficient to trigger the SAC signal, it is a tightly regulated pathway that ultimately results into the inhibition of the anaphase promoting complex/cyclosome (APC/C)-mediated polyubiquitylation and degradation of two key mitotic components: cyclin B1 and Securin. Securin specifically is required to get sister chromatids separation and anaphase transition, instead cyclin B1 inactivates the master mitotic kinase CDK1 promoting mitotic exit. (Reviewed in Musacchio A. and Salmon D. Nat Rev Mol Cell Biol, May; 8(5): 379-93, 2007).

A large group of proteins has been already identified to play a role in SAC functions: human MPS1 (monopolar spindle 1) kinase, (also known as TTK) has certainly a major role. MPS1 is a dual Tyrosine and Serine/Threonine kinase highly conserved from yeast to mammals. The human genome encodes for just one MPS1 gene family member, which does not have high sequence similarities with other protein kinases.

MPS1 is a cell cycle regulate enzyme that is upregulated and activated in mitosis upon phosphorylation (Stucke V M, et al., Embo J. 21 (7): 1723, 2002).

In *Saccharomyces cerevisiae*, MPS1 controls spindle-pole body duplication (Winey M. et al., J. Cell Biol 114:745, 1991), spindle assembly (Jones, M. H. et al., Curr. Biol. 15: 160, 2005) and the spindle assembly checkpoint (Weiss and Winey, J. Cell. Biol 132:111, 1996). Instead in higher eukaryotes the MPS1 kinase activity is mainly involved in SAC regulation and functions (Jelluma, N. et al., Cell 132: 233, 2008).

RNA interference experiments indicate that in the absence of MPS1 the SAC functions are compromised: mitotic length is reduced and cells divide rapidly without methaphase plate alignment, which ultimately causes aberrant aneuploidization, mitotic catastrophe and is not anymore compatible with cellular survival (Jelluma N. et al., Cell 132: 233, 2008; Tighe A. et al., J Cell Biol 2008; Jelluma N. et al., Plos ONE 3 (6): e2415, 2008). Moreover, to support these results, a small molecule ATP-competitor MPS1 inhibitor was described and despite its not clean selectivity profile, it was shown to be capable to inactivate SAC functions, inactivate nocodazole and taxol mediated mitotic arrest and promote cell death mainly in tumorigenic cell lines (Schmidt et al., EMBO Rep, 6(9): 866, 2005).

Despite that most of the tumors are aneuploid, MPS1 was never found to be mutated in cancer, instead, it has been found upregulated in a number of tumors of different origins like bladder, anaplastic thyroid, breast and prostate cancer (Yuan B. et al, Clin Cancer Res, 12(4): 1121, 2006). Moreover was found in the signature of the top 25 genes over-expressed in CIN and aneuploid tumors which predict clinical outcome in breast and lung cancer, medulloblastoma, glioma, mesothelioma and lymphoma (Carter S L et al., Nat Genet. 38 (9): 1043, 2006). Finally is highly elevated in metastatic tumors and was found to be over-expressed in p53 mutated breast cancers (Bertheau P. et al., Plos Med 4(3):e90, 2007).

Together with the fact that also other SAC components like MAD2, BUBR1 or BUB1 have been found up-regulated in different tumors (deCarcer G. et al., Curr Med Chem 14(9): 969, 2007), it looks that SAC functions could be required and essential to keep tumoral highly aneuploidy cells capable to segregate and tumoral selectivity of SAC inhibitors is foreseen in particular for highly aneuploid tumors like colon, lung and breast carcinomas (Kops G. J. et al., Nat. Rev Cancer, 5:773, 2005).

Finally, massive aneuploidy induction and SAC deregulation have been shown to reduce tumorigenesis in tumour prone mice sustaining the hypothesis that SAC inhibition could confer tumour growth inhibition (Weaver et al., Cancer Cell 11(1): 25, 2007). Thus, for these reasons, pharmacological attenuation of MPS1 function may have a therapeutic benefit in the treatment of several diverse cancers.

Originally identified as activated genes by proviral mutagenesis in a lymphoma mouse model, PIMs (PIM1, PIM2 and/or PIM-3 throughout this application) are protein-serine/threonine kinases. PIM kinases are poorly expressed in normal tissues, and overexpressed or even mutated in a discrete number of human cancers, including Lymphoma, Leukaemia, Prostate, Pancreas and Gastric cancers [Shah et al. *Eur. J. Cancer*, 44, 2144-51, (2008)].

PIM kinases are constitutively active and their activity supports in vitro and in vivo tumor cell growth and survival through modification of an increasing number of common as well as isoform-specific substrates including several cell cycle regulators and apoptosis mediators. PIM1 but not PIM2 seems also to mediate homing and migration of normal and malignant hematopoietic cells by regulating chemokine receptor surface expression [Brault et al. *Haematologica* 95 1004-1015 (2010)].

There is increasing evidence that PIM1 and PIM2 kinases may be involved in mediating the oncogenic effects of some acute myelogenous leukemias (AML)-associated oncogenes. In particular, the oncogenic role of FLT3-mutations (ITD and KD mut., present in 30% of AMLs) and/or translocations involving the MLL gene (occurring in 20% of AMLs), [Kumar, et al. *J. Mol. Biol.* 348, 183-193, (2005)]. PIM1 is more expressed in FLT3-ITD-transformed AML cells than in WT bone marrow cells. Data suggest that PIM1 as well as PIM2 inhibition may mediate FLT3ITD-dependent death of AML cells. Interestingly, cells transformed by FLT3 mutations that confer resistance to small-molecule tyrosine kinase inhibitors were still sensitive to knockdown of PIM2, or PIM-1 and PIM-2 by RNAi, [Kim et al., *Blood* 105, 1759-67, (2005)].

Moreover, PIM2 has been reported being over-expressed and associated with progression of several malignancies that originate from the B-cell lineage such as chronic lymphocytic (CLL), diffuse large B-cell lymphoma (DLBCL), mantle cell lymphoma (MCL) or myeloma [Cohen et al., *Leukemia & Lymphoma* 45(5) 951-955 (2004), Huttmann et al. *Leukemia* 20 1774 (2006)].

Interestingly, PIM and AKT/PKB seem to play partly redundant roles in mediating growth and survival of hematopoietic cells most probably due to overlapping substrates like BAD, p21$^{WAF1/CIP1}$, p27$^{KIP1}$, or Cot/Tpl-2 [Choudhary et al., *Mol Cell.* 36 326-39 (2009)].

PIM kinases have been shown to control mTOR inhibition (rapamycin) resistant, proliferation and survival. Therefore, a combination of small molecule inhibitors targeting several survival kinases might be essential for a powerful cancer therapeutic platform [Amaravadi R., et al. J. Clin. Invest. 2005, 115 (10) 2618-24]. Oncogenic protein synthesis through eIF4E binding protein 1 (4E-BP1) seems to be mTOR-independent and controlled by PIM-2. This observations suggest that the oncogenic eIF4F translation-initiating complex could be blocked with small molecules PIM-2 inhibitors [Tamburini J. et al. Blood 2009, 114 (8), 1718-27 and Brault L. et al. Haematologica 2010, 95 (6) 1004-1015].

Tetrahydrobenzocycloheptene derivatives known in the art as immunosuppressive agents and for treating and preventing inflammatory conditions, allergic disorders and immune disorders are disclosed in WO2009/089305.

Tetrahydrocycloheptapyrimidine derivatives known in the art as protein kinase inhibitors are disclosed in WO2005/037843.

Tricyclicindole derivatives possessing kinase inhibitory activity have been disclosed in WO2008/065054, in the name of the applicant itself; some specific compounds of the aforementioned WO2008/065054 are excluded from the present general formula.

Despite these developments, there is still need for effective agents for said diseases.

The present inventors have now discovered that compounds of the formula (I), described below, are kinase inhibitors and are thus useful in therapy as antitumor agents and lack, in terms of both toxicity and side effects, the aforementioned drawbacks associated with currently available antitumor drugs.

Accordingly, a first object of the present invention is to provide a substituted tricyclic compound of the formula (I)

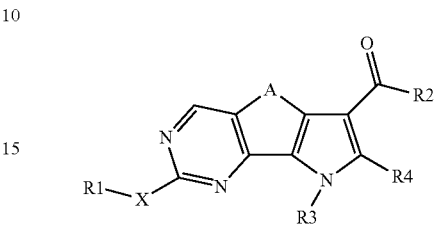

wherein
R1 is hydrogen, halogen or an optionally substituted group selected from amino, straight or branched $C_1$-$C_6$ alkyl, $C_3$-$C_7$ cycloalkyl, cycloalkyl-alkyl, aryl, arylalkyl, heterocyclyl and heterocyclylalkyl;
R2 is a group selected from —NR"R'", —N(OR'")R" and OR", wherein R" and R'" are, each independently, hydrogen or an optionally substituted group selected from straight or branched $C_1$-$C_6$ alkyl, $C_3$-$C_7$ cycloalkyl, cycloalkyl-alkyl, aryl, arylalkyl, heterocyclyl and heterocyclylalkyl or, together with the nitrogen atom to which they are bonded, R" and R'" may form a 5 to 6 membered heteroaryl or heterocyclyl group, optionally containing one additional heteroatom selected among N, O and S;
R3 is hydrogen or optionally substituted group selected from straight or branched $C_1$-$C_6$ alkyl, $C_3$-$C_7$ cycloalkyl, cycloalkyl-alkyl, aryl, arylalkyl, heterocyclyl and heterocyclylalkyl;
R4 is hydrogen or an optionally substituted group selected from straight or branched $C_1$-$C_6$ alkyl, $C_3$-$C_7$ cycloalkyl, cycloalkyl-alkyl, aryl, arylalkyl, heterocyclyl and heterocyclylalkyl;
X is a single bond or a divalent radical selected from —NR'—, —CONR'—, —NH—CO—NH—, —O—, —S—, —SO$_2$— and —OSO$_2$—, wherein R' is hydrogen or an optionally substituted group selected from straight or branched $C_1$-$C_6$ alkyl, $C_3$-$C_7$ cycloalkyl, cycloalkyl-alkyl, aryl, arylalkyl, heterocyclyl and heterocyclylalkyl or, together with the nitrogen atom to which they are bound, R1 and R' may form a 5 to 6 membered heteroaryl or heterocyclyl group optionally containing one additional heteroatom selected from N, O and S;
A is a group selected from —CH$_2$—, —(CH$_2$)$_2$—, —(CH$_2$)$_3$—, —CH═CH—, —C(CH$_3$)$_2$—CH$_2$— and —CH$_2$—C(CH$_3$)$_2$;
or a pharmaceutically acceptable salt thereof,
with the proviso that the following compounds are excluded:
ethyl 2-amino-9-methyl-6,9-dihydro-5H-pyrrolo[3,2-h]quinazoline-7-carboxylate,
2-amino-9-methyl-6,9-dihydro-5H-pyrrolo[3,2-h]quinazoline-7-carboxylic acid,
2-amino-9-methyl-6,9-dihydro-5H-pyrrolo[3,2-h]quinazoline-7-carboxamide, ethyl 2-amino-8-phenyl-9H-pyrrolo[3,2-h]quinazoline-7-carboxylate,
2-amino-8-phenyl-9H-pyrrolo[3,2-h]quinazoline-7-carboxamide,
2-amino-9-methyl-8-phenyl-9H-pyrrolo[3,2-h]quinazoline-7-carboxamide and 2-amino-9-methyl-8-phenyl-6,9-dihydro-5H-pyrrolo[3,2-h]quinazoline-7-carboxamide.

The present invention also provides methods of synthesizing the substituted tricyclic, represented by the formula (I), prepared through a process consisting of standard synthetic transformations and isomers, tautomers, hydrates, solvates, complexes, metabolites, prodrugs, carriers, N— oxides.

The present invention also provides a method for treating diseases caused by and/or associated with dysregulated protein kinase activity, particularly ABL, ACK1, AKT1, ALK, AUR1, AUR2, BRK, BUB1, CDC7/DBF4, CDK2/CYCA, CHK1, CK2, EEF2K, EGFR1, EphA2, EphB4, ERK2, FAK, FGFR1, FLT3, GSK3beta, Haspin, IGFR1, IKK2, IR, JAK1, JAK2, JAK3, KIT, LCK, LYN, MAPKAPK2, MELK, MET, MNK2, MPS1, MST4, NEK6, NIM1, P38alpha, PAK4, PDGFR, PDK1, PERK, PIM1, PIM2, PIM3, PKAalpha, PKCbeta, PLK1, RET, ROS1, SULU1, Syk, TLK2, TRKA, TYK, VEGFR2, VEGFR3, ZAP70, more particularly MPS1, PIM1, PIM2, PIM3.

A preferred method of the present invention is to treat a disease caused by and/or associated with dysregulated protein kinase activity selected from the group consisting of cancer, cell proliferative disorders, viral infections, autoimmune and neurodegenerative disorders.

Another preferred method of the present invention is to treat specific types of cancer including but not limited to: carcinoma such as bladder, breast, colon, kidney, liver, lung, including small cell lung cancer, esophagus, gall-bladder, ovary, pancreas, stomach, cervix, thyroid, prostate, and skin, including squamous cell carcinoma; hematopoietic tumors of lymphoid lineage including leukaemia, acute lymphocitic leukaemia, acute lymphoblastic leukaemia, B-cell lymphoma, T-cell-lymphoma, Hodgkin's lymphoma, non-Hodgkin's lymphoma, hairy cell lymphoma and Burkett's lymphoma; hematopoietic tumors of myeloid lineage, including acute and chronic myelogenous leukemias, myelodysplastic syndrome and promyelocytic leukaemia; tumors of mesenchymal origin, including fibrosarcoma and rhabdomyosarcoma; tumors of the central and peripheral nervous system, including astrocytoma neuroblastoma, glioma and schwannomas; other tumors, including melanoma, seminoma, teratocarcinoma, osteosarcoma, xeroderma pigmentosum, keratoxanthoma, thyroid follicular cancer, Kaposi's sarcoma and mesothelioma, highly aneuploid tumors and tumors which do overexpress mitotic checkpoint.

Another preferred method of the present invention is to treat specific cellular proliferation disorders such as, for example, benign prostate hyperplasia, familial adenomatosis polyposis, neurofibromatosis, psoriasis, vascular smooth cell proliferation associated with atherosclerosis, pulmonary fibrosis, arthritis, glomerulonephritis and post-surgical stenosis and restenosis.

Another preferred method of the present invention is to treat immune cell-associated diseases and disorders, such as inflammatory and autoimmune diseases, for examples multiple sclerosis, systemic lupus erythematosis, inflammatory bowel diseases (IBD), Crohn's disease, irritable bowel syndrome, pancreatitis, ulcerative colitis, diverticulosis, myasthenia gravis, vasculitis, psoriasis, scleroderma, asthma, allergy, systemic sclerosis, vitiligo, arthritis such as osteoarthritis, juvenile rheumatoid arthritis, ankylosing spondylitis.

Another preferred method of the present invention is to treat viral infections, in particular the prevention of AIDS development in HIV-infected individuals.

Another preferred method of the present invention is to treat neurodegenerative disorders, such as Alzheimer's disease, Parkinson's disease and Huntington's disease.

In addition, the method of the present invention also provides tumor angiogenesis and metastasis inhibition as well as the treatment of organ transplant rejection and host versus graft disease.

The present invention also provides a pharmaceutical composition comprising one or more compounds of the formula (I) or a pharmaceutically acceptable salt thereof and a pharmaceutically acceptable excipient, carrier and/or diluent.

The present invention further provides a pharmaceutical composition comprising a compound of the formula (I) in combination with known anticancer treatments such as radiation therapy or chemotherapy regimen in combination with cytostatic or cytotoxic agents, antibiotic-type agents, alkylating agents, antimetabolite agents, hormonal agents, immunological agents, interferon-type agents, cyclooxygenase inhibitors (e.g. COX-2 inhibitors), matrixmetalloprotease inhibitors, telomerase inhibitors, tyrosine kinase inhibitors, anti-growth factor receptor agents, anti-HER agents, anti-EGFR agents, anti-angiogenesis agents (e.g. angiogenesis inhibitors), farnesyl transferase inhibitors, ras-raf signal transduction pathway inhibitors, cell cycle inhibitors, other cdks inhibitors, tubulin binding agents, topoisomerase I inhibitors, topoisomerase II inhibitors, and the like.

The present invention further provides an in vitro method for inhibiting protein kinase activity which comprises contacting the kinase with an effective amount of a compound of formula (I) as defined above.

Additionally, the invention provides a product or kit comprising a compound of formula (I) or a pharmaceutically acceptable salt thereof, as defined above, or pharmaceutical compositions thereof and one or more chemotherapeutic agents, as a combined preparation for simultaneous, separate or sequential use in anticancer therapy.

In another aspect the invention provides a compound of formula (I) or a pharmaceutically acceptable salt thereof, as defined above, for use as a medicament.

Moreover the invention provides the use of a compound of formula (I) or a pharmaceutically acceptable salt thereof, as defined above, in the manufacture of a medicament with anticancer activity.

Finally, the invention provides a compound of formula (I) or a pharmaceutically acceptable salt thereof, as defined above, for use in a method of treating cancer.

Unless otherwise specified, when referring to the compounds of the formula (I) per se as well as to any pharmaceutical composition thereof or to any therapeutic treatment comprising them, the present invention includes all of the hydrates, solvates, complexes, metabolites, prodrugs, carriers, N-oxides and pharmaceutically acceptable salts of the compounds of this invention.

In other words, if easily obtainable from the compounds of the formula (I) as defined above, also their isomers, tautomers, hydrates, solvates, complexes, metabolites, prodrugs, carriers and N— oxides are object of the present invention.

A metabolite of a compound of the formula (I) is any compound into which this same compound of the formula (I) is converted in vivo, for instance upon administration to a mammal in need thereof. Typically, without however representing a limiting example, upon administration of a compound of the formula (I), this same derivative may be converted into a variety of compounds, for instance including more soluble derivatives like hydroxylated derivatives, which are easily excreted. Hence, depending upon the metabolic pathway thus occurring, any of these hydroxylated derivatives may be regarded as a metabolite of the compounds of the formula (I).

Prodrugs are any covalently bonded compounds, which release in vivo the active parent drug according to the formula (I).

N-oxides are compounds of the formula (I) wherein nitrogen and oxygen are tethered through a dative bond.

If a stereogenic center or another form of an isomeric center is present in a compound of the present invention, all forms of such isomer or isomers, including enantiomers and diastereomers, are intended to be covered herein. Compounds containing a stereogenic center may be used as a racemic mixture, an enantiomerically enriched mixture, or the racemic mixture may be separated using well-known techniques and an individual enantiomer may be used alone. In cases in which compounds have unsaturated carbon-carbon double bonds, both the cis (Z) and trans (E) isomers are within the scope of this invention.

In cases wherein compounds may exist in tautomeric forms, such as keto-enol tautomers, each tautomeric form is contemplated as being included within this invention whether existing in equilibrium or predominantly in one form.

The term "aryl" includes carbocyclic or heterocyclic hydrocarbons with from 1 to 2 ring moieties, either fused or linked to each other by single bonds, wherein at least one of the rings is aromatic; if present, any aromatic heterocyclic hydrocarbon also referred to as heteroaryl group, comprises a 5 to 6 membered ring with from 1 to 3 heteroatoms selected from N, O and S.

Examples of aryl groups according to the invention are, for instance, phenyl, biphenyl, α- or β-naphthyl, dihydronaphthyl, thienyl, benzothienyl, furyl, benzofuranyl, pyrrolyl, imidazolyl, pyrazolyl, thiazolyl, isothiazolyl, oxazolyl, isoxazolyl, pyridyl, pyrazinyl, pyrimidinyl, pyridazinyl, indolyl, isoindolyl, purinyl, quinolyl, isoquinolyl, dihydroquinolinyl, quinoxalinyl, benzodioxolyl, indanyl, indenyl, triazolyl, and the like.

With the term "heterocyclyl" (also known as "heterocycloalkyl") we intend a 3- to 7-membered, saturated or partially unsaturated carbocyclic ring where one or more carbon atoms are replaced by heteroatoms such as nitrogen, oxygen and sulfur. Non limiting examples of heterocyclyl groups are, for instance, pyrane, pyrrolidine, pyrroline, imidazoline, imidazolidine, pyrazolidine, pyrazoline, thiazoline, thiazolidine, dihydrofuran, tetrahydrofuran, 1,3-dioxolane, piperidine, piperazine, morpholine and the like.

With the term "$C_3$-$C_7$ cycloalkyl", we intend, unless otherwise provided, 3- to 7-membered all-carbon monocyclic ring, which may contain one or more double bonds but does not have a completely conjugated π-electron system. Examples of cycloalkyl groups, without limitation, are cyclopropane, cyclobutane, cyclopentane, cyclopentene, cyclohexane, cyclohexene, cyclohexadiene, cycloeptane, cycloeptene, cycloeptadiene.

With the term "straight or branched $C_1$-$C_6$ alkyl", hence comprehensive of $C_1$-$C_4$ alkyl, we intend any of the groups such as, for instance, methyl, ethyl, n-propyl, isopropyl, n-butyl, isobutyl, tert-butyl, sec-butyl, n-pentyl, n-hexyl, and the like.

With the term "straight or branched $C_2$-$C_6$ alkenyl" we intend any of the groups such as, for instance, vinyl, allyl, 1-propenyl, isopropenyl, 1-butenyl, 2-butenyl, 3-butenyl, 2-pentenyl, 1-hexenyl, and the like.

With the term "straight or branched $C_2$-$C_6$ alkynyl" we intend any of the groups such as, for instance, ethynyl, 2-propynyl, 4-pentynyl, and the like.

According to the present invention and unless otherwise provided, any of the above R1, R2, R3, R4, R', R" and R'" group may be optionally substituted, in any of their free positions, by one or more groups, for instance 1 to 6 groups, independently selected from: halogen atom, nitro, oxo groups (=O), cyano, $C_1$-$C_6$ alkyl, polyfluorinated alkyl, polyfluorinated alkoxy, alkenyl, alkynyl, hydroxyalkyl, aryl, arylalkyl, heterocyclyl, $C_3$-$C_7$ cycloalkyl, hydroxy, alkoxy, aryloxy, heterocyclyloxy, methylenedioxy, alkylcarbonyloxy, arylcarbonyloxy, cycloalkenyloxy, heterocyclylcarbonyloxy, alkylideneaminooxy, carboxy, alkoxycarbonyl, aryloxycarbonyl, cycloalkyloxycarbonyl, heterocyclyloxycarbonyl, amino, ureido, alkylamino, dialkylamino, arylamino, diarylamino, heterocyclylamino, formylamino, alkylcarbonylamino, arylcarbonylamino, heterocyclylcarbonylamino, aminocarbonyl, alkylaminocarbonyl, dialkylaminocarbonyl, arylaminocarbonyl, heterocyclylaminocarbonyl, alkoxycarbonylamino, hydroxyaminocarbonyl, alkoxyimino, alkylsulfonylamino, arylsulfonylamino, heterocyclylsulfonylamino, formyl, alkylcarbonyl, arylcarbonyl, cycloalkylcarbonyl, heterocyclylcarbonyl, alkylsulfonyl, arylsulfonyl, aminosulfonyl, alkylaminosulfonyl, dialkylaminosulfonyl, arylaminosulfonyl, heterocyclylaminosulfonyl, arylthio, alkylthio, phosphonate and alkylphosphonate.

In their turn, whenever appropriate, each of the above substituent may be further substituted by one or more of the aforementioned groups.

In this respect, with the term "halogen atom" we intend a fluorine, chlorine, bromine or iodine atom.

With the term "cyano" we intend a —CN residue.

With the term "nitro" we intend a —NO$_2$ group.

With the term "alkenyl" or "alkynyl" we intend any of the aforementioned straight or branched $C_2$-$C_6$ alkyl groups further bearing a double or triple bond. Non limiting examples of alkenyl or alkynyl groups of the invention are, for instance, vinyl, allyl, 1-propenyl, isopropenyl, 1-butenyl, 2-butenyl, 3-butenyl, 2-pentenyl, 1-hexenyl, ethynyl, 2-propynyl, 4-pentynyl, and the like.

With the term "polyfluorinated alkyl or alkoxy" we intend any of the above straight or branched $C_1$-$C_6$ alkyl or alkoxy groups which are substituted by more than one fluorine atom such as, for instance, trifluoromethyl, trifluoroethyl, 1,1,1,3,3,3-hexafluoropropyl, trifluoromethoxy and the like.

With the term "alkoxy", "aryloxy", "heterocyclyloxy" and derivatives thereof we intend any of the above $C_1$-$C_6$ alkyl, aryl or heterocyclyl groups linked to the rest of the molecule through an oxygen atom (—O—).

From all of the above, it is clear to the skilled person that any group which name is a composite name such as, for instance, arylamino has to be intended as conventionally construed by the parts from which it derives, e.g. by an amino group which is further substituted by aryl, wherein aryl is as above defined.

Likewise, any of the terms such as, for instance, alkylthio, alkylamino, dialkylamino, alkoxycarbonyl, alkoxycarbonylamino, heterocyclylcarbonyl, heterocyclylcarbonylamino, cycloalkyloxycarbonyl and the like, include groups wherein the alkyl, alkoxy, aryl, $C_3$-$C_7$ cycloalkyl and heterocyclyl moieties are as above defined.

Pharmaceutically acceptable salts of the compounds of the formula (I) include the acid addition salts with inorganic or organic acids, e.g., nitric, hydrochloric, hydrobromic, sulfuric, perchloric, phosphoric, acetic, trifluoroacetic, propionic, glycolic, fumaric, lactic, oxalic, malonic, malic, maleic, tartaric, citric, benzoic, cinnamic, mandelic, methanesulphonic, isethionic and salicylic acid. Preferably, the acid addition salt of the compounds of the invention is selected between the hydrochloride or mesylate salt.

Pharmaceutically acceptable salts of the compounds of the formula (I) also include the salts with inorganic or organic bases, e.g., alkali or alkaline-earth metals, especially sodium, potassium, calcium ammonium or magnesium hydroxides, carbonates or bicarbonates, acyclic or cyclic amines, preferably methylamine, ethylamine, diethylamine, triethylamine, piperidine and the like.

Preferred compounds of the formula (I) are the compounds wherein X is a group —NR'— and R2 is a group selected from —NHR" and —N(OR''')R", wherein R" is hydrogen or an optionally substituted group selected from straight or branched $C_1$-$C_6$ alkyl, $C_3$-$C_7$ cycloalkyl, cycloalkyl-alkyl, aryl, arylalkyl, heterocyclyl and heterocyclylalkyl; and R', R''', R1, R3, R4 and A are as above defined.

Other preferred compounds are the compounds of formula (I) wherein X is a group —O— and R2 is a group selected from —NHR" and —N(OR''')R", wherein R" is hydrogen or an optionally substituted group selected from straight or branched $C_1$-$C_6$ alkyl, $C_3$-$C_7$ cycloalkyl, cycloalkyl-alkyl, aryl, arylalkyl, heterocyclyl and heterocyclylalkyl; and R''', R1, R3, R4 and A are as above defined.

Other preferred compounds are the compounds of formula (I) wherein X is a group —S— and R2 is a group selected from —NHR" and —N(OR''')R", wherein R" is hydrogen or an optionally substituted group selected from straight or branched $C_1$-$C_6$ alkyl, $C_3$-$C_7$ cycloalkyl, cycloalkyl-alkyl, aryl, arylalkyl, heterocyclyl and heterocyclylalkyl; and R''', R1, R3, R4 and A are as above defined.

Other preferred compounds are the compounds of formula (I) wherein X is a single bond and R2 is a group selected from —NHR" and —N(OR''')R", wherein R" is hydrogen or an optionally substituted group selected from straight or branched $C_1$-$C_6$ alkyl, $C_3$-$C_7$ cycloalkyl, cycloalkyl-alkyl, aryl, arylalkyl, heterocyclyl and heterocyclylalkyl; and R''', R1, R3, R4 and A are as above defined.

Other preferred compounds are the compounds of formula (I) wherein X is a group —NR'—; R2 is a group —NHR" or —N(OR''')R", wherein R" is hydrogen or an optionally substituted group selected from straight or branched $C_1$-$C_4$ alkyl group and aryl; and R1 is an optionally substituted group selected from straight or branched $C_1$-$C_6$ alkyl, $C_3$-$C_7$ cycloalkyl, cycloalkyl-alkyl, aryl, arylalkyl, heterocyclyl and heterocyclylalkyl; and R', R''', R3, R4 and A are as above defined.

Other preferred compounds are the compounds of formula (I) wherein X is a group —O—; R2 is a group —NHR" or —N(OR''')R", wherein R" is hydrogen or an optionally substituted group selected from straight or branched $C_1$-$C_4$ alkyl group and aryl; and R1 is an optionally substituted group selected from straight or branched $C_1$-$C_6$ alkyl, $C_3$-$C_7$ cycloalkyl, cycloalkyl-alkyl, aryl, arylalkyl, heterocyclyl and heterocyclylalkyl; and R''', R3, R4 and A are as above defined.

Other preferred compounds are the compounds of formula (I) wherein X is a group —S—; R2 is a group —NHR" or —N(OR''')R", wherein R" is hydrogen or an optionally substituted group selected from straight or branched $C_1$-$C_4$ alkyl group and aryl; and R1 is an optionally substituted group selected from straight or branched $C_1$-$C_6$ alkyl, $C_3$-$C_7$ cycloalkyl, cycloalkyl-alkyl, aryl, arylalkyl, heterocyclyl and heterocyclylalkyl; and R', R3, R4 and A are as above defined.

Other preferred compounds are the compounds of formula (I) wherein X is a single bond; R2 is a group —NHR" or —N(OR''')R", wherein R" is hydrogen or an optionally substituted group selected from straight or branched $C_1$-$C_4$ alkyl group and aryl; and R1 is an optionally substituted group selected from straight or branched $C_1$-$C_6$ alkyl, $C_3$-$C_7$ cycloalkyl, cycloalkyl-alkyl, aryl, arylalkyl, heterocyclyl and heterocyclylalkyl; and R''', R3, R4 and A are as above defined.

Preferred specific compounds of the formula (I) or a salt thereof are the compounds listed below:

1) N-(2,6-diethylphenyl)-9-(methoxymethyl)-2-{[2-methoxy-4-(4-methylpiperazin-1-yl)phenyl]amino}-8-methyl-6,9-dihydro-5H-pyrrolo[3,2-h]quinazoline-7-carboxamide,
2) 2-[(4-bromo-2-methoxyphenyl)amino]-N-(2,6-diethylphenyl)-8,9-dimethyl-6,9-dihydro-5H-pyrrolo[3,2-h]quinazoline-7-carboxamide,
3) N-(2,6-diethylphenyl)-2-({2-methoxy-4-[(pyrrolidin-1-yl)piperidin-1-yl]phenyl}amino)-8,9-dimethyl-6,9-dihydro-5H-pyrrolo[3,2-h]quinazoline-7-carboxamide,
4) N-(2,6-diethylphenyl)-2-({4-[4-(dimethylamino)piperidin-1-yl]-2-methoxyphenyl}amino)-8,9-dimethyl-6,9-dihydro-5H-pyrrolo[3,2-h]quinazoline-7-carboxamide,
5) N-(2,6-diethylphenyl)-2-{[2-methoxy-4-(4-methylpiperazin-1-yl)phenyl]amino}-8,9-dimethyl-6,9-dihydro-5H-pyrrolo[3,2-h]quinazoline-7-carboxamide,
6) N-(2,6-diethylphenyl)-2-({4-[4-(2-hydroxyethyl)piperazin-1-yl]-2-methoxyphenyl}amino)-8,9-dimethyl-6,9-dihydro-5H-pyrrolo[3,2-h]quinazoline-7-carboxamide,
7) 2-{[2-methoxy-4-(4-methylpiperazin-1-yl)phenyl]amino}-8,9-dimethyl-6,9-dihydro-5H-pyrrolo[3,2-h]quinazoline-7-carboxamide,
8) 2-[(4-bromo-2-methoxyphenyl)amino]-N-(2,6-diethylphenyl)-9-methyl-6,9-dihydro-5H-pyrrolo[3,2-h]quinazoline-7-carboxamide,
9) N-(2,6-diethylphenyl)-2-{[2-methoxy-4-(4-methylpiperazin-1-yl)phenyl]amino}-9-methyl-6,9-dihydro-5H-pyrrolo[3,2-h]quinazoline-7-carboxamide,
10) N-(2,6-diethylphenyl)-2-({4-[4-(dimethylamino)piperidin-1-yl]-2-methoxyphenyl}amino)-9-methyl-6,9-dihydro-5H-pyrrolo[3,2-h]quinazoline-7-carboxamide,
11) N-(2,6-diethylphenyl)-2-({2-methoxy-4-[4-(pyrrolidin-1-yl)piperidin-1-yl]phenyl}amino)-9-methyl-6,9-dihydro-5H-pyrrolo[3,2-h]quinazoline-7-carboxamide,
12) N-(2,6-diethylphenyl)-2-[(4-{[3-(dimethylamino)propyl](methyl)amino}-2-methoxyphenyl)amino}-9-methyl-6,9-dihydro-5H-pyrrolo[3,2-h]quinazoline-7-carboxamide,
13) N-(2,6-diethylphenyl)-2-({4-[4-(2-hydroxyethyl)piperazin-1-yl]-2-methoxyphenyl}amino)-9-methyl-6,9-dihydro-5H-pyrrolo[3,2-h]quinazoline-7-carboxamide,
14) 2-[(4-bromo-2-methoxyphenyl)amino]-N-[(1S)-2-(1,3-dioxo-1,3-dihydro-2H-isoindol-2-yl)-1-phenylethyl]-9-methyl-6,9-dihydro-5H-pyrrolo[3,2-h]quinazoline-7-carboxamide,
15) 2-[(4-bromo-2-methoxyphenyl)amino]-N-(2,6-diethylphenyl)-10-methyl-5,6,7,10-tetrahydropyrrolo[3',2':6,7]cyclohepta[1,2-d]pyrimidine-8-carboxamide,
16) N-(2,6-diethylphenyl)-2-{[2-methoxy-4-(4-methylpiperazin-1-yl)phenyl]amino}-10-methyl-5,6,7,10-tetrahydropyrrolo[3',2':6,7]cyclohepta[1,2-d]pyrimidine-8-carboxamide,
17) N-(2,6-diethylphenyl)-2-({4-[4-(dimethylamino)piperidin-1-yl]-2-methoxyphenyl}amino)-10-methyl-5,6,7,10-tetrahydropyrrolo[3',2':6,7]cyclohepta[1,2-d]pyrimidine-8-carboxamide and
18) N-(2,6-diethylphenyl)-2-({2-methoxy-4-[4-(pyrrolidin-1-yl)piperidin-1-yl]phenyl}amino)-10-methyl-5,6,7,10-tetrahydropyrrolo[3',2':6,7]cyclohepta[1,2-d]pyrimidine-8-carboxamide.
19) 8-methyl-2-(methylsulfanyl)-9-(propan-2-yl)-6,9-dihydro-5H-pyrrolo[3,2-h]quinazoline-7-carboxamide
20) 8-methyl-2-(methylsulfanyl)-6,9-dihydro-5H-pyrrolo[3,2-h]quinazoline-7-carboxamide 21) 2-(methylsulfanyl)-6,9-dihydro-5H-pyrrolo[3,2-h]quinazoline-7-carboxamide
22) 2-(methylsulfanyl)-9-(propan-2-yl)-6,9-dihydro-5H-pyrrolo[3,2-h]quinazoline-7-carboxamide
23) 2-(dimethylamino)-8-methyl-6,9-dihydro-5H-pyrrolo[3,2-h]quinazoline-7-carboxamide
24) 9-(2-hydroxyethyl)-8-methyl-2-(methylsulfanyl)-6,9-dihydro-5H-pyrrolo[3,2-h]quinazoline-7-carboxamide
25) 9-(2-hydroxyethyl)-2-(methylsulfanyl)-6,9-dihydro-5H-pyrrolo[3,2-h]quinazoline-7-carboxamide
26) 2-(dimethylamino)-8-methyl-9H-pyrrolo[3,2-h]quinazoline-7-carboxamide
27) 9-methyl-2-(methylsulfanyl)-9H-pyrrolo[3,2-h]quinazoline-7-carboxamide
28) 8-methyl-2-(methylsulfanyl)-9H-pyrrolo[3,2-h]quinazoline-7-carboxamide
29) 9-(2-hydroxyethyl)-8-methyl-2-(methylsulfanyl)-9H-pyrrolo[3,2-h]quinazoline-7-carboxamide
30) 8-methyl-2-(methylsulfanyl)-9-(propan-2-yl)-9H-pyrrolo[3,2-h]quinazoline-7-carboxamide
31) 9-ethyl-2-(methylsulfanyl)-9H-pyrrolo[3,2-h]quinazoline-7-carboxamide
32) 2-(methylsulfanyl)-9-(piperidin-4-yl)-6,9-dihydro-5H-pyrrolo[3,2-h]quinazoline-7-carboxamide
33) 9-(cis 4-aminocyclohexyl)-2-(methylsulfanyl)-6,9-dihydro-5H-pyrrolo[3,2-h]quinazoline-7-carboxamide
34) 9-(cis-4-aminocyclohexyl)-2-(methylsulfanyl)-9H-pyrrolo[3,2-h]quinazoline-7-carboxamide
35) 2-(methylsulfanyl)-9-(piperidin-4-yl)-9H-pyrrolo[3,2-h]quinazoline-7-carboxamide
36) 2-(methylsulfanyl)-9H-pyrrolo[3,2-h]quinazoline-7-carboxamide
37) 2-methyl-6,9-dihydro-5H-pyrrolo[3,2-h]quinazoline-7-carboxamide
38) 9-(3-amino-2,2-dimethylpropyl)-2-(methylsulfanyl)-9H-pyrrolo[3,2-h]quinazoline-7-carboxamide hydrochloride
39) 9-(azepan-3-yl)-2-(methylsulfanyl)-9H-pyrrolo[3,2-h]quinazoline-7-carboxamide hydrochloride For a reference to any specific compound of the formula (I) of the invention, optionally in the form of a pharmaceutically acceptable salt, see the experimental section and claims.

The present invention also provides a process for the preparation of a compound of formula (I) as defined above, by using the reaction routes and synthetic schemes described below, employing the techniques available in the art and starting materials readily available. The preparation of certain embodiments of the present invention is described in the examples that follow, but those of ordinary skill in the art will recognize that the preparations described may be readily adapted to prepare other embodiments of the present invention. For example, the synthesis of non-exemplified compounds according to the invention may be performed by modifications apparent to those skilled in the art, for instance by appropriately protecting interfering groups, by changing to other suitable reagents known in the art, or by making routine modifications of reaction conditions. Alternatively other reactions referred to herein or known in the art will be recognized as having adaptability for preparing other compounds of the invention.

The reported Scheme 1 shows the preparation of a compound of formula (I).

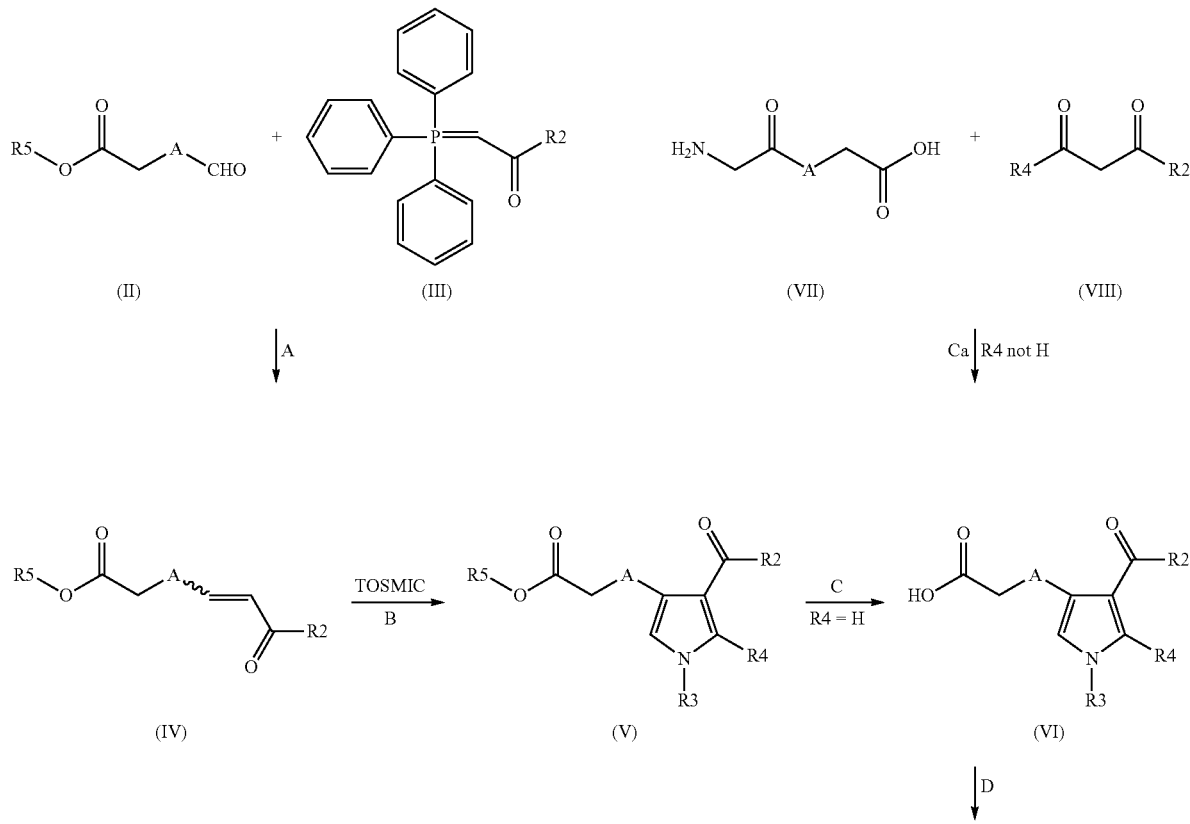

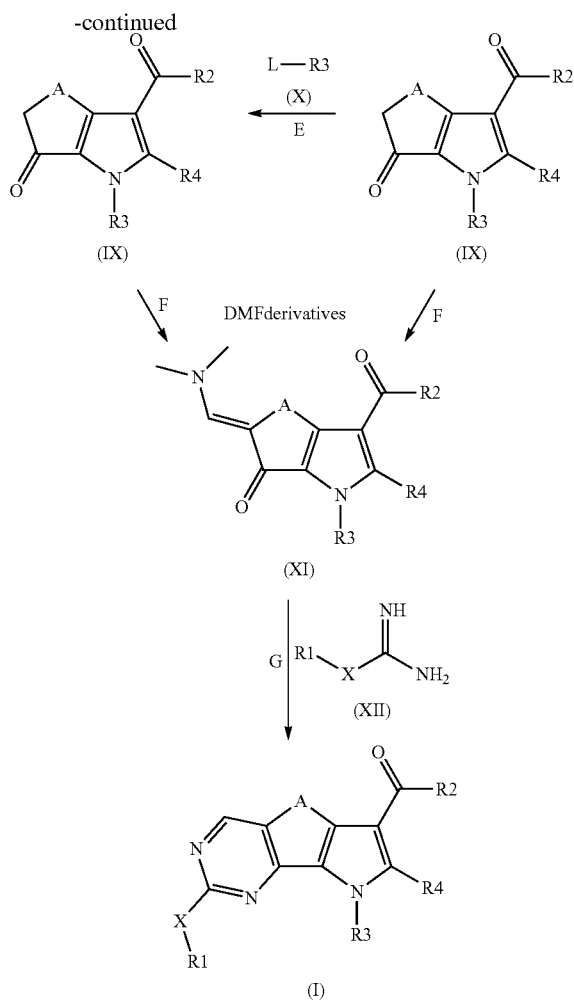

In the above scheme 1, X is a single bond or a divalent radical selected from —NR', —O— and —S—; R2 is an optionally substituted alkoxy; A is as defined in formula (I) except —CH=CH—; R1, R3, R4 and R' are as defined in formula (I) and R5 is an optionally substituted $C_1$-$C_6$ alkyl.

All those with ordinary skills in the art will appreciate that any transformation performed according to said methods may require standard modifications such as, for instance, protection of interfering groups, change to other suitable reagents known in the art, or make routine modifications of reaction conditions.

Accordingly, a process of the present invention comprises the following steps:

st.A) reacting a compound of formula (II)

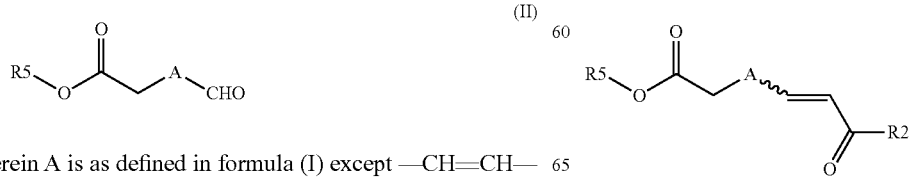

wherein A is as defined in formula (I) except —CH=CH— and R5 is an optionally substituted $C_1$-$C_6$ alkyl (for example methyl, ethyl or t-buthyl) with a compound of formula (III)

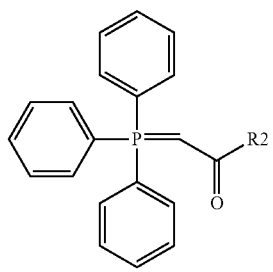

wherein R2 is an optionally substituted alkoxy (for example methoxy, ethoxy or t-butoxy);

st.B) reacting the resultant compound of the formula (IV):

wherein R2 is an optionally substituted alkoxy, R5 is an optionally substituted $C_1$-$C_6$ alkyl and A is as defined in formula (I) except —CH═CH—, with toluenesulfonylmethyl isocyanide in presence of a strong base;

st.C) hydrolyzing selectively in acidic or basic condition the resultant compound of formula (V)

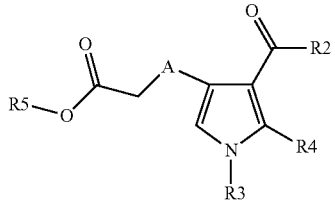

(V)

wherein R3 and R4 are hydrogen, A is as defined in formula (I) except —CH═CH—, R2 is an optionally substituted alkoxy and R5 is an optionally substituted $C_1$-$C_6$ alkyl so to obtain a compound of formula (VI)

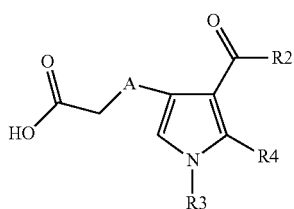

(VI)

wherein R3 and R4 are hydrogen, A is as defined in formula (I) except —CH═CH—, and R2 is an optionally substituted alkoxy;

alternatively, st.Ca) a compound of formula (VI) wherein R3 is hydrogen, R4 is as defined in formula (I) except hydrogen, A is as defined in formula (I) except —CH═CH—, and R2 is an optionally substituted alkoxy, can be obtained reacting a compound of formula (VII)

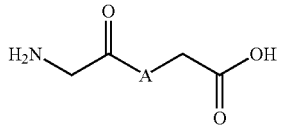

(VII)

wherein A is as defined above with a compound of formula (VIII)

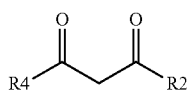

(VIII)

wherein R2 and R4 are as defined above;

st.D) cyclizing the resultant compound of formula (VI) wherein R2 is an optionally substituted alkoxy, R3 is hydrogen, R4 is as defined in formula (I), and A is as defined in formula (I) except —CH═CH—, in acidic condition so as to obtain a compound of formula (IX)

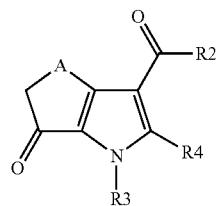

(IX)

wherein R2, R3, R4 and A are as defined above;

if needed or desired, st.E) alkylating, a compound of formula (IX) wherein R3 is hydrogen, with a compound of the formula (X):

R3-L    (X)

wherein L is OH or a group that optionally upon activation, may work as a suitable leaving group such as iodo, bromo, chloro or a sulfonate group (e.g. —OS(O)$_2$CF$_3$, —OS(O)$_2$CH$_3$ or —OS(O)$_2$PhMe), and R3 is as defined in formula (I) except hydrogen;

st.F) reacting the resultant compound of formula (IX)

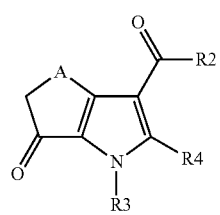

(IX)

wherein R2 is an optionally substituted alkoxy, R3 and R4 are as defined in formula (I), and A is as defined in formula (I) except —CH═CH—, with an N,N-dimethylformamide derivative;

st.G) reacting the resultant compound of formula (XI)

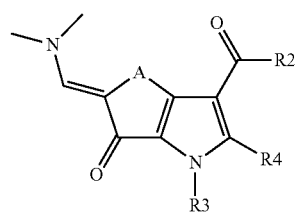

(XI)

wherein R2 is an optionally substituted alkoxy, R3 and R4 are as defined in formula (I), and A is as defined in formula (I) except —CH═CH—, with a compound of formula (XII)

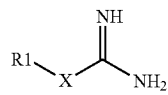

(XII)

wherein X is a single bond or a divalent radical selected from —NR', —O— and —S—; and R1 and R' are as defined in formula (I), so as to obtain a compound of formula (I)

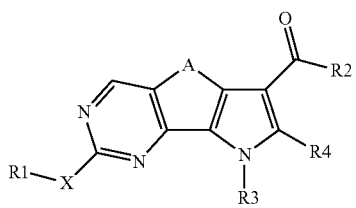

(I)

wherein X is a single bond or a divalent radical selected from —NR', —O— and —S—; R2 is an optionally substituted alkoxy; A is as defined in formula (I) except —CH=CH—; and R1, R3, R4 and R' are as defined in formula (I); optionally converting a compound of the formula (I) into another different compound of the formula (I), and, if desired, converting a compound of the formula (I) into a pharmaceutically acceptable salt thereof or converting a salt into the free compound (I).

As said above, the compounds of the formula (I) which are prepared according to the process object of the invention, can be conveniently converted into other compounds of the formula (I) by operating according to well-known synthetic conditions, the following being examples of possible conversions:

conv.1) converting a compound of the formula (I) wherein R3 is a protecting group P such as methoxymethyl or p-methoxybenzyl and into the corresponding compound of the formula (I) wherein R3 is hydrogen atom under acidic or basic conditions:

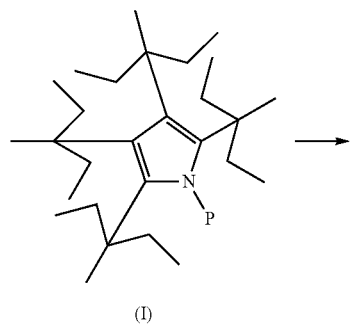

(I)

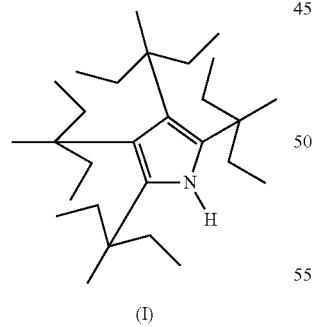

(I)

conv.2) converting a compound of the formula (I) wherein R3 is hydrogen into the corresponding compound of the formula (I) wherein R3 is as defined in formula (I) but not hydrogen, through reaction with compound of the formula R3-L (X) wherein L is OH or a group that optionally upon activation, may work as a suitable leaving group such as iodo, bromo, chloro or a sulfonate group (e.g. —OS(O)$_2$CF$_3$, —OS(O)$_2$CH$_3$ or —OS(O)$_2$PhMe), and R3 is as defined above but not hydrogen atom:

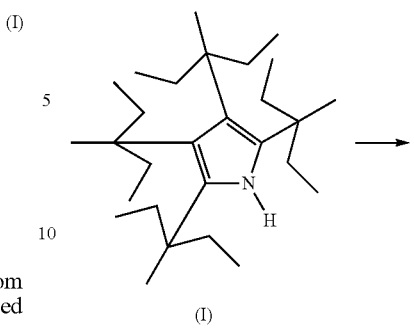

(I)

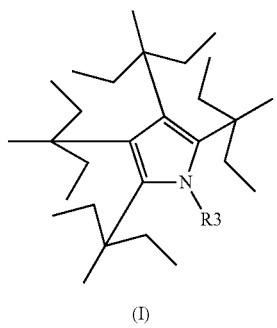

(I)

conv.3) converting a compound of the formula (I) wherein R2 is OR5 wherein R5 is an optionally substituted C$_1$-C$_6$ alkyl into the corresponding compound of the formula (I) wherein R2 is hydroxy or a corresponding salt thereof, through acidic or basic hydrolysis:

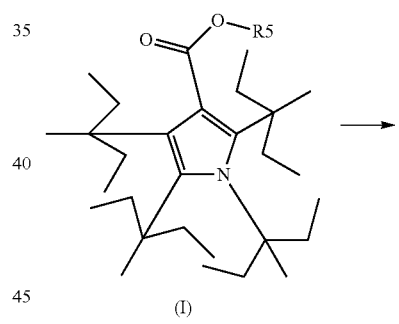

(I)

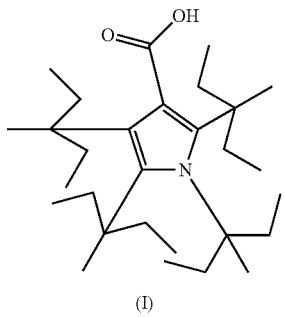

(I)

conv.4) converting a compound of the formula (I) wherein R2 is hydroxy or a corresponding salt thereof, into the corresponding compound of the formula (I) wherein R2 is a group —NR"R'" or —N(OR'")R" wherein R" and R'" are as defined in formula (I), through reaction with a derivative of formula R"R'"NH (XIII) or R"NHOR'" (XIV) wherein R" and R'" are as defined above under basic conditions and in the presence of a suitable condensing agent;

alternatively a compound of the formula (I) wherein R2 is hydroxy, may be first converted into the corresponding chloride derivative using a chlorinating agent, then reacting the resultant compound with a derivative of formula R"R'"NH (XIII) or R"NHOR'" (XIV) wherein R" and R'" are as defined above under basic conditions so as to obtain a compound of the formula (I) wherein R2 is a group —NR"R'" or —N(OR'")R":

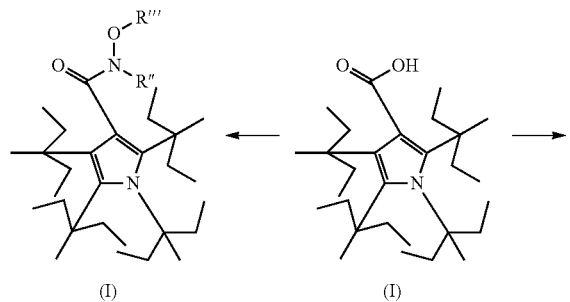

conv.5) converting a compound of the formula (I) wherein R2 is OR5 wherein R5 is an optionally substituted $C_1$-$C_6$ alkyl into the corresponding compound of the formula (I) wherein R2 is a group —NR"R'" or —N(OR'")R", wherein R" and R'" are as defined in formula (I), through reaction with a derivative of formula R"R'"NH (XIII) or R"NHOR'" (XIV) wherein R" and R'" are as defined above:

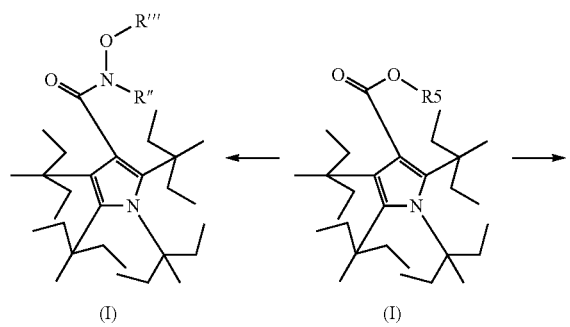

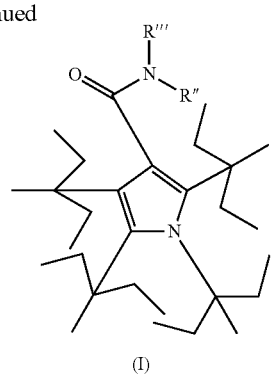

Conv.6) converting a compound of formula (I) wherein X is as defined in formula (I) except $SO_2$ and —$OSO_2$—, and R1 is an aryl, i.e. phenyl, substituted by bromine, into the corresponding compound of formula (I) wherein R1 is an aryl, i.e. phenyl, substituted by NR"R'", by treatment with an amine of formula R"R'"—NH (XIII):

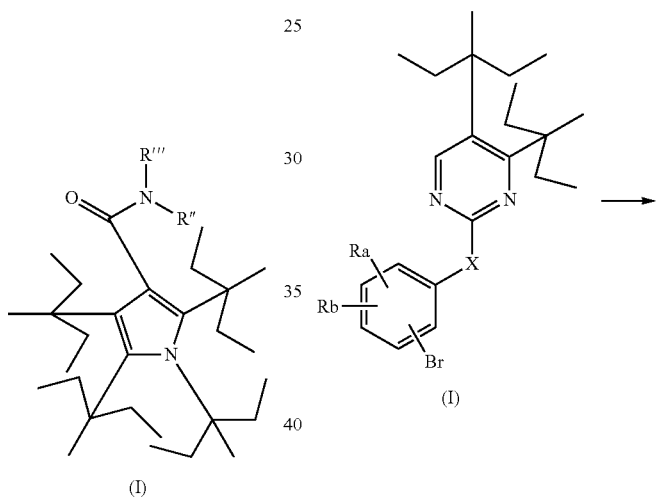

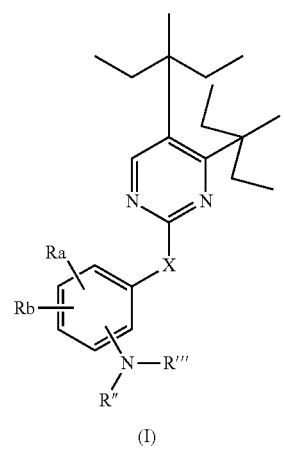

wherein Ra and Rb are independently halogen atom, except bromine, hydrogen, nitro, cyano, $C_1$-$C_6$ alkyl, polyfluorinated alkyl, polyfluorinated alkoxy, alkenyl, alkynyl, hydroxyalkyl, aryl, arylalkyl, heterocyclyl, $C_3$-$C_7$ cycloalkyl, hydroxy, alkoxy, aryloxy, heterocyclyloxy, methylenedioxy, alkylcarbonyloxy, arylcarbonyloxy, cycloalkenyloxy, heterocyclylcarbonyloxy, alkylideneaminooxy, carboxy, alkoxycarbonyl, aryloxycarbonyl, cycloalkyloxycarbonyl, heterocyclyloxycarbonyl, amino, ureido, alkylamino, dialkylamino, arylamino, diarylamino, heterocyclyamino, formylamino, alkylcarbonylamino, arylcarbonylamino, heterocyclylcarbonylamino, aminocarbonyl, alkylaminocarbonyl, dialkylaminocarbonyl, arylaminocarbonyl, heterocyclylaminocarbonyl, alkoxycarbonylamino, hydroxyaminocarbonyl, alkoxyimino, alkylsulfonylamino, arylsulfonylamino, heterocyclylsulfonylamino, formyl, alkylcarbonyl, arylcarbonyl, cycloalkylcarbonyl, heterocyclylcarbonyl, alkylsulfonyl, arylsulfonyl, aminosulfonyl, alkylaminosulfonyl, dialkylaminosulfonyl, arylaminosulfonyl, heterocyclylaminosulfonyl, arylthio, alkylthio, phosphonate or alkylphosphonate;

Conv.7) converting a compound of the formula (I) wherein X is —NH— and R1 is hydrogen, into the corresponding compound of the formula (I) wherein R1 is an aryl, i.e. phenyl, substituted by Ra, Rb, Rc:

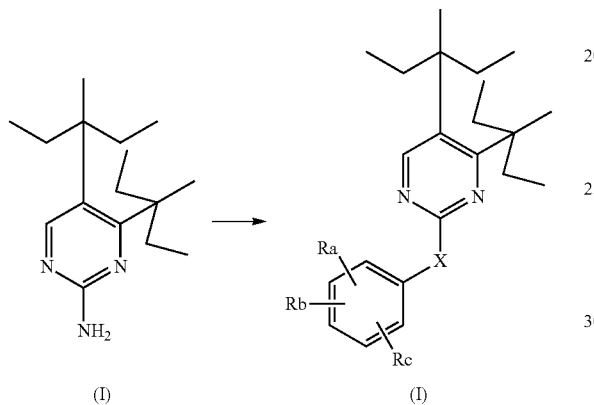

(I)                                (I)

wherein Ra, Rb and Rc are independently hydrogen, nitro, cyano, $C_1$-$C_6$ alkyl, polyfluorinated alkyl, polyfluorinated alkoxy, alkenyl, alkynyl, hydroxyalkyl, aryl, arylalkyl, heterocyclyl, $C_3$-$C_7$ cycloalkyl, hydroxy, alkoxy, aryloxy, heterocyclyloxy, methylenedioxy, alkylcarbonyloxy, arylcarbonyloxy, cycloalkenyloxy, heterocyclylcarbonyloxy, alkylideneaminooxy, carboxy, alkoxycarbonyl, aryloxycarbonyl, cycloalkyloxycarbonyl, heterocyclyloxycarbonyl, amino, ureido, alkylamino, dialkylamino, arylamino, diarylamino, heterocyclyamino, formylamino, alkylcarbonylamino, arylcarbonyl amino, heterocyclylcarbonylamino, aminocarbonyl, alkyl aminocarbonyl, dialkylaminocarbonyl, aryl aminocarbonyl, heterocyclylaminocarbonyl, alkoxycarbonylamino, hydroxyaminocarbonyl, alkoxyimino, alkylsulfonylamino, arylsulfonylamino, heterocyclylsulfonylamino, formyl, alkylcarbonyl, arylcarbonyl, cycloalkylcarbonyl, heterocyclylcarbonyl, alkylsulfonyl, arylsulfonyl, aminosulfonyl, alkylaminosulfonyl, dialkylaminosulfonyl, arylaminosulfonyl, heterocyclylaminosulfonyl, arylthio, alkylthio, phosphonate or alkylphosphonate, by treatment with an iodo derivative of the formula (XV)

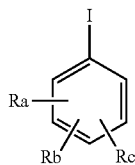

wherein Ra, Rb and Rc are as defined above, in presence of palladium;

Conv.8) converting a compound of the formula (I) wherein X is as defined in formula (I) except $SO_2$ and —$OSO_2$—, and R1 is an aryl, i.e. phenyl, substituted by —COOPg, wherein Pg is a suitable protecting group, into the corresponding compound of formula (I) wherein R1 is an aryl, i.e. phenyl, substituted by —COOH, through conditions well known in the literature (see Teodora W. Green, Pere G. M. Wuts):

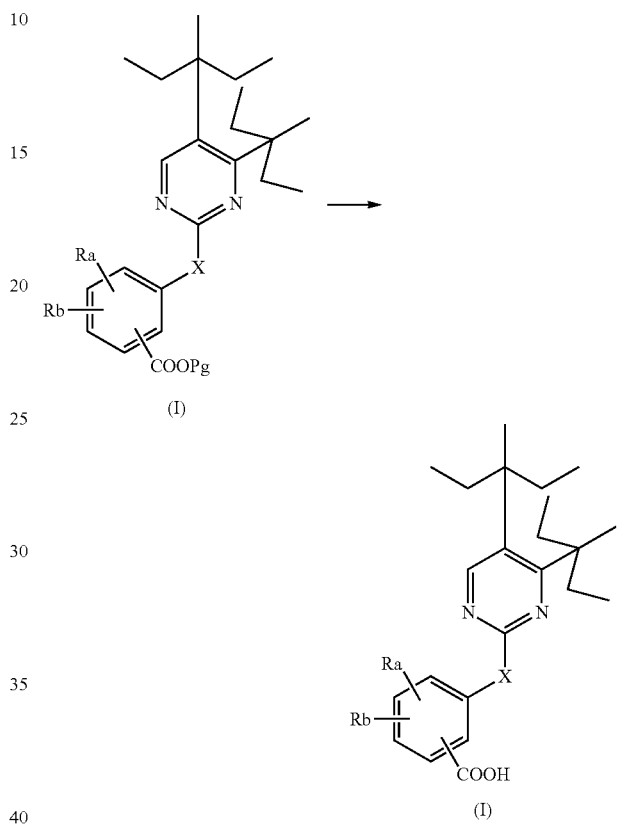

(I)

(I)

wherein Ra and Rb are independently halogen atom, hydrogen, nitro, cyano, $C_1$-$C_6$ alkyl, polyfluorinated alkyl, polyfluorinated alkoxy, alkenyl, alkynyl, hydroxyalkyl, aryl, arylalkyl, heterocyclyl, $C_3$-$C_7$ cycloalkyl, hydroxy, alkoxy, aryloxy, heterocyclyloxy, methylenedioxy, alkylcarbonyloxy, arylcarbonyloxy, cycloalkenyloxy, heterocyclylcarbonyloxy, alkylideneaminooxy, carboxy, alkoxycarbonyl, aryloxycarbonyl, cycloalkyloxycarbonyl, heterocyclyloxycarbonyl, amino, ureido, alkylamino, dialkylamino, arylamino, diarylamino, heterocyclyamino, formylamino, alkylcarbonylamino, arylcarbonylamino, heterocyclylcarbonylamino, aminocarbonyl, alkylaminocarbonyl, dialkylaminocarbonyl, arylaminocarbonyl, heterocyclylaminocarbonyl, alkoxycarbonylamino, hydroxyaminocarbonyl, alkoxyimino, alkylsulfonylamino, arylsulfonylamino, heterocyclylsulfonylamino, formyl, alkylcarbonyl, arylcarbonyl, cycloalkylcarbonyl, heterocyclylcarbonyl, alkylsulfonyl, arylsulfonyl, aminosulfonyl, alkylaminosulfonyl, dialkylaminosulfonyl, arylaminosulfonyl, heterocyclylaminosulfonyl, arylthio, alkylthio, phosphonate or alkylphosphonate;

Conv.9) converting a compound of the formula (I) wherein X is as defined in formula (I) except $SO_2$ and —$OSO_2$—, and R1 is an aryl, i.e. phenyl, substituted by —COOH, into the corresponding compound of formula (I) wherein R1 is an aryl, i.e. phenyl, substituted by —CONR"R'", wherein R" and R'"

are as defined above, by treatment with an amine of formula R"R'"—NH (XIII), in the presence of the suitable condensing agents:

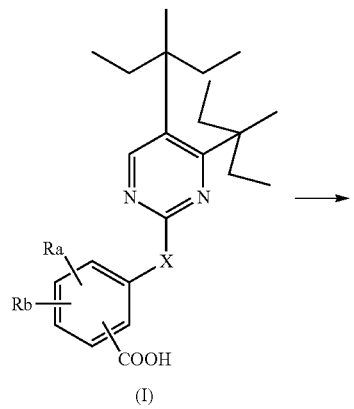

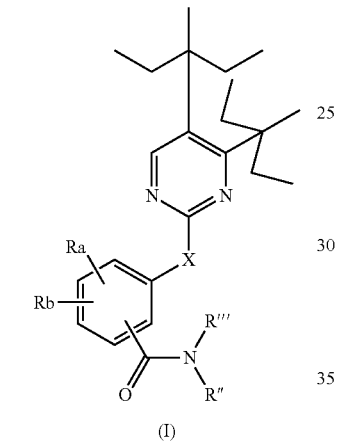

wherein Ra and Rb are independently halogen atom, hydrogen, nitro, cyano, $C_1$-$C_6$ alkyl, polyfluorinated alkyl, polyfluorinated alkoxy, alkenyl, alkynyl, hydroxyalkyl, aryl, arylalkyl, heterocyclyl, $C_3$-$C_7$ cycloalkyl, hydroxy, alkoxy, aryloxy, heterocyclyloxy, methylenedioxy, alkylcarbonyloxy, arylcarbonyloxy, cycloalkenyloxy, heterocyclylcarbonyloxy, alkylideneaminooxy, carboxy, alkoxycarbonyl, aryloxycarbonyl, cycloalkyloxycarbonyl, heterocyclyloxycarbonyl, amino, ureido, alkylamino, dialkylamino, arylamino, diarylamino, heterocyclyamino, formylamino, alkylcarbonylamino, arylcarbonylamino, heterocyclylcarbonylamino, aminocarbonyl, alkylaminocarbonyl, dialkylaminocarbonyl, arylaminocarbonyl, heterocyclylaminocarbonyl, alkoxycarbonylamino, hydroxyaminocarbonyl, alkoxyimino, alkylsulfonylamino, arylsulfonylamino, heterocyclylsulfonylamino, formyl, alkylcarbonyl, arylcarbonyl, cycloalkylcarbonyl, heterocyclylcarbonyl, alkylsulfonyl, arylsulfonyl, aminosulfonyl, alkylaminosulfonyl, dialkylaminosulfonyl, arylaminosulfonyl, heterocyclylaminosulfonyl, arylthio, alkylthio, phosphonate or alkylphosphonate;

Conv.10) converting a compound of formula (I) wherein R1 is hydrogen and X is —NH— into the corresponding compound of formula (I) wherein R1 is iodine and X is a single bond, by reaction with iso-amylnitrite and diiodomethane or cesium iodide, in the presence of iodine and CuI:

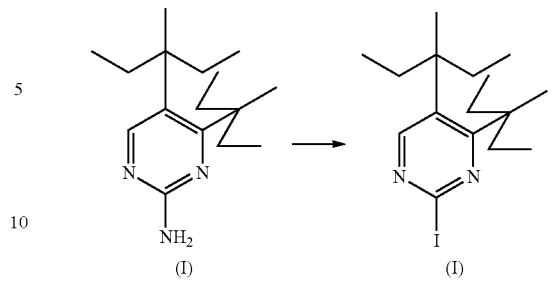

Conv.11) converting a compound of formula (I) wherein R1 is iodine and X is a single bond into the corresponding compound of formula (I) wherein X is —NH— and R1 is an optionally substituted aryl, by reaction with an optionally substituted arylamine of formula R1-$NH_2$ (XVI) wherein R1 is as defined above in the presence of $Pd(OAc)_2$ and BINAP:

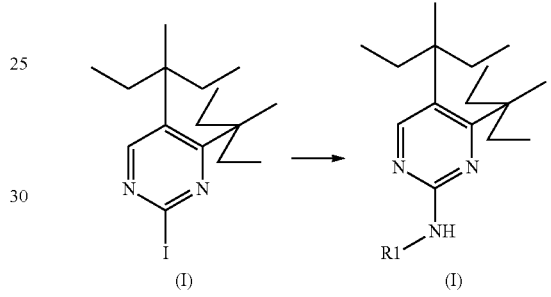

Conv.12) converting a compound of formula (I) wherein R1 is iodine and X is a single bond into the corresponding compound of formula (I) wherein X is single bond and R1 is as defined in formula (I), by reaction with a compound of formula (XVII):

R1-Q          (XVII)

wherein R1 is as defined above and Q is a suitable group such as —$B(OH)_2$, —$B(OAlk)_2$, —$Sn(Alk)_4$, ZnHal, or MgHal, which can undergo palladium mediated carbon bond formation:

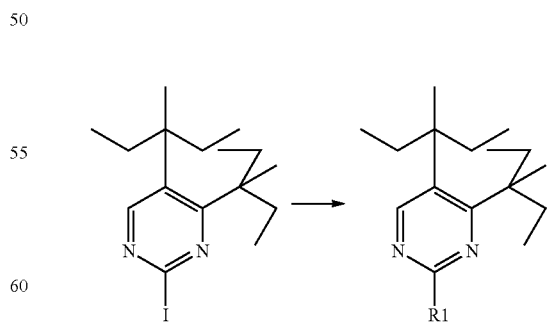

Conv.13) converting a compound of formula (I) wherein R1 is as defined in formula (I) and X is —S— into the corresponding compound of formula (I) wherein X is —$SO_2$— under oxidative conditions:

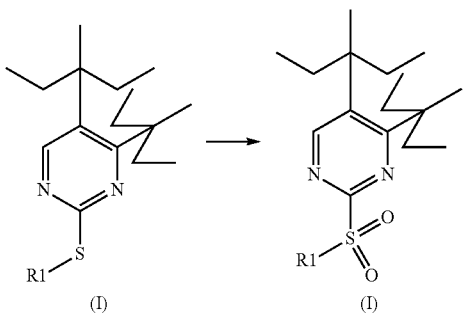

Conv.14) converting a compound of formula (I) wherein R1 is as defined in formula (I) and X is —S— into the corresponding compound of formula (I) wherein X is —NR'— by reacting the sulfonyl group with an amine of formula R1-NHR' (XVIa) wherein R1 and R' are as defined in formula (I):

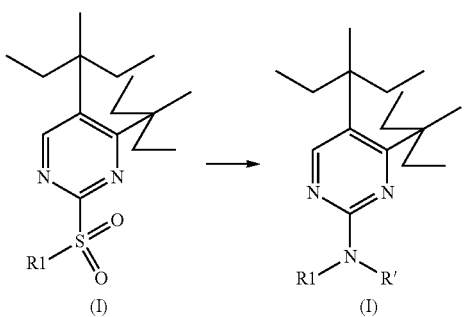

Conv.15) converting a compound of formula (I) wherein R1 is as defined in formula (I) and X is —SO$_2$— into the corresponding compound of formula (I) wherein X is —O— by reacting the sulfonyl group with a compound of formula R1-OH(XVIII) wherein R1 is as defined in formula (I) except hydrogen:

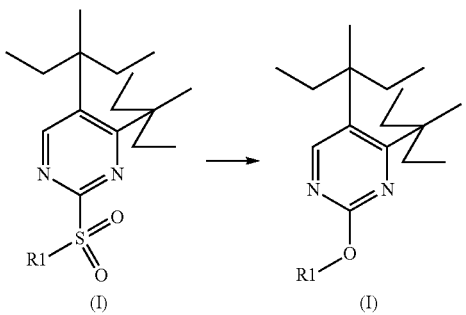

Conv.16) converting a compound of formula (I) wherein R1 is methyl and X is —O— into the corresponding compound of formula (I) wherein R1 is hydrogen and X is —O—:

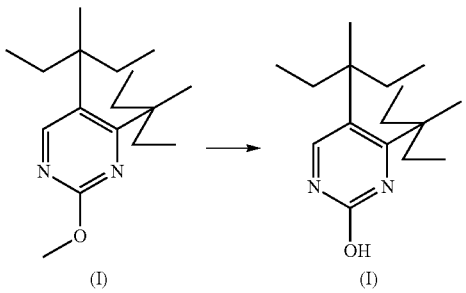

Conv.17) converting a compound of formula (I) wherein R1 is hydrogen and X is —O— into a compound of formula (I) wherein R1 is trifluoromethyl and X is —OSO$_2$— by reaction with a triflating agent:

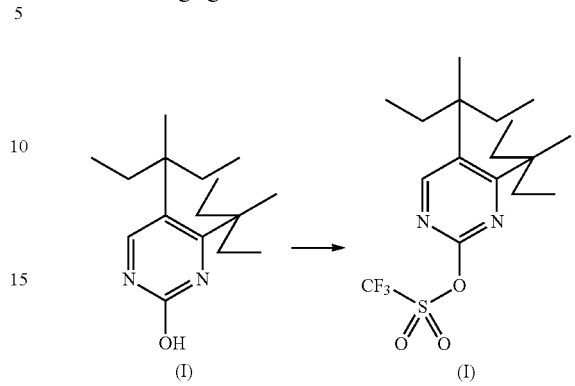

Conv.18) converting a compound of formula (I) wherein R1 is trifluoromethyl and X is —OSO— into the corresponding compound of formula (I) wherein X is —O— and R1 is as defined in formula (I), by reaction with a compound of formula R1-OH(XVIII) wherein R1 is as defined above except hydrogen:

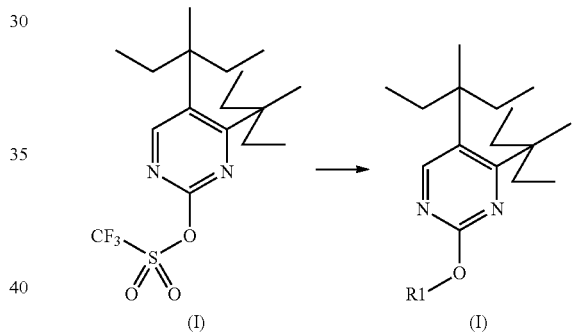

Conv.19) converting a compound of formula (I) wherein R1 is trifluoromethyl and X is —OSO$_2$— into the corresponding compound of formula (I) wherein X is —NR'— and R1 is as defined in formula (I) except hydrogen, by reaction with a compound of formula R1-NHR' (XVIa) wherein R1 is as defined above:

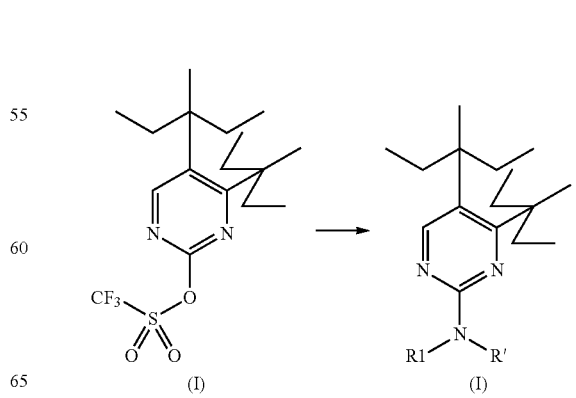

Conv.20) converting a compound of formula (I) wherein R1 is trifluoromethyl and X is —OSO₂— into the corresponding compound of formula (I) wherein X is —S— and R1 is as defined in formula (I) except hydrogen, by reaction with a thiol of formula R1-SH (XIX) wherein R1 is as defined above except hydrogen:

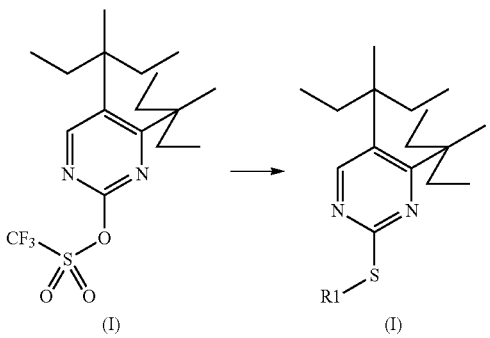

Conv.21) converting a compound of formula (I) wherein R1 is trifluoromethyl and X is —OSO₂— into the corresponding compound of formula (I) wherein X is a single bond and R1 is as defined in formula (I) except hydrogen, by reaction with a compound of formula R1-Q (XVII) wherein R1 is as defined above except hydrogen and Q is a suitable group such as —B(OH)₂, —B(OAlk)₂, —Sn(Alk)₄, ZnHal, or MgHal, which can undergo palladium mediated carbon bond formation:

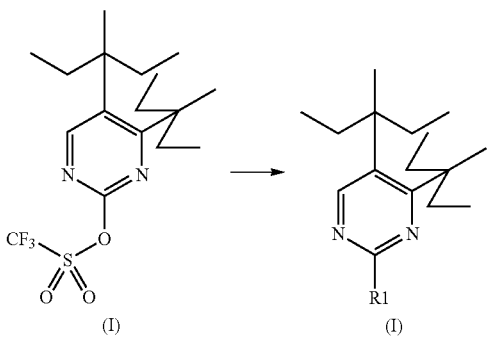

Conv.22) converting a compound of formula (I) wherein R1 is methyl and X is —S— into the corresponding compounds of formula (I) wherein R1 is an optionally substituted aryl and X is a single bond, by reacting it with an arylboronic acid of formula R1-B(OH)₂ (XVIIa), wherein R1 is an optionally substituted aryl, in the presence of a palladium derivative:

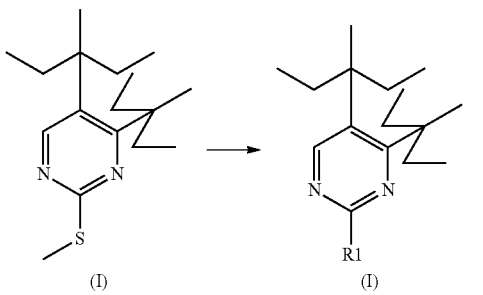

Conv. 23) converting a compound of formula (I) wherein A is a divalent group such as —CH₂—CH₂— into the corresponding compound of formula (I) wherein A is a —CH=CH— group, by treatment with an oxidizing agent, or under dehydrogenating operative conditions in the presence of a Pd or Pt catalyst:

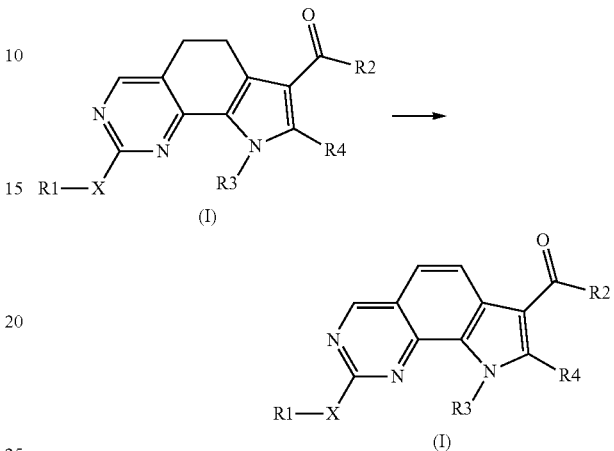

wherein X, R1, R2, R3 and R4 are as defined in formula (I).

Conv. 24) converting a compound of formula (I) wherein R4 is hydrogen and A is a divalent group such as —CH₂=CH₂— into the corresponding compound of formula (I) wherein R4 is hydrogen and A is a —CH=CH— group, by first converting to the compound of formula (XX) with an excess of N-iodosuccinimide, and by subsequently removing the iodine, in the presence of a palladium derivative:

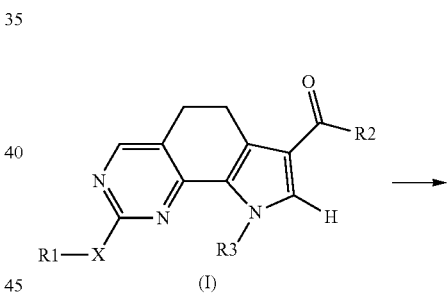

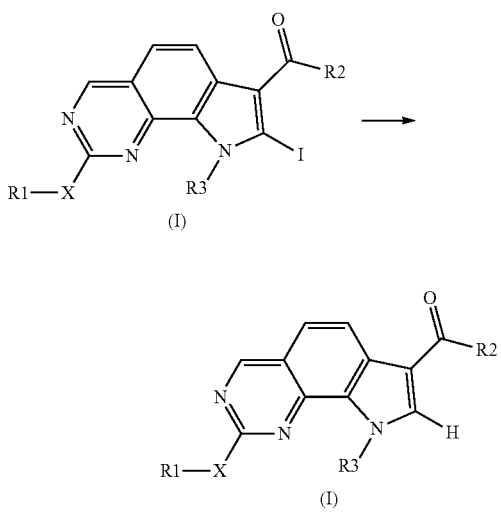

wherein X, R1, R2, and R3 are as defined in formula (I) and R4 is hydrogen.

Conv. 25) removing any protecting group or groups and, if desired, forming a salt.

According to steps (st.A) of the process, an aldehyde of formula (II) is reacted with a phosphorane of formula (III) in a suitable solvent such as, for instance, toluene, xylene, THF or $Et_2O$ at a temperature ranging from room temperature to reflux, and for a time ranging from 1 to about 12 hours. Preferably, the above reaction is carried out in toluene at reflux so to obtain a compound of formula (IV).

According to step (st.B), a compound of formula (IV) is reacted with TOSMIC, in the presence of a base such as KOH, NaH, $LiN(TMS)_2$ in a suitable solvent such as, for instance, toluene, THF or $Et_2O$ at a temperature ranging from −78° C. to room temperature, and for a time ranging from 1 to about 12 hours. Preferably, the above reaction is carried out in presence of $LiN(TMS)_2$ in THF at −78° C., so as to obtain a compound of formula (V).

According to step (st.C), a compound of formula (V) wherein R3 is hydrogen, R4 is hydrogen and A is as defined in formula (I) except —CH=CH—, R2 is an optionally substituted alkoxy and R5 is an optionally substituted alkyl is converted into mono-carboxylic acid derivative (VI), in the presence of a base such as KOH, NaOH, LiOH or $Na_2CO_3$ in a suitable solvent such as, for instance, $H_2O$, dioxane or admixtures thereof at a temperature ranging from 0° C. to room temperature, and for a time ranging from 1 to about 24 hours. Preferably, the above reaction is carried out in presence of LiOH in a mixture dioxane/$H_2O$ at room temperature so as to obtain a compound of formula (VI).

Alternatively according to step (st.Ca), a compound of formula (VII) is reacted with a compound of formula (VIII), in the presence of AcONa or sodium ethylate in a suitable solvent such as, for instance, $H_2O$, EtOH or AcOH at a temperature ranging from room temperature to reflux, and for a time ranging from 1 to about 24 hours. Preferably, the above reaction is carried out in presence of AcONa in $H_2O$ at reflux so as to obtain a compound of formula (VI) wherein R3 is hydrogen, R4 is as defined above except hydrogen, and R2 and A are as defined above.

According to step (st.D) of the process, a compound of formula (VI) wherein R4 is as defined in formula (I), may be converted into a compound of formula (IX) in presence of an TFAA or PPA in a suitable solvent such as TFA, at a temperature ranging from room temperature to reflux, and for a time ranging from 1 to about 8 hours. Preferably, the above reaction is carried out in presence of TFAA in TFA at room temperature so as to obtain a compound of formula (IX).

According to step (st.E) of the process, a compound of the formula (IX), wherein R3 is hydrogen atom, is reacted with a compound of formula (X), as defined above, wherein L is OH, in which case the Mitsunobu conditions can be employed, or a group that optionally upon activation may work as a leaving group, such as a halogen atom, a tosylate, mesylate or triflate.

In the former instance, that is, when a Mitsunobu protocol is employed, the reaction can be accomplished using a dialkyl azodicarboxylate, such as diethylazodicarboxylate (DEAD), diisopropyl azodicarboxylate (DIAD) or the like, in the presence of a trialkyl or triaryl phosphine, preferably triphenyl phosphine in a suitable solvent such as tetrahydrofuran, 1,4-dioxane, 1,2-dimethoxyethane, acetonitrile.

When L is an halogen or a group such as tosylate, mesylate or triflate or the like the conversion can be accomplished using a suitable base such as, for instance, NaH, $K_2CO_3$, $Cs_2CO_3$, DBU, KO-t-Bu and the like, in a suitable solvent such as tetrahydrofuran, acetonitrile, N,N-dimethylformamide, N,N-dimethylacetamide and the like. Said reactions can be carried out at temperatures ranging from 0° C. to reflux and for a time ranging from 30 minutes to about 48 hours.

According to step (st.F) of the process, the compound of the formula (IX) is reacted with an N,N-dimethylformamide derivative for instance with a N,N-dimethylformamide derivative such as N,N-dimethylformamide-di-tert-butylacetale, N,N-dimethylformamide-diisopropylacetale, N,N-dimethylformamide-dimethylacetale, N,N-dimethylformamide-diethylacetale or tris(dimethylamino)methane in a suitable solvent such as, for instance, DMF or toluene, at a temperature ranging from room temperature to reflux, and for a time ranging from about 1 to about 48 hours. Preferably, the reaction is carried out in presence of tris(dimethylamino) methane neat or in DMF at 90° C. to obtain a compound of formula (XI).

According to step (st.G) of the process, the compound of the formula (XI) is reacted with a derivative of formula (XII) wherein X is a single bond or a divalent radical selected from —NR'—, —O— and —S— wherein R' is as defined in formula (I), R1 is as defined in formula (I); so as to obtain a compound of the formula (I) as defined above wherein X and R1 are as defined above through pyrimidine ring formation in presence eventually of a base such as AcOK, $K_2CO_3$ or $Na_2CO_3$ in a suitable solvent such as, for instance, DMF, EtOH or toluene, at a temperature ranging from room temperature to reflux, and for a time ranging from about 1 to about 48 hours. Preferably, the reaction is carried out in presence of DMF at 120° C. Alternatively microwave irradiation can be used instead of heating.

According to conversion (conv.1) of the process, the compound of formula (I) wherein R3 is a group selected from methoxymethyl or p-methoxybenzyl may be converted into another compound of the formula (I) wherein R3 is hydrogen atom by reaction in acidic conditions, for instance with AcOH, TFA or HCl or in basic conditions, for instance NaOH and in the presence of a suitable solvent such as MeOH, DCM or dioxane, at a temperature ranging from room temperature to reflux and for a time ranging from 1 to about 12 hours.

According to conversion (conv.2) of the process, a compound of the formula (I), wherein R3 is hydrogen atom, may be converted into a compound of formula (I), wherein R2 is as defined above except hydrogen atom, by reaction with a suitable compound of the formula (X) as defined above, when L is OH, in which case the Mitsunobu conditions can be employed, or a group that optionally upon activation may work as a leaving group, such as an halogen atom, a tosylate, mesylate or triflate.

In the former instance, that is, when a Mitsunobu protocol is employed, the reaction can be accomplished using a dialkyl azodicarboxylate, such as diethylazodicarboxylate (DEAD), diisopropyl azodicarboxylate (DIAD) or the like, in the presence of a trialkyl or triaryl phosphine, preferably triphenyl phosphine in a suitable solvent such as tetrahydrofuran, 1,4-dioxane, 1,2-dimethoxyethane, acetonitrile.

When L is an halogen or a group such as tosylate, mesylate or triflate or the like the conversion can be accomplished using a suitable base such as, for instance, NaH, $K_2CO_3$, $Cs_2CO_3$, DBU, KO-t-Bu and the like, in a suitable solvent such as tetrahydrofuran, acetonitrile, N,N-dimethylformamide, N,N-dimethylacetamide and the like. Said reactions can be carried out at temperatures ranging from 0° C. to reflux and for a time ranging from 30 minutes to about 48 hours.

According to conversion (conv.3) of the process, a compound of the formula (I) wherein R2 is OR5 wherein R5 is an optionally substituted alkyl may be converted into the corresponding carboxylic acid derivative of the formula (I)

wherein R2 is hydroxyl or their corresponding salts through basic or acidic hydrolysis conditions, widely known in the art. Preferably, the reaction is carried out in presence of NaOH in dioxane/$H_2O$ at reflux.

According to conversion (conv.4) of the process, the compound of formula (I) wherein R2 is hydroxy or a corresponding salt, may be converted into a derivative of the formula (I) wherein R2 is a group NR"R'" or N(OR'")R" wherein R" and R' are as defined in formula (I). The reaction is carried out in presence of a compound of formula either (XIII) or (XIV) as defined above in presence of a base for example, with DIPEA or TEA, in a suitable solvent such as DCM, DMF, THF, or dioxane, and in the presence of a suitable condensing agent such as DCC, EDCI or TBTU; catalytic amounts of PyBOP or HOBt may be also required. Preferably, the reaction is carried out in presence of DIPEA and TBTU in DMF at room temperature.

Alternatively the same conversion may be obtained by first reacting the compound of formula (I) wherein R2 is hydroxy or the corresponding salt with a chlorinating agent for instance oxalyl dichloride or $SOCl_2$ in a suitable solvent, for instance DCM, Toluene, THF, dioxane or DMF, at a temperature ranging from room temperature to 100° C. so to obtain the corresponding chloride derivative. Preferably, the reaction is carried out in presence of $SOCl_2$ in THF at reflux.

According to conversion (conv.5) of the process, a compound of the formula (I) wherein R2 is OR5 wherein R5 is an optionally substituted alkyl, is reacted with a suitable compound of the formula (XIII) or (XIV) as defined above, in the presence of a base such as NaH, $NaN(TMS)_2$ or $LiN(TMS)_2$ in a suitable solvent, for instance $Et_2O$, THF or dioxane, at a temperature ranging from −10° C. to 40° C., and for a time ranging from about 10 minutes to about 12 hours, so to obtain another compound of the formula (I) wherein R2 is an amino group of formula —NR"R'" or —N(OR'")R". Preferably, the reaction is carried out in presence of $LiN(TMS)_2$ in THF at 0° C.

According to conversion (conv.6) of the process, replacement of bromine with —NR"R'" moiety was achieved reacting the starting material with an amine of the formula (XIII) as defined above, in a suitable solvent such as THF or dioxane, and in the presence of catalytic amounts of $Pd_2(dba)_3$, 2-dicyclohexylphosphino-2'-(N,N-dimethylamino)-biphenyl and a base such as $LiN(TMS)_2$ at a temperature ranging from room temperature to reflux and for a time ranging from 1 to about 24 hours.

According to conversion (conv.7) of the process, the compound of formula (I) as defined above is reacted with compounds of the formula (XV) as defined above, according to conventional methods. As an example the reaction can be carried out in a suitable solvent such as DMF, DME, dioxane or $CH_3CN$ and in the presence of an optionally-substituted-aryliodine of the formula (XV) as defined above, catalytic amounts of $Pd_2(dba)_3$, BINAP or 2-(dicyclohexylphosphino)-2',4',6'-triisopropyl-1,1'-biphenyl (X-phos) and a base such as $K_2CO_3$, potassium phosphate or $Cs_2CO_3$, at a temperature ranging from room temperature to 110° C. and for a time ranging from 2 to about 24 hours.

According to conversion (conv.8) of the process, deprotection of the carboxylic residue into the corresponding acid can be achieved using procedure well known in the art in acidic condition for example with HCl or TFA in a suitable solvent, for instance, THF or dioxane, at a temperature ranging from room temperature to 60° C. and for a time ranging from about 1 to about 12 hours.

According to conversion (conv.9) of the process, transformation of the acid residue into the corresponding amide derivatives —CONR"R'", wherein R" and R'" are as defined above, can be obtained by reaction of the acid derivatives with an amine of the formula (XIII) as defined above, under basic conditions, preferably with DIPEA or TEA, in a suitable solvent such as DCM, DMF, THF, or dioxane, and in the presence of a suitable condensing agent such as DCC, EDCI or TBTU; catalytic amounts of PyBOP or HOBt may be also required, at a temperature ranging from room temperature to 60° C. and for a time ranging from about 1 to about 24 hours.

According to conversion (conv.10) of the process, compounds of formula (I) wherein R1 is iodine and X is a single bond may be prepared by the corresponding compounds of formula (I) wherein R1 is hydrogen and X is —NH—; the reaction carried out using iso-amylnitrite and diiodomethane or cesium iodide, in the presence of iodine and CuI in a suitable solvent such as THF, $Et_2O$ or DME, at a temperature ranging from room temperature to about 70° C., and for a time of about 8 hours to about 48 hours.

According to conversion (conv.11) of the process, replacement of the iodine with an arylamine of formula $R1\text{-}NH_2$ (XVI) may be carried out in a suitable solvent such as DMF, DME or $CH_3CN$ and in the presence of catalytic amounts of $Pd(OAc)_2$, BINAP or Xantphos and a base such as $K_2CO_3$, potassium phosphate or $Cs_2CO_3$, at a temperature ranging from room temperature to 110° C. and for a time ranging from about 2 to about 24 hours.

According to conversion (conv.12) of the process, replacement of the iodine with group of formula R1 may be carried out by exploiting any of the cross-coupling reactions suitable for the formation of carbon-carbon bonds. Said reactions, which are well known in the art, imply coupling with a suitable organometal reagent such as for instance organoboron (Suzuki reaction), organotin (Stille reaction), organomagnesium (Kumada reaction), or organozinc (Negishi reaction) and the like. Preferred reaction is the Suzuki reaction where the appropriate aryl or heteroharylboronic derivative is used in the presence of a palladium based catalyst such as $PdCl_2(dppf)_2CH_2Cl_2$ or $Pd_2(dba)_3$ or $Pd(PPh_3)_4$, in a suitable solvent such as DMF, DCM, MeOH, $CH_3CN$, or in a mixture of solvents, such as dimethoxyethane and water, optionally in the presence of a base such as sodium, cesium carbonate or cesium fluoride, at a temperature ranging from room temperature to 100° C.

According to conversion (conv. 13) of the process, the transformation of thio group into the sulfonyl group can be obtained by reaction with an oxidant agent well-known to those skilled in the art, such as for instance, oxone in a suitable solvent such as tetrahydrofuran, 1,4-dioxane, acetone, optionally in the presence of water as co-solvent or m-chloroperbenzoic acid in the presence of a suitable solvent preferably DCM at room temperature.

According to conversion (conv. 14) of the process, the replacing of the sulfonyl group with a suitable amino derivative is preferably carried out with an amine of formula R1-NHR' (XVIa) in the presence of DMF, DME, dioxane, $CH_3CN$, N-methyl-pyrrolidone or diglyme, at a temperature ranging from room temperature to about 100° C.

According to conversion (conv. 15) of the process, the replacing of the sulfonyl group may be easily obtained by reaction with an alcohol or phenol derivative of formula (XVIII). The reaction may be carried out in the presence of a base such as $K_2CO_3$ or $Na_2CO_3$, butyl lithium, $LiN(TMS)_2$, NaH or the like, in a suitable solvent such as DMF or THF, and by working at a temperature ranging from room temperature to about 100° C.

According to conversion (conv. 16) of the process, the removing of the methyl residue may be obtained in presence of trimethylsilylchloride and sodium iodide. The reaction may be carried out in a suitable solvent such as $CH_3CN$, and by working at a temperature ranging from room temperature to about reflux.

According to conversion (conv.17) of the process compounds with a trifluoromethanesulfonyl group may be obtained by reacting the compounds of formula (I) wherein X is —O— and R1 is hydrogen with a triflating agent such as trifluoromethanesulfonic anhydride, trifluoromethanesulfonylchloride or N-phenyl-bis(trifluoromethanesulfonimide), optionally in the presence of a base such as TEA or DIPEA, in a suitable solvent such as DCM, THF or dioxane at a temperature ranging from −78° C. to room temperature.

According to conversion (conv.18) of the process, the reaction may be carried out with an alcohol of formula (XVIII), by operating in a suitable solvent such as dioxane, THF, DME, $CH_3CN$, DMF or DMSO, at a temperature ranging from room temperature to about 90° C., optionally in the presence of a base such as $K_2CO_3$, potassium tert butoxide or NaH.

Alternatively the reaction may be carried out in a suitable solvent such as toluene, DMF, DME or $CH_3CN$, in the presence of $Pd(OAc)_2$, (±)-BINAP and a base such as potassium phosphate or $K_2CO_3$ or $CsCO_3$ at a temperature ranging from 0° C. to 100° C.

According to conversion (conv.19) of the process, compounds of formula (I) wherein R1 is as defined in formula (I) except hydrogen and X is —NR'— can be obtained from the corresponding trifluoromethanesulfonyl compounds with an amine of formula R1-NHR' (XVIa). The reaction is typically obtained by operating in a suitable solvent such as dioxane, THF, DME, $CH_3CN$, DMF or DMSO, at a temperature ranging from room temperature to 90° C., optionally in the presence of a base such as $K_2CO_3$ or TEA.

According to conversion (conv.20) of the process, compounds of formula (I) wherein R1 is as defined in formula (I) except hydrogen and X is —S—, can be obtained from the corresponding trifluoromethanesulfonyl compounds. The conversion is carried out by reaction with a thiol of formula R1-SH(XIX) wherein R1 is as defined above in a suitable solvent such as THF, DMF, DCM, MeOH, DME or $CH_3CN$, at a temperature ranging from room temperature to 100° C.

According to conversion (conv.21) of the process, compounds of formula (I), wherein R1 is as defined above, can be obtained by the corresponding trifluoromethanesulfonyl. The conversion is carried out by reaction with derivatives of formula (XVII) in a suitable solvent such as DMF, DCM, MeOH, DME or $CH_3CN$, in the presence of $Pd_2(dba)_3$, $PdCl_2$ (dppf) or $Pd(PPh_3)_4$, optionally in the presence of cesium fluoride, at a temperature ranging from room temperature to 100° C.

According to conversion (conv.22) of the process, compounds of formula (I) wherein R1 is an optionally substituted aryl and X is single bond, can be obtained by the corresponding compounds of formula (I) wherein X is —S— and R1 is methyl. The conversion is carried out by reaction with boronic acids of formula (XVIIa) in a suitable solvent such as DMF, THF, DCM, MeOH, DME or $CH_3CN$, in the presence of CuTC and $Pd_2(dba)_3$ or $Pd(PPh_3)_4$, optionally in the presence of cesium fluoride, at a temperature ranging from room temperature to reflux.

According to conversion (conv. 23) of the process, a compound of formula (I) wherein A is —$(CH_2)_2$— can undergo dehydrogenation in the presence of an optionally supported palladium or platinum or 2,3-Dichloro-5,6-dicyano-1,4-benzoquinone (DDQ), so as to obtain the corresponding aromatic derivative of formula (I), by operating in a suitable solvent such as toluene, 1,4-dioxane, chlorobenzene, dichlorobenzene, at a temperature ranging from 90° C. to reflux, for a time varying between 2 hours to 8 hours.

According to conversion (conv.24) of the process, a compound of formula (I) wherein R4 is hydrogen and A is —$(CH_2)_2$— can be reacted with an excess of N-iodosuccinimide in DMF at room temperature so to obtain a compound of formula (XX) which is subsequently dehalogenated in presence of a palladium catalyst, for example Tetrakis (triphenylphosphine) Palladium and sodiumformiate so as to obtain the corresponding aromatic derivative of formula (I) by operating in a suitable solvent such as N,N-dimethylformamide, at a temperature ranging from 90° C. to reflux, for a time varying between 2 hours to 8 hours.

According to conversion (conv. 25) of the process, the deprotection of the nitrogen atom of a compound of formula (I) wherein R' is a protecting group, can be accomplished according to conventional methods enabling the selective hydrolysis of tert-butoxycarbonyl, benzyl, 4-methoxybenzyl, 2,4-dimethoxybenzyl, and triphenylmethyl protective groups. Preferably this reaction is run under acidic conditions, for instance in the presence of an inorganic or organic acid such as hydrochloric, trifluoroacetic or methansulfonic acid, in a suitable solvent such as DCM, 1,4-dioxane, a lower alcohol, such as methanol or ethanol, at a temperature ranging from room temperature to reflux and for a period of time ranging from about 1 hour to about 48 hours.

According to any variant of the process for preparing the compounds of formula (I), the starting material and any other reactant is known or easily prepared according to known methods.

The compound of the formula (II) wherein A is —$CH_2$— and R5 is methyl is commercially available.

The compound of the formula (II) wherein A is —$(CH_2)_2$— and R5 is methyl can be prepared as described in *J. Org. Chem.*, 1998, 63(5), 1668.

The compound of the formula (II) wherein A is —$(CH_2)_3$— and R5 is methyl can be prepared as described in *European Journal of Organic Chemistry*, 2008, 23, 3917.

The compound of the formula (II) wherein A is —$C(CH_3)_2$—$CH_2$— and R5 is methyl can be prepared as described in U.S. Pat. No. 5,750,769.

The compound of the formula (II) wherein A is —$CH_2$—$C(CH_3)_2$— and R5 is methyl can be prepared as described in *J. Org. Chem.*, 1964, 29, 801.

The compounds of the formula (III) wherein R2 is methyl, ethyl and t-buthyl are commercially available.

The compound of the formula (VII) wherein A is —$CH_2CH_2$— can be prepared as described in US2010/160318.

The compound of the formula (VIII) wherein R2 is ethoxy and R4 is methyl is commercially available.

The compounds of the formula (X), (XII), (XIII), (XIV), (XV), (XVI), (XVIa), (XVII) and (XVIIa) are either commercially available or can be prepared with known methods.

EXAMPLES

The synthetic preparation of some compounds of the formula (I) of the invention is described in the following examples.

The compounds of the present invention, as prepared according to the following examples, were also characterized by $^1$H NMR or by HPLC/MS analytical data; HPLC/MS data were collected following any one of methods 1, 2, 3 and 4.

HPLC/MS Analytic Method 1

The HPLC equipment consisted of a Waters Acquity™ UPLC system equipped with a Waters 2996 PDA detector, a Waters Acquity ELSD™ detector and Waters mod. SQD single quadrupole mass spectrometer, equipped with an electrospray (ESI) ion source. Instrument control, data acquisition and data processing were provided by Empower 2 and MassLynx 4.1 softwares.

HPLC was carried out at 45° C. at a flow rate of 0.7 mL/min using a Waters Acquity™ BEH C18, 1.7 microm, 50×2.1 mm column. Mobile phase A was 0.1% trifluoro acetic acid in $H_2O/CH_3CN$ (95:5), and mobile phase B was $H_2O/CH_3CN$ (5:95); the gradient was from 5 to 95% B in 2 minutes then hold 95% B 0.1 minutes. The injection volume was 0.8 microL. The mass spectrometer was operated in positive and in negative ion mode, the capillary voltage was set up at 3 KV ($ES^+$ and $ES^-$); cone was 30 V ($ES^+$ and $ES^-$); the source temperature was 120° C.; full scan, mass range from 100 to 800 amu was set up.

HPLC/MS Analytic Method 2

The HPLC equipment consisted of a Waters Alliance™ HT 2795 system equipped with a Waters 2996 PDA detector and Waters mod. ZQ 2000 single quadrupole mass spectrometer, equipped with an electrospray (ESI) ion source. Instrument control, data acquisition and data processing were provided by Empower 2 and MassLynx 4.1 softwares.

HPLC was carried out at 25° C. at a flow rate of 1.0 mL/min using a Phenomenex Gemini C18, 3 microm, 50×4.6 mm column. Mobile phase A was ammonium acetate 5 mM pH=5.2 buffer with $CH_3CN$ (95:5), and mobile phase B was $H_2O/CH_3CN$ (5:95); the gradient was from 10 to 90% B in 8 minutes then ramp to 100% B in 0.1 minutes. The injection volume was 10 microL. The mass spectrometer was operated in positive and in negative ion mode, the capillary voltage was set up at 3.5 kV ($ES^+$) and 2.8 kV ($ES^-$); cone voltage was 14 V ($ES^+$) and 28 V ($ES^-$); the source temperature was 120° C.; full scan, mass range from 100 to 800 amu was set up.

HPLC/MS Analytical Method 3

The HPLC equipment consisted of a Waters 2790 HPLC system equipped with a 996 Waters PDA detector and Waters mod. ZQ 2000 single quadrupole mass spectrometer, equipped with an electrospray (ESI) ion source. Instrument control, data acquisition and data processing were provided by Empower 2 and MassLynx 4.1 software.

HPLC was carried out at 25° C. at a flow rate of 1 mL/min using a RP18 Waters X Terra 3 microm (3.0×20 mm) column. Mobile phase A was ammonium hydroxide 0.05% pH=10 buffer with $CH_3CN$ (95:5), and Mobile phase B was $H_2O/CH_3CN$ (5:95); the gradient was from 10 to 90% B in 4 minutes then hold 90% B 1 minute. The injection volume was 10 microL. The mass spectrometer was operated in positive and in negative ion mode, the capillary voltage was set up at 2.5 KV; the source temperature was 120° C.; cone was 10 V; full scan, mass range from 100 to 800 amu was set up.

Several compounds of the invention of the formula (I), as prepared according to the following examples, were purified by preparative HPLC.

The operative conditions are defined below:

HPLC/MS Preparative Method 1

The HPLC equipment consisted of a Waters FractionLynx™ System equipped with a 2996 Waters PDA detector and Waters mod. ZQ 2000 single quadrupole mass spectrometer, equipped with an electrospray (ESI) ion source. Instrument control, data acquisition and data processing were provided by Empower 2 and MassLynx 4.1 software.

HPLC was carried out at 25° C. at a flow rate of 20 mL/min using a RP18 Waters X Terra 10 microm (19×250 mm) column. Mobile phase A was ammonium hydroxide 0.05% pH=10 buffer with $CH_3CN$ (95:5), and Mobile phase B was $CH_3CN$; the gradient was from 10 to 90% B in 15 minutes then hold 90% B 3 minutes. The injection volume was 200 microL.

The mass spectrometer was operated in positive and in negative ion mode, the capillary voltage was set up at 2.5 KV; the source temperature was 120° C.; cone was 10 V; full scan, mass range from 100 to 800 amu was set up.

HPLC/MS Preparative Method 2

The HPLC equipment consisted of a FractionLynx™ System equipped with a 2996 Waters PDA detector and Waters mod. ZQ 2000 single quadrupole mass spectrometer, equipped with an electrospray (ESI) ion source. Instrument control, data acquisition and data processing were provided by Empower 2 and MassLynx 4.1 software.

HPLC was carried out at 25° C. at a flow rate of 20 mL/min using a RP18 Waters X Terra 10 microm (19×250 mm) column. Mobile phase A was 0.1% TFA in $H_2O/CH_3CN$ (95:5), and mobile phase B was $CH_3CN$; the gradient was from 10 to 90% B in 15 minutes then hold 90% B 3 minutes. The injection volume was 200 microL.

The mass spectrometer was operated in positive and in negative ion mode, the capillary voltage was set up at 2.5 KV; the source temperature was 120° C.; cone was 10 V; full scan, mass range from 100 to 800 amu was set up.

MS Exact

Exact mass data ESI(+) were obtained on a Waters Q-T of Ultima directly connected with micro HPLC 1100 Agilent as previously described (M. Colombo, F. Riccardi-Sirtori, V. Rizzo, *Rapid Commun. Mass Spectrom.* 2004, 18, 511-517).

NMR $^1$H-NMR spectra were recorded at a constant temperature of 28° C. on a Varian INOVA 400 spectrometer operating at 400.50 MHz and equipped with a 5 mm z-axis PFG Indirect Detection Probe ($^1H\{^{15}N-^{31}P\}$).

Chemical shifts were referenced with respect to the residual solvent signals (DMSO-d6: 2.50 ppm for $^1$H, where not otherwise specified). Data are reported as follows: chemical shift (δ), multiplicity (s=singlet, d=doublet, t=triplet, q=quartet, br. s=broad singlet, td=triplet of doublets, dd=doublet of doublets, ddd=doublet of doublets of doublets, m=multiplet, spt=septet), coupling constants (J, Hz), and number of protons.

In the examples below as well as throughout the application, the following abbreviations have the following meanings. If not defined, the terms have their generally accepted meanings.

| | ABBREVIATIONS |
|---|---|
| AcOEt | Ethyl acetate |
| AcOH | Acetic acid |
| AcONa | Sodium acetate |
| BINAP | (2,2'-Bis(diphenylphosphino)-1,1'-binaphtalene |
| $CH_3CN$ | Acetonitrile |
| $Cs_2CO_3$ | Cesium carbonate |
| CuTC | Copper(I) thiophencarboxylate |
| CuI | Copper(I) iodide |
| DCC | N,N'-dicyclohexylcarbodiimide |
| DCM | Dichloromethane |
| DIPEA | N,N-diisopropyethylamine |
| DME | 1,2-Dimethoxyethane |
| DMF | N,N-dimethylformamide |
| DMSO | Dimethyl sulfoxide |
| EDCl | N-ethyl-N',N'-diisopropyl carbodiimide hydrochloride |
| $Et_2O$ | Diethyl ether |
| EtOH | Ethanol |
| HCl | Hydrochloric acid |
| HOBt | 1H-benzotriazol-1-ol |
| $K_2CO_3$ | Potassium carbonate |

ABBREVIATIONS

| | |
|---|---|
| $KH_2PO_4$ | Potassium dihydrogen phosphate |
| KOH | Potassium hydroxide |
| $LiN(TMS)_2$ | Lithium bis(trimethylsilyl)amide |
| LiOH | Litium hydroxide |
| MeOH | Methanol |
| $Na_2CO_3$ | Sodium carbonate |
| $Na_2S_2O_3$ | Sodium thiosulfate |
| $Na_2S_2O_5$ | Sodium metabisulphite |
| $Na_2SO_4$ | Sodium sulfate |
| NaH | Sodium hydride |
| $NaH_2PO_4$ | Sodium dihydrogen phosphate |
| $NaHCO_3$ | Sodium hydrogen carbonate |
| NaOH | Sodium hydroxide |
| $Pd(OAc)_2$ | Palladium(II) acetate |
| $Pd(PPh_3)_4$ | Tetrakis (triphenylphosphine) Palladium |
| $Pd_2(dba)_3$ | Tris(dibenzylideneacetone)dipalladium(0) |
| $PdCl_2(dppf)$ | [1,1'-bis(diphenylphosphino)ferrocene]palladium(II) chloride |
| PPA | Polyphosphoric acid |
| PyBOP | (Benzotriazol-1-yloxy)tripyrrolidinophosphonium hexafluorophosphate |
| $SOCl_2$ | Thionyl chloride |
| TBTU | O-(benzotriazol-1-yl)-N,N,N',N'-tetramethyluronium tetrafluoroborate |
| TEA | Triethylamine |
| TFA | Trifluoro acetic acid |
| TFAA | Trifluoro acetic anhydride |
| THF | Tetrahydrofurane |
| TOSMIC | Tosylmethyl isocyanide |
| Xantphos | 4,5-Bis(diphenylphosphino)-9,9-dimethylxanthene |

Preparation A (Step A)

Dimethyl(2E)-hept-2-enedioate

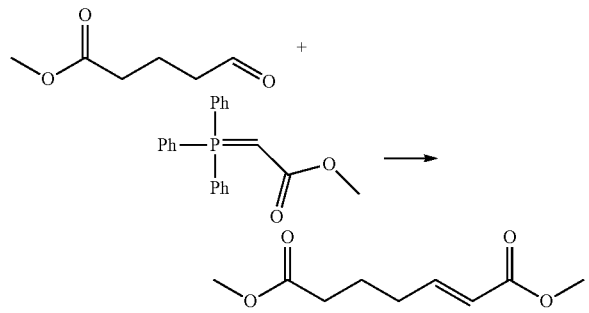

A solution of methyl 5-oxopentanoate (1.9 g, 14.6 mmol) and (carboethoxymethylene) triphenylphosphorane (5.0 g, 14.9 mmol) in toluene (50 mL) was refluxed for 8 hours. Solvent was removed under vacuo and the crude was purified by flash chromatography on silica gel (eluant: AcOEt/hexane 2/8) to give 1.32 g (48% yield) as colorless oil of the title compound.

$^1$H NMR (401 MHz, DMSO-d6) δ ppm 1.61-1.75 (m, 2H) 2.16-2.27 (m, 2H) 2.27-2.35 (m, 2H) 3.58 (s, 3H) 3.64 (s, 3H) 5.87 (dt, J=15.65, 1.56 Hz, 1H) 6.87 (dt, J=15.65, 6.94 Hz, 1H)

According to this same methodology, but employing suitable substituted derivatives, the following compounds were prepared:

dimethyl(2Z)-5,5-dimethyl hept-2-enedioate $^1$H NMR (401 MHz, DMSO-d6) δ ppm 0.98 (s, 6H) 2.24 (s, 2H) 2.63 (dt, J=7.75, 1.65 Hz, 2H)) 3.57 (m, 3H) 3.62 (s, 3H) 5.90 (dt, J=11.60, 1.65 Hz, 1H) 6.38 (dt, J=11.60, 7.75 Hz, 1H)

Dimethyl(2E)-5,5-dimethyl hept-2-enedioate $^1$H NMR (401 MHz, DMSO-d6) δ ppm 0.96 (s, 6H) 2.21 (s, 2H) 2.22-2.24 (m, 2H) 3.58 (s, 3H) 3.65 (s, 3H) 5.90 (dt, J=15.50, 5.85 Hz, 1H) 6.88 (dt, J=15.50, 7.80 Hz, 1H)

Dimethyl(2E)-hex-2-enedioate

Dimethyl(2E)-oct-2-enedioate $^1$H NMR (401 MHz, DMSO-d6) δ ppm 1.36-1.47 (m, 4H) 1.37-1.57 (m, 2H) 2.20 (qd, J=7.05, 1.60 Hz, 2H) 2.31 (t, J=7.32 Hz, 2H) 3.58 (s, 3H) 3.64 (s, 3H) 5.88 (dt, J=15.65, 1.60 Hz, 1H) 6.87 (dt, J=15.65, 7.05 Hz, 1H)

1-ethyl 8-methyl (2E)-oct-2-enedioate $^1$H NMR (401 MHz, DMSO-d6) δ ppm 1.20 (t, J=7.16 Hz, 3H) 1.36-1.46 (m, 2H) 1.47-1.57 (m, 2H) 2.20 (qd, J=7.10, 1.46 Hz, 2H) 2.31 (t, J=7.14 Hz, 2H) 3.58 (s, 3H) 4.10 (q, J=7.16 Hz, 2H) 5.86 (dt, J=15.56, 1.46 Hz, 1H) 6.86 (dt, J=15.56, 7.10 Hz, 1H)

1-ethyl 7-methyl (2E)-5,5-dimethylhept-2-enedioate $^1$H NMR (401 MHz, DMSO-d6) δ ppm 0.96 (s, 6H) 1.21 (t, J=7.08 Hz, 3H) 2.21 (s, 2H) 2.22 (dd, J=7.87, 1.30 Hz, 2H) 3.58 (s, 3H) 4.11 (q, J=7.08 Hz, 2H) 5.88 (dt, J=15.47, 1.30 Hz, 1H) 6.86 (dt, J=15.47, 7.87 Hz, 1H)

1-ethyl 7-methyl (2E)-hept-2-enedioate $^1$H NMR (401 MHz, DMSO-d6) δ ppm 1.20 (t, J=7.14 Hz, 3H) 1.68 (quin, J=7.30 Hz, 2H) 2.15-2.27 (m, 2H) 2.31 (t, J=7.30 Hz, 2H) 3.58 (s, 3H) 4.11 (q, J=7.14 Hz, 2H) 5.85 (dt, J=15.65, 1.59 Hz, 1H) 6.86 (dt, J=15.65, 6.94 Hz, 1H)

Preparation B (Step B)

Methyl 4-(4-methoxy-4-oxobutyl)-1H-pyrrole-3-carboxylate

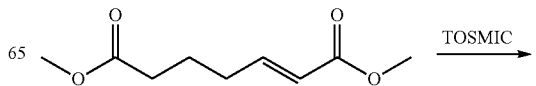

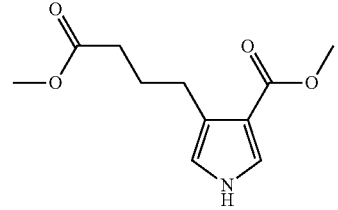

To a 1 M solution of LiN(TMS)$_2$ in THF (5.9 mL, 5.9 mmol) cooled at −78° C. under argon was added a solution of TOSMIC (1.15 g, 5.9 mmol) in THF (15 mL) dropwise. After 40 min at −78° C. a solution of dimethyl (2E)-hept-2-enedioate (1.1 g, 5.9 mmol) in THF (15 mL) at −78° C. was added slowly. The solution was stirred for 10 min, then the cold bath was removed and the reaction was allowed to warm at room temperature. THF was evaporated and the residue partioned between H$_2$O (200 mL) and DCM (200 mL). Aqueous layer was extracted with DCM and the combined organic layers anidrified on Na$_2$SO$_4$, filtered and concentrated to give a residue which was chromatographed on silica gel (eluant: AcOEt/hexane 3/7) to afford 633 mg (yield: 40%) of the title compound as white solid.

$^1$H NMR (401 MHz, DMSO-d6) δ ppm 1.77 (quin, J=7.45 Hz, 2H) 2.28 (t, J=7.45 Hz, 2H) 2.62 (t, J=7.45 Hz, 2H) 3.57 (s, 3H) 3.66 (s, 3H) 6.60 (t, J=2.20 Hz, 1H) 7.32 (dd, J=3.17, 2.20 Hz, 1H) 11.15 (br. s., 1H)

According to this same methodology, but employing suitable substituted derivatives, the following compounds were prepared:

methyl 4-(4-methoxy-2,2-dimethyl-4-oxobutyl)-1H-pyrrole-3-carboxylate $^1$H NMR (401 MHz, DMSO-d6) δ ppm 0.90 (s, 6H) 2.06 (s, 2H) 2.74 (s, 2H) 3.65 (s, 3H) 6.60 (s, 1H) 7.33 (t, J=2.56 Hz, 1H) 11.21 (br. s., 1H) 11.84 (br. s., 1H)

methyl 4-(3-methoxy-3-oxopropyl)-1H-pyrrole-3-carboxylate $^1$H NMR (401 MHz, DMSO-d6) δ ppm 2.52-2.58 (m, 2H) 2.83-2.90 (m, 2H) 3.58 (s, 3H) 3.67 (s, 3H) 6.60 (t, J=2.25 Hz, 1H) 7.33 (dd, J=3.17, 2.25 Hz, 1H) 11.16 (br. s., 1H)

methyl 4-(5-methoxy-5-oxopentyl)-1H-pyrrole-3-carboxylate

MS calculated: 240.1231; MS found: 240.1226

Ethyl 4-(4-methoxy-2,2-dimethyl-4-oxobutyl)-1H-pyrrole-3-carboxylate $^1$H NMR (401 MHz, DMSO-d6) δ ppm 0.89 (s, 6H) 1.24 (t, J=7.08 Hz, 3H) 2.15 (s, 2H) 2.73 (s, 2H) 3.56 (s, 3H) 4.12 (q, J=7.08 Hz, 2H) 6.59 (t, J=2.30 Hz, 1H) 7.31 (dd, J=3.11, 2.30 Hz, 1H) 11.21 (br. s., 1H)

Ethyl 4-(4-methoxy-4-oxobutyl)-1H-pyrrole-3-carboxylate $^1$H NMR (401 MHz, DMSO-d6) δ ppm 1.24 (t, J=7.14 Hz, 3H) 1.70-1.83 (m, 2H) 2.28 (t, J=7.51 Hz, 2H) 2.61 (t, J=7.51 Hz, 2H) 3.57 (s, 3H) 4.13 (q, J=7.14 Hz, 1H) 6.59 (t, J=2.20 Hz, 1H) 7.31 (dd, J=3.17, 2.20 Hz, 1H) 11.13 (br. s., 1H)

Preparation C (Step C)

4-[4-(methoxycarbonyl)-1H-pyrrol-3-yl]butanoic acid

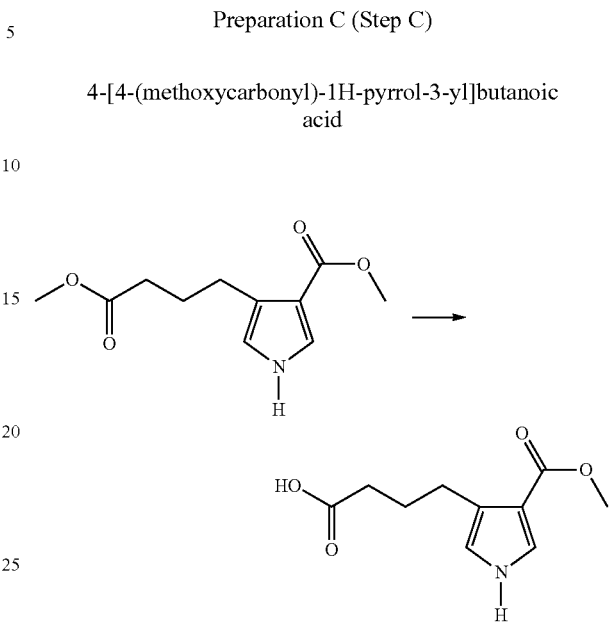

Methyl 4-(4-methoxy-4-oxobutyl)-1H-pyrrole-3-carboxylate (50 mg, 0.220 mmol) was suspended in anhydrous dioxane (2 mL) and H$_2$O (0.5 mL) and LiOH (5.3 mg, 0.220 mmol) was added. The reaction mixture was stirred at room temperature for 4 h. Reaction solution was acidified with 1N HCl and AcOEt (50 mL) and H$_2$O (20 mL) were added. Aqueous layer was extracted with AcOEt and the combined organic layers anidrified on Na$_2$SO$_4$, filtered and concentrated to give 46 mg (quantitative yield) of the title compound as a white solid.

MS calculated: 212.0918; MS found: 212.0917

$^1$H NMR (401 MHz, DMSO-d6) δ ppm 1.74 (quin, J=7.50 Hz, 2H) 2.19 (t, J=7.50 Hz, 2H) 2.62 (t, J=7.50 Hz, 2H) 3.66 (s, 3H) 6.60 (t, J=2.05 Hz, 1H) 7.32 (dd, J=3.10, 2.05 Hz, 1H) 11.14 (br. s., 1H) 11.93 (br. s., 1H)

According to this same methodology, but employing suitable substituted derivatives, the following compounds were prepared:

4-[4-(methoxycarbonyl)-1H-pyrrol-3-yl]-3,3-dimethylbutanoic acid

MS calculated: 240.1230; MS found: 240.1229

$^1$H NMR (401 MHz, DMSO-d6) δ ppm 0.90 (s, 6H) 2.06 (s, 2H) 2.74 (s, 2H) 3.65 (s, 3H) 6.60 (s, 1H) 7.33 (t, J=2.56 Hz, 1H) 11.21 (br. s., 1H) 11.84 (br. s., 1H)

3-[4-(methoxycarbonyl)-1H-pyrrol-3-yl]propanoic acid $^1$H NMR (401 MHz, DMSO-d6) δ ppm 2.45 (t, J=7.50 Hz, 2H) 2.84 (t, J=7.50 Hz, 2H) 3.67 (s, 3H) 6.60 (t, J=2.20 Hz, 1H) 7.33 (dd, J=3.17, 2.20 Hz, 1H) 11.15 (br. s., 1H) 11.96 (br. s., 1H)

5-[4-(methoxycarbonyl)-1H-pyrrol-3-yl]pentanoic acid

MS calculated: 248.0893; MS found: 248.0896

$^1$H NMR (401 MHz, DMSO-d6) δ ppm 1.45-1.56 (m, 4H) 2.20 (t, J=6.90 Hz, 2H) 2.60 (t, J=6.90 Hz, 2H) 3.66 (s, 3H) 6.59 (t, J=2.20 Hz, 1H) 7.31 (dd, J=3.17, 2.20 Hz, 1H) 11.11 (br. s., 1H) 11.92 (br. s., 1H) 4-[4-(ethoxycarbonyl)-1H-pyrrol-3-yl]-3,3-dimethylbutanoic acid

4-[4-(ethoxycarbonyl)-1H-pyrrol-3-yl]butanoic acid $^1$H NMR (401 MHz, DMSO-d6) δ ppm 1.24 (t, J=7.08 Hz, 3H) 1.74 (quin, J=7.50 Hz, 2H) 2.19 (t, J=7.50 Hz, 2H) 2.61 (t, J=7.50 Hz, 2H) 4.14 (q, J=7.08 Hz, 2H) 6.59 (t, J=2.20 Hz, 1H) 7.31 (dd, J=3.17, 2.20 Hz, 1H) 11.12 (br. s., 1H) 11.92 (br. s., 1H)

Preparation D (Step Ca)

4-[4-(ethoxycarbonyl)-5-methyl-1H-pyrrol-3-yl]butanoic acid

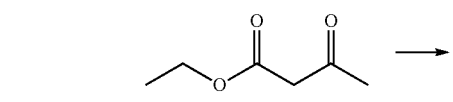

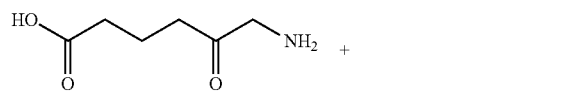

6-amino-5-oxohexanoic acid hydrochloride (9.73 g, 49.8 mmol) was dissolved in H$_2$O (35 mL), and ethyl acetoacetate (5.51 g, 42.34 mmol) and AcONa (20.3 g, 14.95 mmol) were added to the above-mentioned solution. The reaction solution was refluxed for 1 h, cooled to room temperature and 0.5N HCl was added until a pH of about 5 was reached. The combined organic layers were anidrified on Na$_2$SO$_4$, filtered and concentrated to give 7.15 g (yield: 60%) of the title compound as brown solid.

MS calculated: 240.1231; MS found: 240.1225

$^1$H NMR (401 MHz, DMSO-d6) δ ppm 1.25 (t, J=7.14 Hz, 3H) 1.71 (quin, J=7.50 Hz, 2H) 2.18 (t, J=7.50 Hz, 2H) 2.36 (s, 3H) 2.56 (t, J=7.50 Hz, 2H) 4.13 (q, J=7.14 Hz, 2H) 6.39 (d, J=2.32 Hz, 1H) 10.91 (br. s., 1H) 11.90 (br. s., 1H)

Preparation E (Step D)

Methyl 7-oxo-4,5,6,7-tetrahydro-1H-indole-3-carboxylate

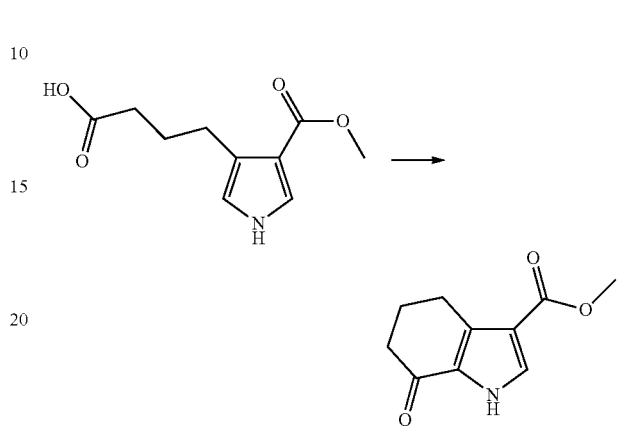

4-[4-(methoxycarbonyl)-1H-pyrrol-3-yl]butanoic acid (500 mg, 2.36 mmol) was dissolved in TFA (3 mL). TFAA (0.329 mL, 2.36 mmol) was added and the reaction was stirred at room temperature for 1 h. Organic solvent was evaporated to dryness and the residue suspended in Et$_2$O (15 mL) and filtrated to give 320 mg (yield: 64%) of the title compound as a light yellow solid.

$^1$H NMR (401 MHz, DMSO-d6) δ ppm 2.02 (quin, J=6.30 Hz, 2H) 2.40 (t, J=6.30 Hz, 2H) 2.91 (t, J=6.30 Hz, 2H) 3.72 (s, 3H) 7.58 (d, J=3.42 Hz, 1H) 12.38 (br. s., 1H)

According to this same methodology, but employing suitable substituted derivatives, the following compounds were prepared:

methyl 5,5-dimethyl-7-oxo-4,5,6,7-tetrahydro-1H-indole-3-carboxylate $^1$H NMR (401 MHz, DMSO-d6) δ ppm 0.97 (s, 6H) 2.30 (s, 2H) 2.82 (s, 2H) 3.72 (s, 3H) 7.60 (d, J=3.42 Hz, 1H) 12.38 (br. s., 1H)

methyl 6-oxo-1,4,5,6-tetrahydrocyclopenta[b]pyrrole-3-carboxylate $^1$H NMR (401 MHz, DMSO-d6) δ ppm 2.71-2.80 (m, 2H) 2.87-2.93 (m, 2H) 3.74 (s, 3H) 7.85 (s, 1H) 12.37 (br. s., 1H)

methyl 8-oxo-1,4,5,6,7,8-hexahydrocyclohepta[b]pyrrole-3-carboxylate $^1$H NMR (401 MHz, DMSO-d6) δ ppm 1.70-1.80 (m, 2H) 1.81-1.89 (m, 2H) 2.59-2.65 (m, 2H) 3.06-3.15 (m, 2H) 3.70 (s, 3H) 7.51 (d, J=3.66 Hz, 1H) 12.01 (br. s., 1H)

Ethyl 5,5-di methyl-7-oxo-4,5,6,7-tetrahydro-1H-indole-3-carboxylate $^1$H NMR (401 MHz, DMSO-d6) δ ppm 1.03 (s, 6H) 1.26 (t, J=7.08 Hz, 3H) 2.30 (s, 2H) 2.83 (s, 2H) 4.19 (q, J=7.08 Hz, 2H) 7.57 (d, J=3.42 Hz, 1H) 12.36 (br. s., 1H)

Ethyl
7-oxo-4,5,6,7-tetrahydro-1H-indole-3-carboxylate $^1$H NMR (401 MHz, DMSO-d6) δ ppm 1.24 (t, J=7.08 Hz, 3H) 1.74 (quin, J=7.50 Hz, 2H) 2.19 (t, J=7.50 Hz, 2H) 2.61 (t, J=7.50 Hz, 2H) 4.14 (q, J=7.08 Hz, 2H) 6.59 (t, J=2.20 Hz, 1H) 7.31 (dd, J=3.17, 2.20 Hz, 1H) 11.12 (br. s., 1H) 11.92 (br. s., 1H)

Ethyl 2-methyl-7-oxo-4,5,6,7-tetrahydro-1H-indole-3-carboxylate

MS calculated: 222.1125; MS found: 222.1136
$^1$H NMR (401 MHz, DMSO-d6) δ ppm 1.27 (t, J=7.08 Hz, 3H) 1.99 (quin, J=6.30 Hz, 2H) 2.36 (t, J=6.30 Hz, 2H) 2.43 (s, 3H) 2.87 (t, J=6.30 Hz, 2H) 4.18 (q, J=7.08 Hz, 2H) 12.15 (br. s., 1H)

Preparation F (Step E)

Methyl 1-methyl-7-oxo-4,5,6,7-tetrahydro-1H-indole-3-carboxylate

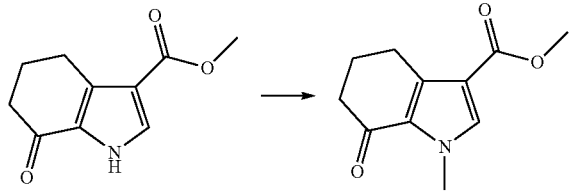

To a solution of methyl 7-oxo-4,5,6,7-tetrahydro-1H-indole-3-carboxylate (300 mg, 1.55 mmol) in dry DMF (5 mL) $K_2CO_3$ (429 mg, 3.10 mmol) and methyl iodide (0.193 mL, 3.10 mmol) were added. The reaction was stirred at room temperature for 3 h, then $H_2O$ was added (100 mL) and the product extracted with DCM (3×30 mL). The organic fractions were dried over $Na_2SO_4$, filtered, and concentrated in vacuo to give 305 mg (yield: 95%) as light yellow solid.

$^1$H NMR (401 MHz, DMSO-d6) δ ppm 1.95-2.03 (m, 2H) 2.40 (t, J=6.15 Hz, 2H) 2.91 (t, J=6.04 Hz, 2H) 3.72 (s, 3H) 3.85 (s, 3H) 7.71 (s, 1H)

According to this same methodology, but employing suitable substituted derivatives, the following compounds were prepared:

methyl 1-methyl-6-oxo-1,4,5,6-tetrahydrocyclopenta[b]pyrrole-3-carboxylate

MS calculated: 194.0812; MS found: 194.0810
$^1$H NMR (401 MHz, DMSO-d6) δ ppm 2.72-2.81 (m, 2H) 2.83-2.92 (m, 2H) 3.73 (s, 3H) 3.74 (s, 3H) 7.81-7.91 (m, 1H)

methyl 1,5,5-trimethyl-7-oxo-4,5,6,7-tetrahydro-1H-indole-3-carboxylate

MS calculated: 236.1281; MS found: 236.1281
$^1$H NMR (401 MHz, DMSO-d6) δ ppm 1.02 (s, 6H) 2.30 (s, 2H) 2.83 (s, 2H) 3.72 (s, 3H) 3.85 (s, 3H) 7.72 (s, 1H)

methyl 1-methyl-8-oxo-1,4,5,6,7,8-hexahydrocyclohepta[b]pyrrole-3-carboxylate $^1$H NMR (401 MHz, DMSO-d6) δ ppm 1.60-1.74 (m, 4H) 2.53-2.62 (m, 2H) 3.13 (t, J=6.04 Hz, 2H) 3.68 (s, 3H) 3.78 (s, 3H) 7.66 (s, 1H)

Ethyl 1,5,5-trimethyl-7-oxo-4,5,6,7-tetrahydro-1H-indole-3-carboxylate

MS calculated: 250.1438; MS found: 250.1444
$^1$H NMR (401 MHz, DMSO-d6) δ ppm 1.02 (s, 6H) 1.26 (t, J=7.08 Hz, 3H) 2.30 (s, 2H) 2.83 (s, 2H) 3.85 (s, 3H) 4.19 (q, J=7.08 Hz, 2H) 7.70 (s, 1H)

Ethyl 1-methyl-7-oxo-4,5,6,7-tetrahydro-1H-indole-3-carboxylate

MS calculated: 222.1125; MS found: 222.1134
$^1$H NMR (401 MHz, DMSO-d6) δ ppm 1.26 (t, J=7.16 Hz, 3H) 1.93-2.05 (m, 2H) 2.40 (t, J=6.10 Hz, 2H) 2.92 (t, J=6.10 Hz, 2H) 3.86 (s, 3H) 4.19 (q, J=7.16 Hz, 2H) 7.70 (s, 1H)

Ethyl 1-(methoxymethyl)-2-methyl-7-oxo-4,5,6,7-tetrahydro-1H-indole-3-carboxylate MS calculated: 266.1387; MS found: 266.1376
$^1$H NMR (401 MHz, DMSO-d6) δ ppm 1.29 (t, J=7.12 Hz, 3H) 1.92-2.03 (m, 2H) 2.39-2.45 (m, 2H) 2.53 (s, 3H) 2.93 (t, J=6.16 Hz, 2H) 3.19 (s, 3H) 4.22 (q, J=7.12 Hz, 2H) 5.75 (s, 2H)

Ethyl 1,2-dimethyl-7-oxo-4,5,6,7-tetrahydro-1H-indole-3-carboxylate

MS calculated: 236.1281; MS found: 236.1283
$^1$H NMR (401 MHz, DMSO-d6) δ ppm 1.28 (t, J=7.08 Hz, 3H) 1.95 (quin, J=6.25 Hz, 2H) 2.38 (t, J=6.25 Hz, 2H) 2.48 (s, 3H) 2.90 (t, J=6.25 Hz, 2H) 3.83 (s, 3H) 4.20 (q, J=7.08 Hz, 2H)

Preparation G (Step F)

Methyl (6E)-6-[(dimethylamino)methylidene]-1-methyl-7-oxo-4,5,6,7-tetrahydro-1H-indole-3-carboxylate

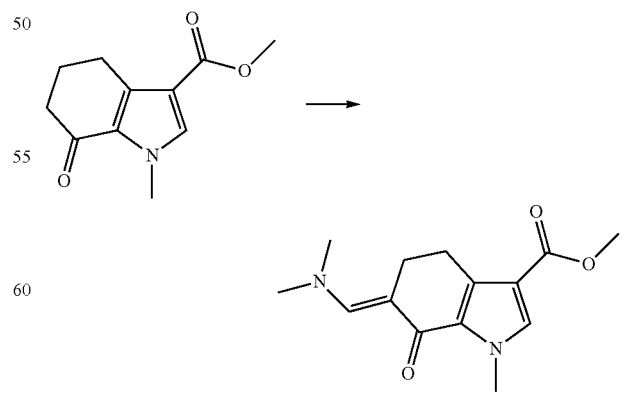

Methyl 1-methyl-7-oxo-4,5,6,7-tetrahydro-1H-indole-3-carboxylate (288 mg, 1.39 mmol) was treated with tris(dimethylamino)methane (2.4 mL, 13.9 mmol) and the reaction mixture was stirred at 90° C. for 10 h. Volatiles were removed under reduced pressure and the residue used without further purification.

According to this same methodology, but employing suitable substituted derivatives, the following compounds were prepared:

methyl (6E)-5,5-dimethyl-6-[(methylamino)methylidene]-7-oxo-4,5,6,7-tetrahydro-1H-indole-3-carboxylate MS calculated: 263.1390; MS found: 263.1384

$^1$H NMR (401 MHz, DMSO-d6) δ ppm 1.15 (s, 6H) 2.74 (s, 2H) 2.97 (d, J=5.05 Hz, 3H) 3.64-3.73 (m, 3H) 6.91 (d, J=12.30 Hz, 1H) 7.40 (d, J=3.30 Hz, 1H) 9.58 (dd, J=12.30, 5.05 Hz, 1H) 12.00 (br. s., 1H)

methyl (7E)-7-[(dimethylamino)methylidene]-1-methyl-8-oxo-1,4,5,6,7,8-hexahydrocyclohepta[b]pyrrole-3-carboxylate MS calculated: 277.1547; MS found: 277.1554

$^1$H NMR (401 MHz, DMSO-d6) δ ppm 1.76 (quin, J=6.80 Hz, 2H) 2.32 (t, J=6.80 Hz, 2H) 2.89 (t, J=6.80 Hz, 2H) 3.07 (s, 6H) 3.69 (s, 3H) 3.74 (s, 3H) 7.36 (s, 1H) 7.51 (s, 1H)

Ethyl (6E)-6-[(dimethylamino)methylidene]-1-methyl-7-oxo-4,5,6,7-tetrahydro-1H-indole-3-carboxylate $^1$H NMR (401 MHz, DMSO-d6) δ ppm 1.25 (t, J=7.14 Hz, 3H) 2.76-2.89 (m, 4H) 3.05 (s, 6H) 3.87 (s, 3H) 4.17 (q, J=7.14 Hz, 2H) 7.29 (s, 1H) 7.53 (s, 1H)

Ethyl (6E)-6-[(dimethylamino)methylidene]-2-methyl-7-oxo-4,5,6,7-tetrahydro-1H-indole-3-carboxylate MS calculated: 277.1547; MS found: 277.1544

$^1$H NMR (401 MHz, DMSO-d6) δ ppm 1.26 (t, J=7.08 Hz, 3H) 2.41 (s, 3H) 2.77-2.83 (m, 2H) 2.85-2.91 (m, 2H) 3.04 (s, 6H) 4.16 (q, J=7.08 Hz, 2H) 7.26 (s, 1H) 11.86 (br. s., 1H)

Ethyl (6E)-6-[(dimethylamino)methylidene]-1-(methoxymethyl)-2-methyl-7-oxo-4,5,6,7-tetrahydro-1H-indole-3-carboxylate

Methyl (6E)-6-[(dimethylamino)methylidene]-7-oxo-4,5,6,7-tetrahydro-1H-indole-3-carboxylate LC/MS (254 nm) HPLC method 2 Rt 4.5 min.

$^1$H NMR (400 MHz, DMSO-d6) δ 2.80-2.84 (m, 2H) 2.88-2.92 (m, 2H) 3.06 (s, 6H) 3.70 (s, 3H) 7.31 (s, 1H) 7.41 (d, J=2.75 Hz, 1H) 12.06 (br. s., 1H).

methyl (6E)-1-[1-(tert-butoxycarbonyl)piperidin-4-yl]-6-[(dimethylamino)methylidene]-7-oxo-4,5,6,7-tetrahydro-1H-indole-3-carboxylate Preparation H (Step E)

methyl 1-[1-(tert-butoxycarbonyl)piperidin-4-yl]-7-oxo-4,5,6,7-tetrahydro-1H-indole-3-carboxylate

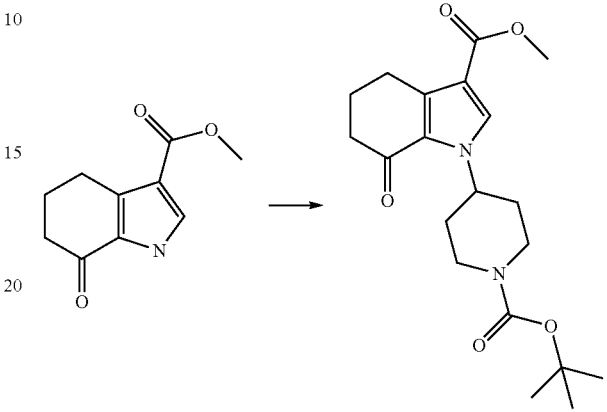

To a mixture of methyl 7-oxo-4,5,6,7-tetrahydro-1H-indole-3-carboxylate (100 mg 0.52 mmol), tert-butyl-4-hydroxypiperidine-1-carboxylate (105 mg, 0.52 mmol), and triphenylphosphine (136 mg, 0.52 mmol), in anhydrous THF (5 mL) at room temperature, was added di tert-butyl-diazadicarboxylate (DTAD) (120 mg, 0.52 mmol). The mixture was stirred at room temperature for 8 h. HPLC/MS suggested 40% conversion and 60% SM remained. Reagents were added, triphenylphosphine (136 mg, 0.52 mmol) and DTAD (120 mg, 0.52 mmol), the mixture was stirred for 4 hours. HPLC/MS showed 80% conversion and 20% SM remained. Reagents were re-added TPP (136 mg, 0.52 mmol) and DTAD (120 mg, 0.526 mmol) and the solution was stirred for additional 4 hours. The volatiles were removed in vacuo, the crude solid was purified by flash chromatography on silica gel (hexane/EtOAc 7/3) to afford 140 mg (70% yield) of the title compound as a white solid.

Example 1 (Step G)

Methyl 2-[(4-bromo-2-methoxyphenyl)amino]-9-methyl-6,9-dihydro-5H-pyrrolo[3,2-h]quinazoline-7-carboxylate [(I), R1=4-bromo-2-methoxyphenyl, X=—NH—, R2=—O-methyl, R3=methyl, R4=H, A=—CH$_2$CH$_2$—]

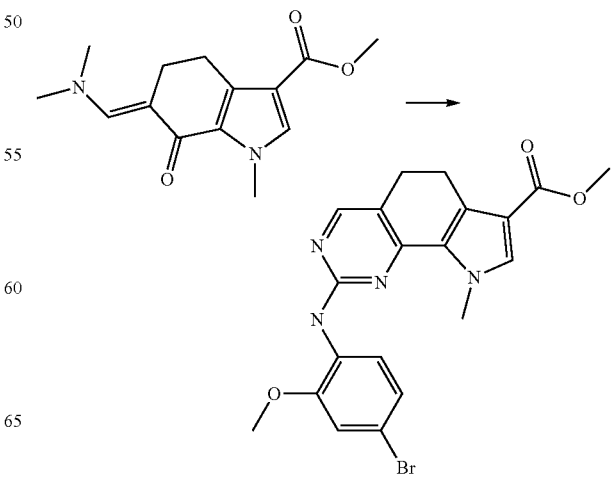

To a suspension of methyl (6E)-6-[(dimethylamino)methylidene]-1-methyl-7-oxo-4,5,6,7-tetrahydro-1H-indole-3-carboxylate (365 mg, 1.39 mmol) in DMF (5 mL) N-(4-bromo-2-methoxy-phenyl)-guanidine (340 mg, 1.39 mmol) was added. The mixture was stirred at 120° C. for 3 hours. The resulting mixture was cooled at room temperature and evaporated to dryness. The crude solid was purified by flash chromatography on silica gel (eluant: AcOEt/hexane 4/6) to afford 306 mg (yield: 50%) of the title compound as a light orange solid.

MS calculated: 443.0714; MS found: 443.0704

$^1$H NMR (401 MHz, DMSO-d6) δ ppm 2.76 (t, J=7.81 Hz, 2H) 2.93 (t, J=7.81 Hz, 2H) 3.72 (s, 3H) 3.88 (s, 3H) 4.03 (s, 3H) 7.12 (dd, J=8.60, 2.20 Hz, 1H) 7.20 (d, J=2.20 Hz, 1H) 7.65 (d, J=0.49 Hz, 1H) 7.91 (s, 1H) 8.07 (d, J=8.60 Hz, 1H) 8.21 (s, 1H)

According to this same methodology, but employing suitable substituted derivatives, the following compounds were prepared:

Ethyl 2-[(4-bromo-2-methoxyphenyl)amino]-8-methyl-6,9-dihydro-5H-pyrrolo[3,2-h]quinazoline-7-carboxylate [(I), R1=4-bromo-2-methoxyphenyl, X=—NH—, R2=—O-ethyl, R3=H, R4=methyl, A=—CH$_2$CH$_2$—]

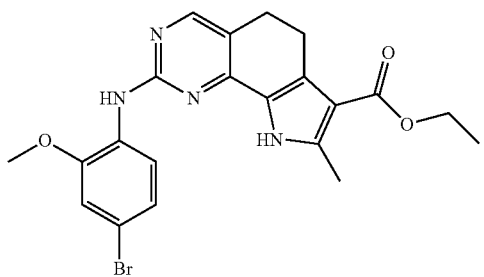 [SMILES: CCOC(=O)c1c(C)[nH]c2c1CCc1cnc(Nc3ccc(Br)cc3OC)nc1-2]

MS calculated: 457.087; MS found: 457.0868

$^1$H NMR (401 MHz, DMSO-d6) δ ppm 1.28 (t, J=7.08 Hz, 3H) 2.51 (br. s., 3H) 2.75-2.83 (m, 2H) 2.91-2.98 (m, 2H) 3.92 (s, 3H) 4.19 (q, J=7.08 Hz, 2H) 7.13 (dd, J=8.65, 2.20 Hz, 1H) 7.20 (d, J=2.20 Hz, 1H) 7.60 (s, 1H) 8.17 (s, 1H) 8.50 (d, J=8.65 Hz, 1H) 12.07 (s, 1H)

Ethyl 9-methyl-2-{[4-(4-methylpiperazin-1-yl)phenyl]amino}-6,9-dihydro-5H-pyrrolo[3,2-h]quinazoline-7-carboxylate [(I), R1=4-(4-methylpiperazin-1-yl)phenyl, X=—NH—, R2=—O-ethyl, R3=methyl, R4=H, A=—CH$_2$CH$_2$—]

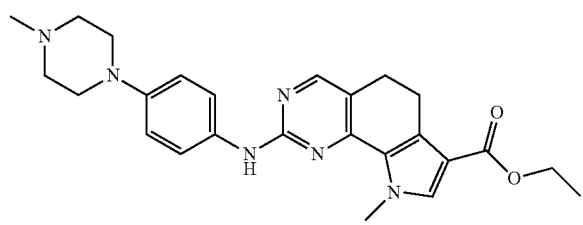 [SMILES: CCOC(=O)c1cn(C)c2c1CCc1cnc(Nc3ccc(N4CCN(C)CC4)cc3)nc1-2]

MS calculated: 447.2503; MS found: 447.2485

$^1$H NMR (401 MHz, DMSO-d6) δ ppm 1.27 (t, J=7.08 Hz, 3H) 2.22 (s, 3H) 2.42-2.47 (m, 4H) 2.70-2.77 (m, 2H) 2.89-2.95 (m, 2H) 3.02-3.09 (m, 4H) 4.08 (s, 3H) 4.19 (q, J=7.08 Hz, 2H) 6.84-6.90 (m, 2H) 7.45-7.53 (m, 2H) 7.61 (s, 1H) 8.14 (s, 1H) 8.97 (s, 1H)

Ethyl 2-[(4-bromo-2-methoxyphenyl)amino]-9-methyl-6,9-dihydro-5H-pyrrolo[3,2-h]quinazoline-7-carboxylate [(I),R1=4-bromo-2-methoxyphenyl, X=—NH—, R2=—O-ethyl, R3=methyl, R4=H, A=—CH$_2$CH$_2$—]

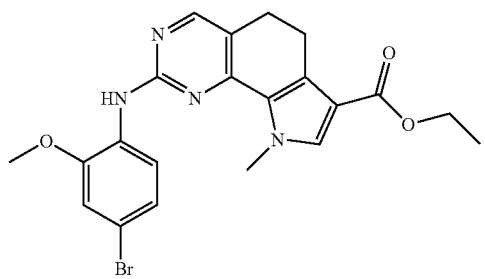 [SMILES: CCOC(=O)c1cn(C)c2c1CCc1cnc(Nc3ccc(Br)cc3OC)nc1-2]

MS calculated: 457.0870; MS found: 457.0876

$^1$H NMR (401 MHz, DMSO-d6) δ ppm 1.27 (t, J=7.08 Hz, 3H) 2.71-2.83 (m, 2H) 2.89-2.98 (m, 2H) 3.88 (s, 3H) 4.03 (s, 3H) 4.20 (q, J=7.08 Hz, 2H) 7.12 (dd, J=8.60, 2.20 Hz, 1H) 7.20 (d, J=2.20 Hz, 1H) 7.63 (s, 1H) 7.92 (s, 1H) 8.06 (d, J=8.60 Hz, 1H) 8.20 (s, 1H)

methyl 2-[(4-bromo-2-methoxyphenyl)amino]-10-methyl-5,6,7,10-tetrahydropyrrolo[3',2':6,7]cyclohepta[1,2-d]pyrimidine-8-carboxylate [(I), R1=4-bromo-2-methoxyphenyl, X=—NH—, R2=—O-methyl, R3=methyl, R4=H, A=—(CH$_2$)$_3$—]

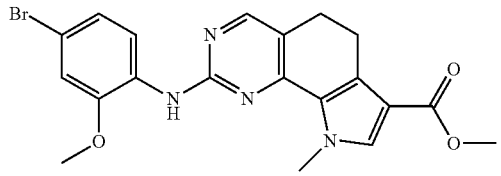 [SMILES: COC(=O)c1cn(C)c2c1CCc1cnc(Nc3ccc(Br)cc3OC)nc1-2]

MS calculated: 457.0870; MS found: 457.0851

$^1$H NMR (401 MHz, DMSO-d6) δ ppm 1.92-2.07 (m, 2H) 2.91 (t, J=7.08 Hz, 2H) 3.71 (s, 3H) 3.85 (s, 3H) 3.86 (s, 3H) 7.13 (dd, J=8.61, 2.20 Hz, 1H) 7.20 (d, J=2.20 Hz, 1H) 7.66 (s, 1H) 7.93-8.08 (m, 2H) 8.30 (s, 1H)

Ethyl 2-amino-8-methyl-6,9-dihydro-5H-pyrrolo[3,2-h]quinazoline-7-carboxylate [(I), R1=H, X=—NH—, R2=—O-ethyl, R3=H, R4=methyl, A=—CH$_2$CH$_2$—]

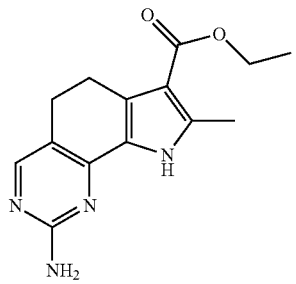 [SMILES: CCOC(=O)c1c(C)[nH]c2c1CCc1cnc(N)nc1-2]

Ethyl 9-(methoxymethyl)-2-{[2-methoxy-4-(4-methylpiperazin-1-yl)phenyl]amino}-8-methyl-6,9-dihydro-5H-pyrrolo[3,2-h]quinazoline-7-carboxylate [(I), R1=2-methoxy-4-(4-methylpiperazin-1-yl)phenyl, X=—NH—, R2=—O-ethyl, R3=methoxymethyl, R4=methyl, A=—CH$_2$CH$_2$—]

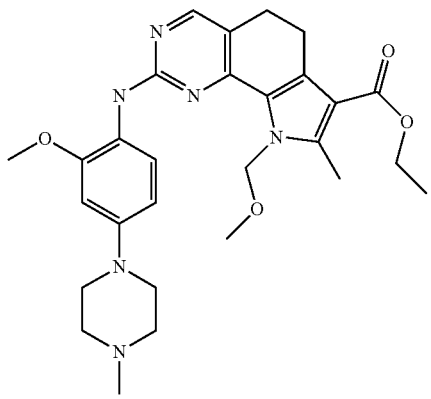 [SMILES: CCOC(=O)c1c2c(n(COC)c1C)-c1nc(Nc3ccc(N4CCN(C)CC4)cc3OC)ncc1CC2]

Example 2 (Conv. 3)

2-[(4-bromo-2-methoxyphenyl)amino]-9-methyl-6,9-dihydro-5H-pyrrolo[3,2-h]quinazoline-7-carboxylic acid [(I), R1=4-bromo-2-methoxyphenyl, X=—NH—, R2=—OH, R3=methyl, R4=H, A=—CH$_2$CH$_2$—]

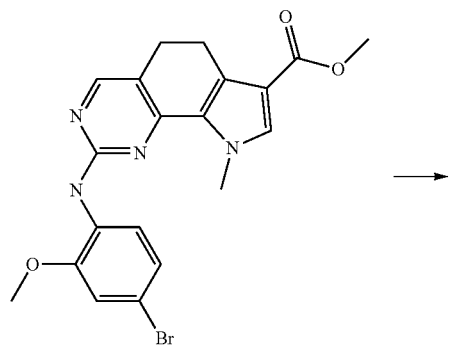

→

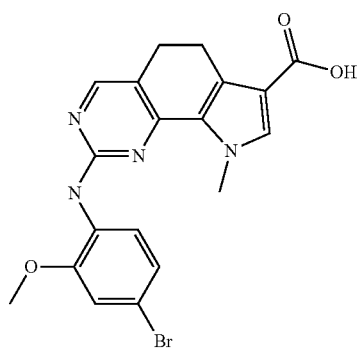

Methyl 2-[(4-bromo-2-methoxyphenyl)amino]-9-methyl-6,9-dihydro-5H-pyrrolo[3,2-h]quinazoline-7-carboxylate (300 mg, 0.68 mmol) was suspended in dioxane (10 mL) and treated with a 2 N solution of NaOH (5.1 mL, 10.2 mmol) at reflux temperature for 3 h. H$_2$O (50 mL) was added and the solution was acidified with HCl 2N. The resulting precipitate was collected by filtration to give 211 mg (yield 72%) of the title compound as a white solid.

MS calculated: 429.0557; MS found: 429.0566

$^1$H NMR (401 MHz, DMSO-d6) δ ppm 2.73 (t, J=7.93 Hz, 2H) 2.93 (t, J=7.93 Hz, 2H) 3.88 (s, 3H) 4.03 (s, 3H) 7.12 (dd, J=8.67, 2.20 Hz, 1H) 7.20 (d, J=2.20 Hz, 1H) 7.57 (s, 1H) 7.88 (s, 1H) 8.08 (d, J=8.67 Hz, 1H) 8.20 (s, 1H) 12.00 (br. s., 1H)

According to this same methodology, but employing suitable substituted derivatives, the following compounds were prepared:

2-[(4-bromo-2-methoxyphenyl)amino]-8,9-dimethyl-6,9-dihydro-5H-pyrrolo[3,2-h]quinazoline-7-carboxylic acid [(I), R1=4-bromo-2-methoxyphenyl, X=—NH—, R2=—OH, R3=methyl, R4=methyl, A=—CH$_2$CH$_2$—]

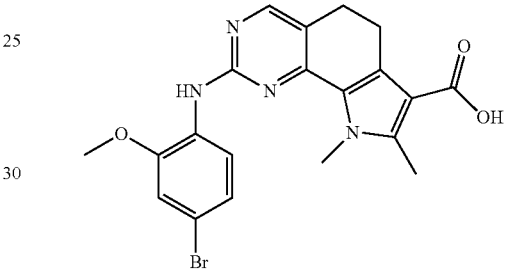

MS calculated: 443.0714; MS found: 443.0703

$^1$H NMR (401 MHz, DMSO-d6) δ ppm 2.53 (s, 3H) 2.67-2.74 (m, 2H) 2.87-2.97 (m, 2H) 3.88 (s, 3H) 4.00 (s, 3H) 7.12 (dd, J=8.54, 2.20 Hz, 1H) 7.20 (d, J=2.20 Hz, 1H) 7.86 (s, 1H) 8.09 (d, J=8.54 Hz, 1H) 8.16 (s, 1H) 12.02 (br. s., 1H)

2-amino-9-[1-(tert-butoxycarbonyl)piperidin-4-yl]-6,9-dihydro-5H-pyrrolo[3,2-h]quinazoline-7-carboxylic acid [(I), R1=H, X=—NH—, R2=—OH, R3=1-(tert-butoxycarbonyl)piperidin-4-yl, R4=H, A=—CH$_2$CH$_2$—]

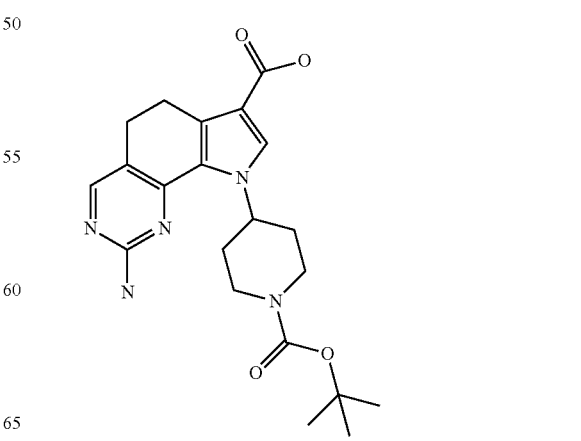

Example 3 (Conv. 4)

2-[(4-bromo-2-methoxyphenyl)amino]-N-(2,6-diethylphenyl)-9-methyl-6,9-dihydro-5H-pyrrolo[3,2-h]quinazoline-7-carboxamide[(I), R1=4-bromo-2-methoxyphenyl, X=—NH—, R2=—N-(2,6-diethylphenyl), R3=methyl, R4=H, A=—CH$_2$CH$_2$—] (cmpd 8)

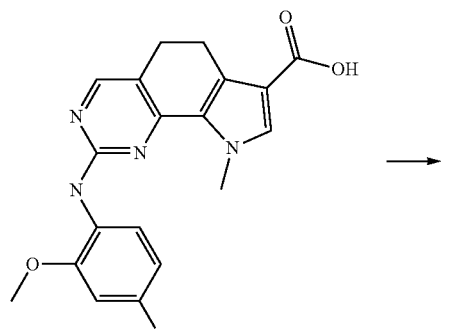

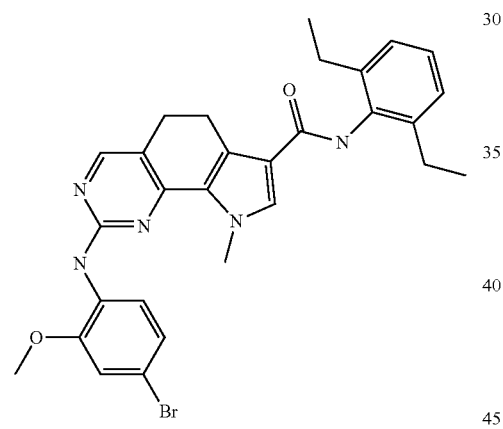

2-[(4-bromo-2-methoxyphenyl)amino]-9-methyl-6,9-dihydro-5H-pyrrolo[3,2-h]quinazoline-7-carboxylic acid (206 mg, 0.48 mmol) was suspended in dry THF (10 mL) and SOCl$_2$ (0.7 mL, 9.6 mmol) was added under argon. The reaction mixture was refluxed for 2 h then all volatiles were removed under reduced pressure. The crude residue was dissolved in dry DCM (10 mL) then DIPEA (0.43 mL, 2.4 mmol) and 2,6-diethylaniline (143 mg, 0.96 mmol) were added and the reaction mixture was refluxed for 2 h. DCM (100 mL) was added and the organic phase extracted with H$_2$O (3×25 mL). The organic layer was dried over anhydrous Na$_2$SO$_4$ and the solvent evaporated to dryness to give 190 mg (yield: 70%) of the title compound as a pale yellow solid.

MS calculated: 560.1656; MS found: 560.1655

$^1$H NMR (401 MHz, DMSO-d6) δ ppm 1.11 (t, J=7.57 Hz, 6H) 2.55 (q, J=7.57 Hz, 4H) 2.72-2.79 (m, 2H) 2.95-3.02 (m, 2H) 3.89 (s, 4H) 4.08 (s, 3H) 7.08-7.16 (m, 3H) 7.16-7.24 (m, 2H) 7.74 (s, 1H) 7.88 (s, 1H) 8.12 (d, J=8.70 Hz, 1H) 8.20 (s, 1H) 9.05 (s, 1H)

According to this same methodology, but employing suitable substituted derivatives, the following compounds were prepared:

2-[(4-bromo-2-methoxyphenyl)amino]-8,9-dimethyl-6,9-dihydro-5H-pyrrolo[3,2-h]quinazoline-7-carboxamide [(I), R1=4-bromo-2-methoxyphenyl, X=—NH—, R2=—NH$_2$, R3=methyl, R4=methyl, A=—CH$_2$CH$_2$—]

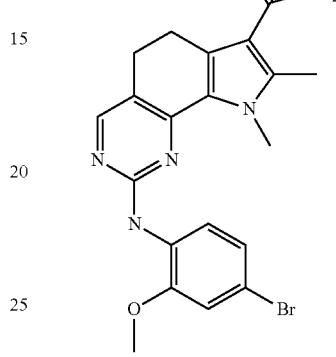

Example 4 (Conv. 5)

2-[(4-bromo-2-methoxyphenyl)amino]-N-(2,6-diethylphenyl)-8,9-dimethyl-6,9-dihydro-5H-pyrrolo[3,2-h]quinazoline-7-carboxamide [(I), R1=4-bromo-2-methoxyphenyl, X=—NH—, R2=—N-(2,6-diethylphenyl), R3=methyl, R4=methyl, A=—CH$_2$CH$_2$—] (cmpd 2)

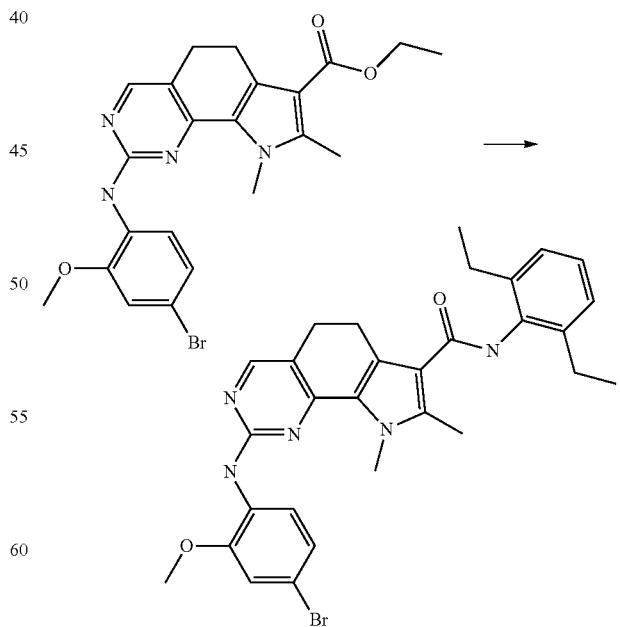

To a solution of 2,6-diethylaniline (300 mg, 2.01 mmol) in dry THF (10 mL) under argon, 1M in THF solution of LiN(TMS)$_2$ (4.02 mL, 4.02 mmol) at 0° C. was added dropwise.

The mixture was stirred at 0° C. for 10 minutes then ethyl 2-[(4-bromo-2-methoxyphenyl)amino]-8,9-dimethyl-6,9-dihydro-5H-pyrrolo[3,2-h]quinazoline-7-carboxylate (0.315 g, 0.67 mmol) in dry THF (10 mL) at 0° C. was added dropwise. Ice bath was removed and the mixture was stirred at room temperature for 1 hour. H$_2$O (20 mL) was added and the mixture was extracted with AcOEt (2×30 mL). The organic layer was dried over anhydrous Na$_2$SO$_4$ and the solvent evaporated to dryness. The crude solid was purified by flash chromatography on silica gel (eluant: AcOEt/cyclohexane 1/1) to afford 355 mg (92% yield) of the title compound as a light yellow solid.

MS calculated: 574.1812; MS found: 574.1818
$^1$H NMR (401 MHz, DMSO-d6) δ ppm 1.14 (t, J=7.57 Hz, 6H) 2.44 (s, 3H) 2.58 (q, J=7.57 Hz, 4H) 2.71-2.81 (m, 2H) 2.85-2.94 (m, 2H) 3.89 (s, 3H) 4.02 (s, 3H) 7.10-7.16 (m, 3H) 7.18-7.23 (m, 2H) 7.85 (s, 1H) 8.13 (d, J=8.67 Hz, 1H) 8.16 (s, 1H) 8.84 (s, 1H)

According to this same methodology, but employing suitable substituted derivatives, the following compounds were prepared:

N-(2,6-diethylphenyl)-9-(methoxymethyl)-2-{[2-methoxy-4-(4-methylpiperazin-1-yl)phenyl]amino}-8-methyl-6,9-dihydro-5H-pyrrolo[3,2-h]quinazoline-7-carboxamide [(I), R1=2-methoxy-4-(4-methylpiperazin-1-yl)phenyl, X=—NH—, R2=—N-(2,6-diethylphenyl), R3=methoxymethyl, R4=methyl, A=—CH$_2$CH$_2$—] (cmpd 1)

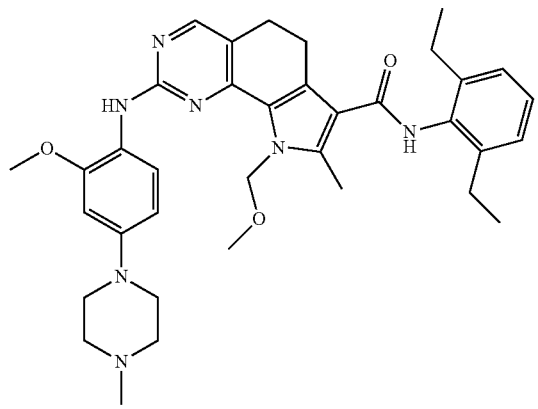 [SMILES: CCc1cccc(CC)c1NC(=O)c1c2c(n(COC)c1C)-c1nc(Nc3ccc(N4CCN(C)CC4)cc3OC)ncc1CC2]

MS calculated: 624.3657; MS found: 624.3660

2-[(4-bromo-2-methoxyphenyl)amino]-N-(2,6-diethylphenyl)-10-methyl-5,6,7,10-tetrahydropyrrolo[3',2':6,7]cyclohepta[1,2-d]pyrimidine-8-carboxamide [(I), R1=4-bromo-2-methoxyphenyl, X=—NH—, R2=—N-(2,6-diethylphenyl), R3=methyl, R4=H, A=—(CH$_2$)$_3$—] (cmpd 15)

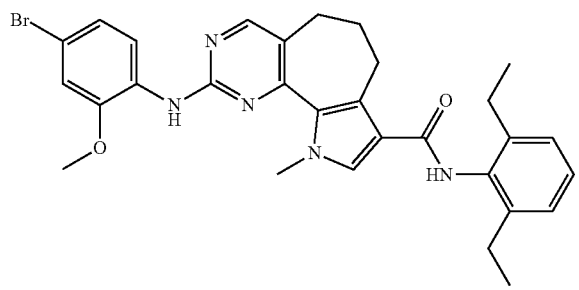 [SMILES: CCc1cccc(CC)c1NC(=O)c1cn(C)c2c1CCCc1cnc(Nc3ccc(Br)cc3OC)nc1-2]

MS calculated: 574.1812; MS found: 574.1797
$^1$H NMR (401 MHz, DMSO-d6) δ ppm 1.12 (t, J=7.57 Hz, 6H) 1.94-2.05 (m, 2H) 2.55 (q, J=7.57 Hz, 4H) 2.92 (t, J=7.14 Hz, 2H) 3.88 (s, 3H) 3.89 (s, 3H) 7.09-7.20 (m, 4H) 7.21 (d, J=2.32 Hz, 1H) 7.69 (s, 1H) 7.98 (s, 1H) 8.10 (d, J=8.54 Hz, 1H) 8.30 (s, 1H) 9.05 (s, 1H)

Example 5 (Conv. 6)

N-(2,6-diethylphenyl)-2-{[2-methoxy-4-(4-methylpiperazin-1-yl)phenyl]amino}-9-methyl-6,9-dihydro-5H-pyrrolo[3,2-h]quinazoline-7-carboxamide [(I), R1=2-methoxy-4-(4-methylpiperazin-1-yl)phenyl, X=—NH—, R2=—N-(2,6-diethylphenyl), R3=methyl, R4=H, A=—CH$_2$CH$_2$—] (cmpd 9)

Pd$_2$(dba)$_3$, (10 mg, 0.010 mmol), 2-dicyclohexylphosphino-2'-(N,N-dimethylamino)-biphenyl (10 mg, 0.025 mmol) and 2-[(4-bromo-2-methoxyphenyl)amino]-N-(2,6-diethylphenyl)-9-methyl-6,9-dihydro-5H-pyrrolo[3,2-h]quinazoline-7-carboxamide (100 mg, 0.178 mmol) in dry THF (5 mL) were charged in a round-bottom flask flushed with argon. The flask was evacuated and backfilled with argon. LiN(TMS)$_2$ solution (1M in THF, 1.39 mL) and N-methylpiperazine (0.058 mL, 0.522 mmol) were added and the reaction mixture was heated at 85° C. for 0.5 h. The reaction mixture was then allowed to cool to room temperature and solvent evaporated to dryness. The crude solid was purified by flash chromatography on silica gel (eluant: DCM/MeOH 95/5) to afford 72 mg (70% yield) of the title compound as yellow solid.

MS calculated: 580.3395; MS found: 580.3373

¹H NMR (401 MHz, DMSO-d6) δ ppm 1.11 (t, J=7.57 Hz, 6H) 2.25 (br. s., 3H) 2.54 (q, J=7.57 Hz, 4H) 2.69-2.76 (m, 2H) 2.91-2.99 (m, 2H) 3.05-3.19 (m, 4H) 3.82 (s, 3H) 4.04 (s, 3H) 6.49 (dd, J=8.67, J=2.56 Hz, 1H) 6.63 (d, J=2.56 Hz, 1H) 7.08-7.14 (m, 2H) 7.16-7.23 (m, 1H) 7.66 (s, 1H) 7.69 (s, 1H) 7.76 (d, J=8.67 Hz, 1H) 8.10 (s, 1H) 9.03 (s, 1H)

According to this same methodology, but employing suitable substituted derivatives, the following compounds were prepared:

N-(2,6-diethylphenyl)-2-({2-methoxy-4-[4-(pyrrolidin-1-yl)piperidin-1-yl]phenyl}amino)-8,9-dimethyl-6,9-dihydro-5H-pyrrolo[3,2-h]quinazoline-7-carboxamide [(I), R1=2-methoxy-4-[4-(pyrrolidin-1-yl)piperidin-1-yl]phenyl, X=—NH—, R2=—N-(2,6-diethylphenyl), R3=methyl, R4=methyl, A=—CH₂CH₂—] (cmpd 3)

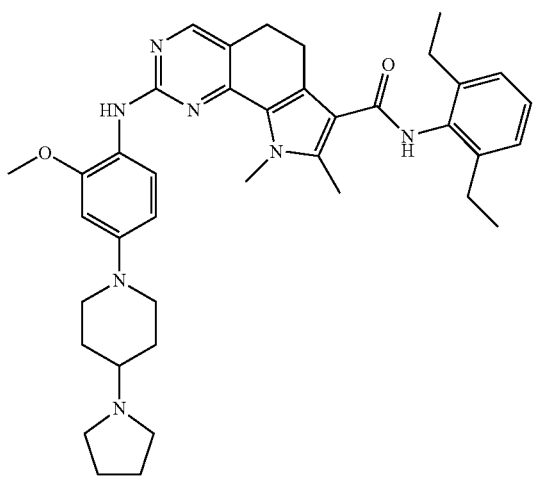 [SMILES: CCc1cccc(CC)c1NC(=O)c1c2c(n(C)c1C)-c1nc(Nc3ccc(N4CCC(N5CCCC5)CC4)cc3OC)ncc1CC2]

MS calculated: 648.4021; MS found: 648.4026

¹H NMR (401 MHz, DMSO-d6) δ ppm 1.13 (t, J=7.57 Hz, 6H) 1.47-1.61 (m, 2H) 1.64-1.76 (m, 4H) 1.88-1.98 (m, 2H) 2.42 (s, 3H) 2.52-2.63 (m, 8H) 2.64-2.75 (m, 4H) 2.83-2.92 (m, 2H) 3.26-3.29 (m, 2H) 3.54-3.65 (m, 2H) 3.82 (s, 3H) 3.98 (s, 3H) 6.49 (dd, J=8.65, 2.50 Hz, 1H) 6.63 (d, J=2.40 Hz, 1H) 7.08-7.15 (m, 2H) 7.17-7.24 (m, 1H) 7.62 (s, 1H) 7.74 (d, J=8.65 Hz, 1H) 8.06 (s, 1H) 8.81 (s, 1H)

N-(2,6-diethylphenyl)-2-({4-[4-(dimethylamino)piperidin-1-yl]-2-methoxyphenyl}amino)-8,9-dimethyl-6,9-dihydro-5H-pyrrolo[3,2-h]quinazoline-7-carboxamide [(I), R1=4-[4-(dimethylamino)piperidin-1-yl]-2-methoxyphenyl, X=—NH—, R2=—N-(2,6-diethylphenyl), R3=methyl, R4=methyl, A=—CH₂CH₂—] (cmpd 4)

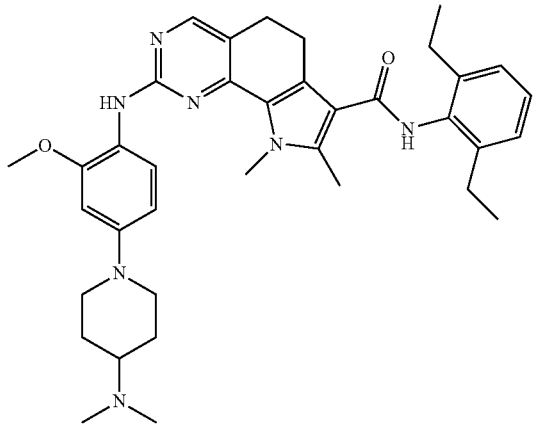 [SMILES: CCc1cccc(CC)c1NC(=O)c1c2c(n(C)c1C)-c1nc(Nc3ccc(N4CCC(N(C)C)CC4)cc3OC)ncc1CC2]

MS calculated: 622.3864; MS found: 622.3868

¹H NMR (401 MHz, DMSO-d6) δ ppm 1.13 (t, J=7.57 Hz, 6H) 1.44-1.60 (m, 2H) 1.68-1.90 (m, 2H) 2.23 (br.s., 6H) 2.42 (s, 3H) 2.58 (q, J=7.57 Hz, 4H) 2.60-2.69 (m, 2H) 2.69-2.75 (m, 2H) 2.83-2.93 (m, 2H) 3.61-3.70 (m, 2H) 3.82 (s, 3H) 3.98 (s, 3H) 6.49 (dd, J=8.70, 2.50 Hz, 1H) 6.63 (d, J=2.50 Hz, 1H) 7.06-7.16 (m, 2H) 7.17-7.24 (m, 1H) 7.62 (s, 1H) 7.74 (d, J=8.70 Hz, 1H) 8.06 (s, 1H) 8.81 (s, 1H)

N-(2,6-diethylphenyl)-2-{[2-methoxy-4-(4-methylpiperazin-1-yl)phenyl]amino}-8,9-dimethyl-6,9-dihydro-5H-pyrrolo[3,2-h]quinazoline-7-carboxamide [(I), R1=2-methoxy-4-(4-methylpiperazin-1-yl)phenyl, X=—NH—, R2=—N-(2,6-diethylphenyl), R3=methyl, R4=methyl, A=—CH₂CH₂—] (cmpd 5)

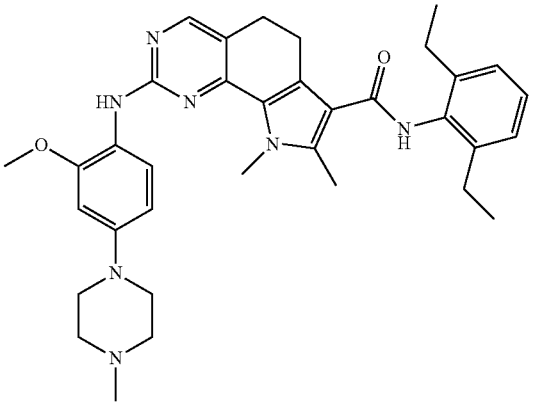 [SMILES: CCc1cccc(CC)c1NC(=O)c1c2c(n(C)c1C)-c1nc(Nc3ccc(N4CCN(C)CC4)cc3OC)ncc1CC2]

MS calculated: 594.3551; MS found: 594.3554

¹H NMR (401 MHz, DMSO-d6) δ ppm 1.13 (t, J=7.57 Hz, 6H) 2.25 (s, 3H) 2.42 (s, 3H) 2.58 (q, J=7.57 Hz, 4H) 2.68-2.79 (m, 2H) 2.84-2.91 (m, 2H) 3.07-3.17 (m, 4H) 3.82 (s, 3H) 3.99 (s, 3H) 6.49 (dd, J=8.80, 2.45 Hz, 1H) 6.63 (d, J=2.45 Hz, 1H) 7.06-7.17 (m, 2H) 7.17-7.24 (m, 1H) 7.62 (s, 1H) 7.77 (d, J=8.80 Hz, 1H) 8.07 (s, 1H) 8.82 (s, 1H)

N-(2,6-diethylphenyl)-2-({4-[4-(2-hydroxyethyl)piperazin-1-yl]-2-methoxyphenyl}amino)-8,9-dimethyl-6,9-dihydro-5H-pyrrolo[3,2-h]quinazoline-7-carboxamide [(I), R1=4-[4-(2-hydroxyethyl)piperazin-1-yl]-2-methoxyphenyl, X=—NH—, R2=—N-(2,6-diethylphenyl), R3=methyl, R4=methyl, A=—CH₂CH₂—] (cmpd 6)

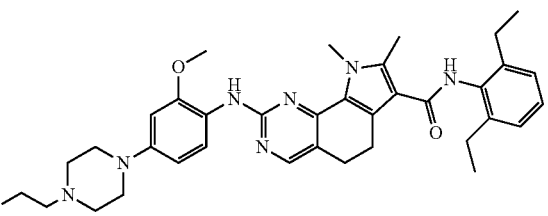

MS calculated: 624.3657; MS found: 624.3643

¹H NMR (401 MHz, DMSO-d6) δ ppm 1.13 (t, J=7.57 Hz, 6H) 2.42 (s, 3H) 2.44-2.49 (m, 6H) 2.58 (q, J=7.57 Hz, 4H) 2.73 (m, 2H) 2.88 (m, 2H) 3.06-3.20 (m, 4H) 3.49-3.61 (m, 2H) 3.82 (s, 3H) 3.99 (s, 3H) 4.41 (br. s., 1H) 6.48 (dd, J=8.70, 2.35 Hz, 1H) 6.63 (d, J=2.35 Hz, 1H) 7.04-7.16 (m, 2H) 7.17-7.23 (m, 1H) 7.63 (s, 1H) 7.76 (d, J=8.70 Hz, 1H) 8.06 (s, 1H) 8.82 (s, 1H)

2-{[2-methoxy-4-(4-methylpiperazin-1-yl)phenyl]
amino}-8,9-dimethyl-6,9-dihydro-5H-pyrrolo[3,2-h]
quinazoline-7-carboxamide [(I), R1=2-methoxy-4-
(4-methylpiperazin-1-yl)phenyl, X=—NH—,
R2=—NH$_2$, R3=methyl, R4=methyl,
A=—CH$_2$CH$_2$—] (cmpd 7)

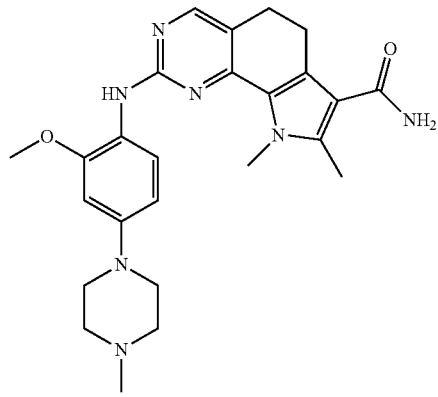 [SMILES: COc1cc(N2CCN(C)CC2)ccc1Nc1ncc2c(n1)-c1c(c(C(N)=O)c(C)n1C)CC2]

MS calculated: 462.2612; MS found: 462.2595

$^1$H NMR (401 MHz, DMSO-d6) δ ppm 2.22 (s, 3H) 2.38 (s, 3H) 2.43-2.47 (m, 4H) 2.61-2.69 (m, 2H) 2.73-2.81 (m, 2H) 3.06-3.13 (m, 4H) 3.80 (s, 3H) 3.93 (s, 3H) 6.47 (dd, J=8.70, 2.56 Hz, 1H) 6.61 (d, J=2.56 Hz, 1H) 6.89 (br. s., 2H) 7.58 (s, 1H) 7.74 (d, J=8.70 Hz, 1H) 8.04 (s, 1H)

N-(2,6-diethylphenyl)-2-({4-[4-(dimethylamino)
piperidin-1-yl]-2-methoxyphenyl}amino)-9-methyl-
6,9-dihydro-5H-pyrrolo[3,2-h]quinazoline-7-car-
boxamide [(I), R1=4-[4-(dimethylamino)piperidin-1-
yl]-2-methoxyphenyl, X=—NH—, R2=—N-(2,6-
diethylphenyl), R3=methyl, R4=H,
A=—CH$_2$CH$_2$—] (cmpd 10)

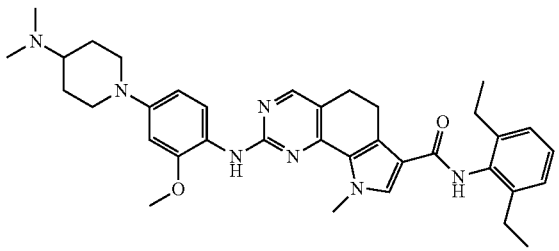 [SMILES: CCc1cccc(CC)c1NC(=O)c1cn(C)c2c1CCc1cnc(Nc3ccc(N4CCC(N(C)C)CC4)cc3OC)nc1-2]

MS calculated: 608.3708; MS found: 608.3712

$^1$H NMR (401 MHz, DMSO-d6) δ ppm 1.11 (t, J=7.57 Hz, 6H) 1.41-1.61 (m, 2H) 1.77-1.92 (m, 2H) 2.17-2.32 (m, 7H) 2.54 (q, J=7.57 Hz, 46H) 2.60-2.68 (m, 2H) 2.69-2.77 (m, 2H) 2.90-3.01 (m, 2H) 3.59-3.64 (m, 2H) 3.82 (s, 3H) 4.03 (s, 3H) 6.49 (dd, J=8.80, 2.56 Hz, 1H) 6.63 (d, J=2.56 Hz, 1H) 7.05-7.16 (m, 2H) 7.16-7.23 (m, 1H) 7.66 (s, 1H) 7.69 (s, 1H) 7.74 (d, J=8.80 Hz, 1H) 8.10 (s, 1H) 9.03 (s, 1H)

N-(2,6-diethylphenyl)-2-({2-methoxy-4-[4-(pyrroli-
din-1-yl)piperidin-1-yl]phenyl}amino)-9-methyl-6,9-
dihydro-5H-pyrrolo[3,2-h]quinazoline-7-carboxam-
ide [(I), R1=2-methoxy-4-[4-(pyrrolidin-1-yl)
piperidin-1-yl]phenyl, X=—NH—, R2=—N-(2,6-
diethylphenyl), R3=methyl, R4=H,
A=—CH$_2$CH$_2$—] (cmpd 11)

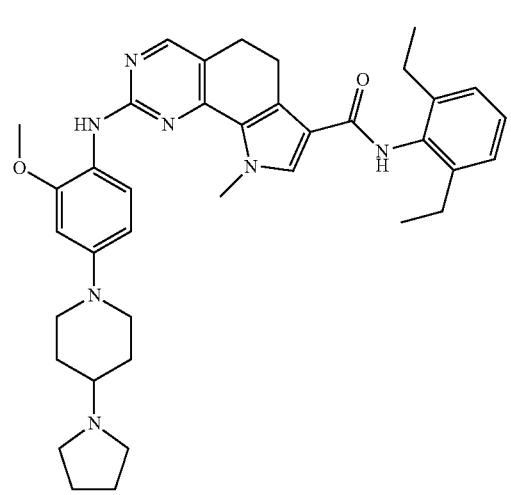 [SMILES: CCc1cccc(CC)c1NC(=O)c1cn(C)c2c1CCc1cnc(Nc3ccc(N4CCC(N5CCCC5)CC4)cc3OC)nc1-2]

MS calculated: 634.3864; MS found: 634.3874

$^1$H NMR (401 MHz, DMSO-d6) δ ppm 1.11 (t, J=7.57 Hz, 6H) 1.45-1.60 (m, 2H) 1.64-1.74 (m, 4H) 1.87-1.99 (m, 2H) 2.04-2.16 (m, 1H) 2.54 (q, J=7.57 Hz, 4H) 2.65-2.81 (m, 4H) 2.90-3.03 (m, 2H) 3.50-3.66 (m, 2H) 3.82 (s, 3H) 4.04 (s, 3H) 6.49 (dd, J=8.70, 2.50 Hz, 1H) 6.63 (d, J=2.50 Hz, 1H) 7.04-7.15 (m, 2H) 7.15-7.29 (m, 1H) 7.65 (s, 1H) 7.69 (s, 1H) 7.74 (d, J=8.70 Hz, 1H) 8.10 (s, 1H) 9.03 (s, 1H)

N-(2,6-diethylphenyl)-2-[(4-{[3-(dimethylamino)
propyl](methyl)amino}-2-methoxyphenyl)amino]-9-
methyl-6,9-dihydro-5H-pyrrolo[3,2-h]quinazoline-7-
carboxamide [(I), R1=4-{[3-(dimethylamino)
propyl]methylamino}-2-methoxyphenyl,
X=—NH—, R2=—N-(2,6-diethylphenyl),
R3=methyl, R4=H, A=—CH$_2$CH$_2$—] (cmpd 12)

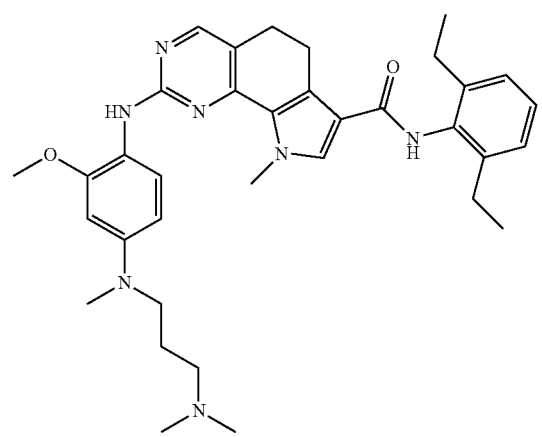 [SMILES: CCc1cccc(CC)c1NC(=O)c1cn(C)c2c1CCc1cnc(Nc3ccc(N(C)CCCN(C)C)cc3OC)nc1-2]

MS calculated: 596.3708; MS found: 596.3782

¹H NMR (401 MHz, DMSO-d6) δ ppm 1.11 (t, J=7.51 Hz, 6H) 1.64 (quin, J=6.80 Hz, 2H) 2.15 (s, 6H) 2.24 (t, J=6.80 Hz, 2H) 2.54 (q, J=7.51 Hz, 4H) 2.65-2.75 (m, 2H) 2.87 (s, 3H) 2.90-2.97 (m, 2H) 3.79 (s, 3H) 4.01 (s, 3H) 6.27 (dd, J=8.80, 2.50 Hz, 1H) 6.39 (d, J=2.50 Hz, 1H) 7.09-7.14 (m, 2H) 7.16-7.23 (m, 1H) 7.57 (d, J=8.80 Hz, 1H) 7.62 (s, 1H) 7.67 (s, 1H) 8.06 (s, 1H) 9.02 (s, 1H)

N-(2,6-diethylphenyl)-2-({4-[4-(2-hydroxyethyl)piperazin-1-yl]-2-methoxyphenyl}amino)-9-methyl-6,9-dihydro-5H-pyrrolo[3,2-h]quinazoline-7-carboxamide [(I), R1=4-[4-(2-hydroxyethyl)piperazin-1-yl]-2-methoxyphenyl, X=—NH—, R2=—N-(2,6-diethylphenyl), R3=methyl, R4=H, A=—CH₂CH₂—] (cmpd 13)

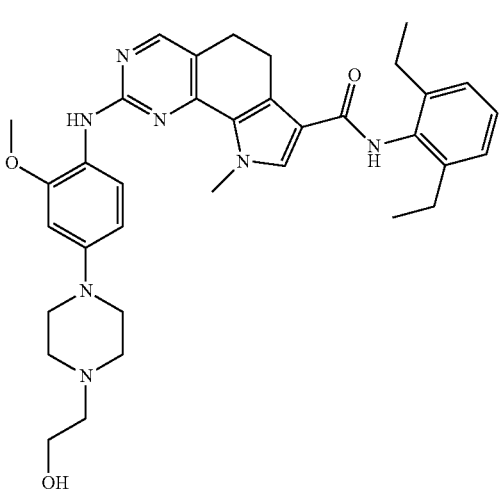 [SMILES: CCc1cccc(CC)c1NC(=O)c1cn(C)c2c1CCc1cnc(Nc3ccc(N4CCN(CCO)CC4)cc3OC)nc1-2]

MS calculated: 610.3500; MS found: 610.3498

¹H NMR (401 MHz, DMSO-d6) δ ppm 1.11 (t, J=7.51 Hz, 6H) 2.45 (t, J=6.10 Hz, 2H) 2.52-2.61 (m, 8H) 2.68-2.76 (m, 2H) 2.91-3.00 (m, 2H) 3.09-3.16 (m, 4H) 3.54 (q, J=6.10 Hz, 2H) 3.82 (s, 2H) 4.04 (s, 2H) 4.37-4.45 (m, 1H) 6.48 (dd, J=8.79, 2.44 Hz, 1H) 6.62 (d, J=2.44 Hz, 1H) 7.09-7.13 (m, 2H) 7.15-7.23 (m, 1H) 7.66 (s, 1H) 7.69 (s, 1H) 7.75 (d, J=8.79 Hz, 1H) 8.10 (s, 1H) 9.03 (s, 1H)

N-(2,6-diethylphenyl)-2-{[2-methoxy-4-(4-methylpiperazin-1-yl)phenyl]amino}-10-methyl-5,6,7,10-tetrahydropyrrolo[3',2':6,7]cyclohepta[1,2-d]pyrimidine-8-carboxamide [(I), R1=2-methoxy-4-(4-methylpiperazin-1-yl)phenyl, X=—NH—, R2=—N-(2,6-diethylphenyl), R3=methyl, R4=H, A=—(CH₂)₃—] (cmpd 16)

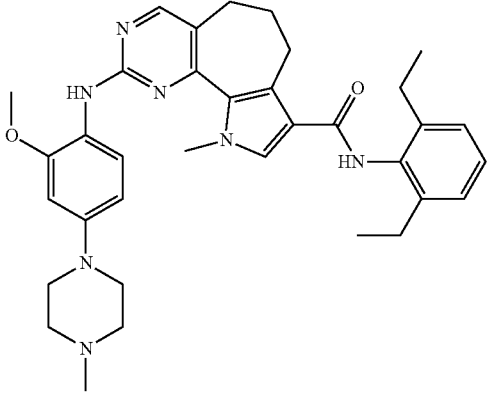 [SMILES: CCc1cccc(CC)c1NC(=O)c1cn(C)c2c1CCCc1cnc(Nc3ccc(N4CCN(C)CC4)cc3OC)nc1-2]

MS calculated: 594.3551; MS found: 594.3524

¹H NMR (401 MHz, DMSO-d6) δ ppm 1.11 (t, J=7.57 Hz, 6H) 1.89-2.03 (m, 2H) 2.23 (s, 3H) 2.43-2.48 (m, 4H) 2.55 (q, J=7.57 Hz, 4H) 2.91 (t, J=7.14 Hz, 2H) 3.09-3.15 (m, 4H) 3.80 (s, 3H) 3.81 (s, 3H) 6.49 (dd, J=8.70, 2.50 Hz, 1H) 6.63 (d, J=2.50 Hz, 1H) 7.08-7.15 (m, 2H) 7.15-7.23 (m, 1H) 7.61-7.68 (m, 2H) 7.79 (s, 1H) 8.19 (s, 1H) 9.01 (s, 1H)

N-(2,6-diethylphenyl)-2-({4-[4-(dimethylamino)piperidin-1-yl]-2-methoxyphenyl}amino)-10-methyl-5,6,7,10-tetrahydropyrrolo[3',2':6,7]cyclohepta[1,2-d]pyrimidine-8-carboxamide [(I), R1=4-[4-(dimethylamino)piperidin-1-yl]-2-methoxyphenyl, X=—NH—, R2=—N-(2,6-diethylphenyl), R3=methyl, R4=H, A=—(CH₂)₃—] (cmpd 17)

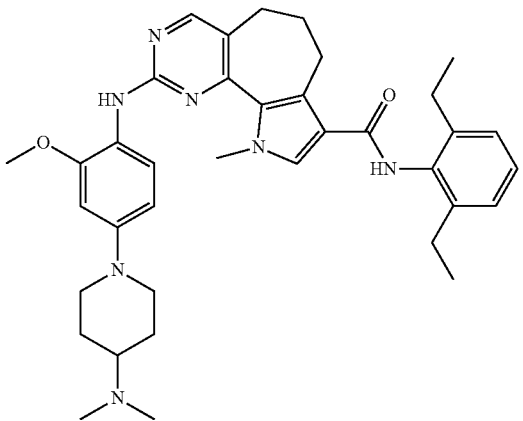 [SMILES: CCc1cccc(CC)c1NC(=O)c1cn(C)c2c1CCCc1cnc(Nc3ccc(N4CCC(N(C)C)CC4)cc3OC)nc1-2]

MS calculated: 622.3864; MS found: 622.3876

¹H NMR (401 MHz, DMSO-d6) δ ppm 1.11 (t, J=7.57 Hz, 6H) 1.42-1.58 (m, 2H) 1.76-1.89 (m, 2H) 1.92-2.02 (m, 2H) 2.13-2.19 (m, 1H) 2.18-2.23 (m, 6H) 2.43-2.48 (m, 2H) 2.55 (q, J=7.57 Hz, 4H) 2.60-2.70 (m, 2H) 2.92 (t, J=7.08 Hz, 2H) 3.62-3.72 (m, 2H) 3.79 (s, 3H) 3.80 (s, 3H) 6.50 (dd, J=8.75, 2.44 Hz, 1H) 6.62 (d, J=2.44 Hz, 1H) 7.05-7.14 (m, 2H) 7.13-7.24 (m, 1H) 7.58-7.68 (m, 2H) 7.79 (s, 1H) 8.19 (s, 1H) 9.01 (s, 1H)

N-(2,6-diethylphenyl)-2-({2-methoxy-4-[4-(pyrrolidin-1-yl)piperidin-1-yl]phenyl}amino)-10-methyl-5,6,7,10-tetrahydropyrrolo[3',2':6,7]cyclohepta[1,2-d]pyrimidine-8-carboxamide [(I), R1=2-methoxy-4-[4-(pyrrolidin-1-yl)piperidin-1-yl]phenyl, X=—NH—, R2=—N-(2,6-diethylphenyl), R3=methyl, R4=H, A=—(CH₂)₃—] (cmpd 18)

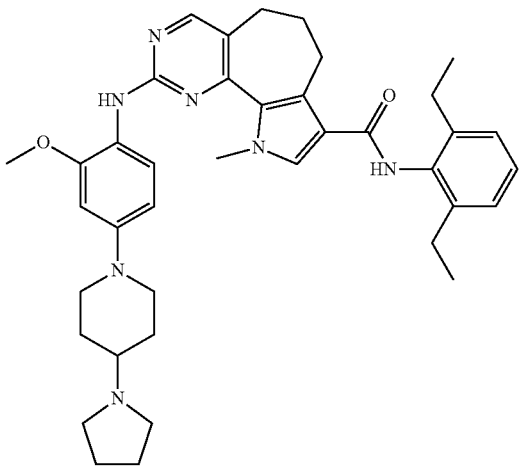 [SMILES: CCc1cccc(CC)c1NC(=O)c1cn(C)c2c1CCCc1cnc(Nc3ccc(N4CCC(N5CCCC5)CC4)cc3OC)nc1-2]

MS calculated: 648.4021; MS found: 648.4023

¹H NMR (401 MHz, DMSO-d6) δ ppm 1.11 (t, J=7.57 Hz, 6H) 1.42-1.59 (m, 2H) 1.63-1.76 (m, 4H) 1.83-2.04 (m, 4H) 2.04-2.18 (m, 1H) 2.42-2.50 (m, 6H) 2.54 (q, J=7.57 Hz, 4H) 2.65-2.77 (m, 2H) 2.92 (t, J=7.14 Hz, 2H) 3.51-3.65 (m, 2H) 3.79 (s, 3H) 3.80 (s, 3H) 6.50 (dd, J=8.85, 2.50 Hz, 1H) 6.62 (d, J=2.45 Hz, 1H) 7.03-7.15 (m, 2H) 7.15-7.24 (m, 1H) 7.58-7.68 (m, 2H) 7.78 (s, 1H) 8.19 (s, 1H) 9.01 (s, 1H)

Example 6 (Conv. 2)

Ethyl 2-[(4-bromo-2-methoxyphenyl)amino]-8,9-dimethyl-6,9-dihydro-5H-pyrrolo[3,2-h]quinazoline-7-carboxylate [(I), R1=4-bromo-2-methoxyphenyl, X=—NH—, R2=—O-ethyl, R3=methyl, R4=methyl, A=—CH$_2$CH$_2$—]

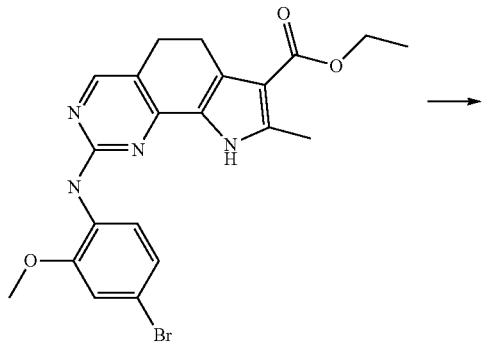

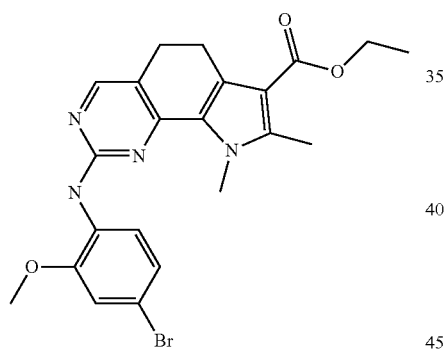

To a solution of ethyl 2-[(4-bromo-2-methoxyphenyl)amino]-8-methyl-6,9-dihydro-5H-pyrrolo[3,2-h]quinazoline-7-carboxylate (50 mg, 0.11 mmol) in DMF (1 mL), Cs$_2$CO$_3$ (73 mg, 0.22 mmol) and methyl iodide (0.007 mL, 0.11 mmol) were added. The mixture was stirred at room temperature for 8 h, solvent was removed under vacuo, then DCM (10 mL) was added and the organic phase washed with water (2×15 mL). The organic fraction was dried over Na$_2$SO$_4$, filtered, and concentrated in vacuo. Purification by flash chromatography on silica gel (eluant: AcOEt/hexane 4/6) provided 40 mg (yield: 80%) of the title compound as a pale yellow solid.

MS calculated: 471.1027; MS found: 471.1031

¹H NMR (401 MHz, DMSO-d6) δ ppm 1.28 (t, J=7.08 Hz, 3H) 2.53 (s, 3H) 2.72 (t, J=7.63 Hz, 2H) 2.91 (t, J=7.63 Hz, 2H) 3.88 (s, 3H) 4.00 (s, 3H) 4.20 (q, J=7.08 Hz, 2H) 7.12 (dd, J=8.55, 2.14 Hz, 1H) 7.20 (d, J=2.14 Hz, 1H) 7.89 (s, 1H) 8.07 (d, J=8.55 Hz, 1H) 8.17 (s, 1H)

According to this same methodology, but employing suitable substituted derivatives, the following compound was prepared:

Ethyl 2-amino-8,9-dimethyl-6,9-dihydro-5H-pyrrolo[3,2-h]quinazoline-7-carboxylate [(I), R1=—H, X=—NH—, R2=—O-ethyl, R3=methyl, R4=methyl, A=—CH$_2$CH$_2$—]

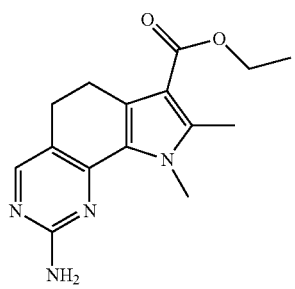 [SMILES: CCOC(=O)c1c2c(n(C)c1C)-c1nc(N)ncc1CC2]

Example 7 (Conv. 7)

Ethyl 2-({2-methoxy-4-[(1-methylpiperidin-4-yl)carbamoyl]phenyl}amino)-8,9-dimethyl-6,9-dihydro-5H-pyrrolo[3,2-h]quinazoline-7-carboxylate [(I), R1=2-methoxy-4-[(1-methylpiperidin-4-yl) carbamoyl]phenyl, X=—NH—, R2=—O-ethyl, R3=methyl, R4=methyl, A=—CH$_2$CH$_2$—]

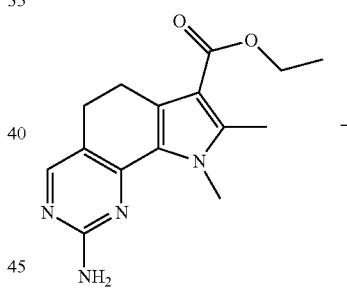

To a solution of ethyl 2-amino-8,9-dimethyl-6,9-dihydro-5H-pyrrolo[3,2-h]quinazoline-7-carboxylate (87 mg, 0.280 mmol) in dioxane (2 mL), 4-iodo-3-methoxy-N-(1-methylpiperidin-yl)benzamide (112 mg, 0.254 mmol) and Cs$_2$CO$_3$ (92 mg, 0.280 mmol) were added and the flask was evacuated and backfilled with argon. Pd$_2$(dba)$_3$ (4.7 mg, 0.005 mmol) and Xantphos (6.5 mg, 0.011 mmol) were then charged and the mixture was heated at 80° C. under argon for 8 hours. After cooling to room temperature, the reaction mixture was concentrated, suspended in H$_2$O (10 mL) and extracted with AcOEt (3×15 mL). The organic phase was anidrified on Na$_2$SO$_4$, filtered and evaporated to dryness, the crude solid was purified by flash chromatography on silica gel (eluant: DCM/MeOH 9/2) to afford 100 mg (yield: 70%) of the title compound as a yellow solid.

$^1$H NMR (500 MHz, DMSO-d6) δ ppm 1.29 (t, J=7.00 Hz, 3H) 1.54-1.67 (m, 2H) 1.72-1.83 (m, 2H) 1.91-2.08 (m, 2H) 2.20 (br. s., 3H) 2.55 (s, 3H) 2.70-2.76 (m, 2H) 2.77.2.86 (m, 2H) 2.89-2.98 (m, 2H) 3.69-3.81 (m, 1H) 3.94 (s, 2H) 4.05 (s, 2H) 4.20 (q, J=7.00 Hz, 2H) 7.40-7.54 (m, 2H) 7.97 (s, 1H) 8.12 (d, J=7.69 Hz, 1H) 8.22 (s, 1H) 8.29 (d, J=8.24 Hz, 1H)

Example 8 (Conv 4)

2-[(4-bromo-2-methoxyphenyl)amino]-N-[(1S)-2-(1,3-dioxo-1,3-dihydro-2H-isoindol-2-yl)-1-phenyl ethyl]-9-methyl-6,9-dihydro-5H-pyrrolo[3,2-h]quinazoline-7-carboxamide [(I), R1=4-bromo-2-methoxyphenyl, X=—NH—, R2=N-[(1S)-2-(1,3-dioxo-1,3-dihydro-2H-isoindol-2-yl)-1-phenyl ethyl], R3=methyl, R4=H, A=—CH$_2$CH$_2$—] (cmpd 14)

2-[(4-bromo-2-methoxyphenyl)amino]-9-methyl-6,9-dihydro-5H-pyrrolo[3,2-h]quinazoline-7-carboxylic acid (50 mg, 0.116 mmol) in dry DMF (5.0 mL) was treated with DIPEA (0.056 mL, 0.033 mmol) and TBTU (65 mg, 0.200 mmol). The mixture was then treated with 2-[(2S)-2-amino-2-phenylethyl]-1H-isoindole-1,3(2H)-dione (3 mg, 0.011 mmol).

The reaction was stirred at room for 4 h. The reaction was diluted with water and the resulting precipitate was collected by filtration to afford 35 mg (yield: 45%) of the title compound as yellow solid.

MS calculated: 677.1507; MS found: 677.1521

Example 9 (Step G)

Ethyl 8-methyl-2-(methylsulfanyl)-6,9-dihydro-5H-pyrrolo[3,2-h]quinazoline-7-carboxylate

[(I), R1=methyl, X=—S—, R2=—O-ethyl, R3=H, R4=methyl, A=—CH$_2$CH$_2$—] and ethyl 2-(dimethylamino)-8-methyl-6,9-dihydro-5H-pyrrolo[3,2-h]quinazoline-7-carboxylate [(I), R1=methyl, X=—N(Me)-, R2=—O-ethyl, R3=H, R4=methyl, A=—CH$_2$CH$_2$—]

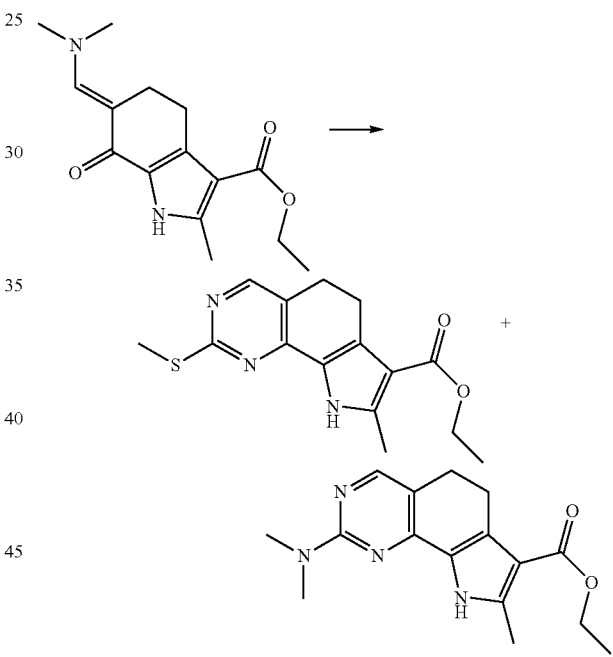

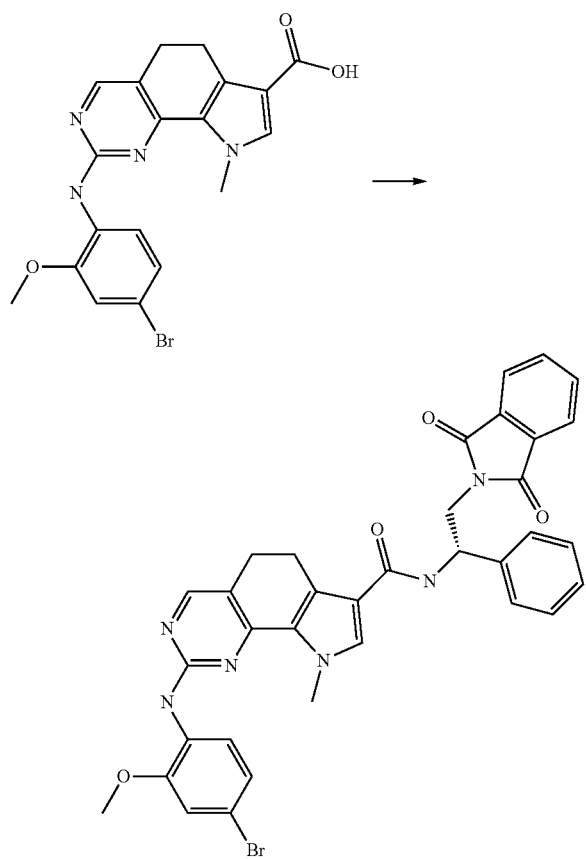

To a solution of ethyl (6E)-6-[(dimethylamino)methylidene]-2-methyl-7-oxo-4,5,6,7-tetrahydro-1H-indole-3-carboxylate 2 g (7.22 mmol) in 20 mL of anhydrous DMF, 1.41 g (14.4 mmol) of anhydrous potassium acetate and 4.0 g (14.4 mmol) of methylisothiourea sulfate were added. The reaction was stirred at 100° C. for 3 hours. The mixture was diluted with ethyl acetate, washed with H$_2$O, dried over Na$_2$SO$_4$, filtered and evaporated. The crude was purified by silica gel chromography (ethyl acetate:hexane 4:6) to give as major compound 0.8 g of ethyl 8-methyl-2-(methylsulfanyl)-6,9-dihydro-5H-pyrrolo[3,2-h]quinazoline-7-carboxylate (40%)

LC/MS (254 nm) HPLC method 2 Rt 5.79 min.

$^1$H NMR (500 MHz, DMSO-d6) δ 1.28 (t, J=7.05 Hz, 3H) 2.52 (s, 3H) 2.82 (t, J=8.05 Hz, 2H) 2.95 (t, J=8.05 Hz, 2H) 3.33 (s, 3H) 4.18 (q, J=7.05 Hz, 2H) 8.25 (s, 1H) 12.13 (br. s., 1H).

HRMS (ESI) calcd for $C_{15}H_{18}N_3O_2S$ [M+H]$^+$ 304.1114 found 304.1120;

and as minor product 0.2 g ethyl 2-(dimethylamino)-8-methyl-6,9-dihydro-5H-pyrrolo[3,2-h]quinazoline-7-carboxylate (10%).

LC/MS (254 nm) HPLC method 2 Rt 5.44 min.

$^1$H NMR (600 MHz, DMSO-d6) δ 1.27 (t, J=7.08 Hz, 3H) 2.50 (s, 3H) 2.70 (t, J=7.88 Hz, 2H) 2.89 (t, J=7.88 Hz, 2H) 3.13 (s, 6H) 4.18 (q, J=7.08 Hz, 2H) 7.99 (s, 1H) 11.78 (br. s., 1H).

HRMS (ESI) calcd for $C_{16}H_{21}N_4O$ [M+H]$^+$ 301.1659 found 301.1655.

Applying the same method, the following compound was prepared:

methyl 2-(methylsulfanyl)-6,9-dihydro-5H-pyrrolo[3,2-h]quinazoline-7-carboxylate [(I), R1=methyl, X=—S—, R2=—O-methyl, R3=R4=H, A=—CH$_2$CH$_2$—]

LC/MS (254 nm) HPLC method 2 Rt 5.02 min.

$^1$H NMR (600 MHz, DMSO-d6) δ 2.53 (s, 3H) 2.86 (t, J=8.06 Hz, 2H) 2.99 (t, J=8.06 Hz, 2H) 3.73 (s, 3H) 7.57 (s, 1H) 8.31 (s, 1H) 12.42 (br. s., 1H).

HRMS (ESI) calcd for $C_{13}H_{14}N_3O_2S$ [M+H]$^+$ 276.0801 found 276.0799.

Example 10 (Conv. 2)

Ethyl 8-methyl-2-(methylsulfanyl)-9-(propan-2-yl)-6,9-dihydro-5H-pyrrolo[3,2-h]quinazoline-7-carboxylate [(I), R1=methyl, X=—S—, R2=O-ethyl, R3=H, R4=methyl, A=—CH$_2$CH$_2$—]

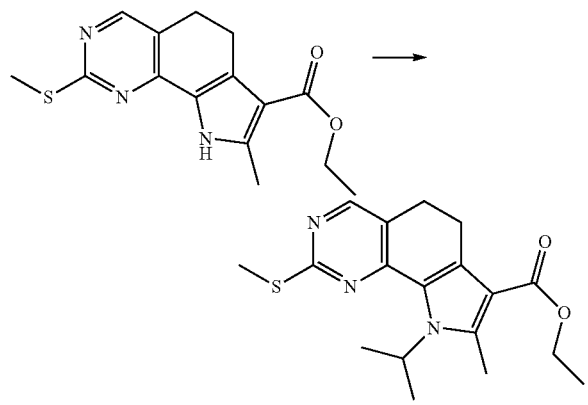

To a solution of ethyl 8-methyl-2-(methylsulfanyl)-6,9-dihydro-5H-pyrrolo[3,2-h]quinazoline-7-carboxylate (100 mg, 0.33 mmol) in dry DMF (2 mL), Cs$_2$CO$_3$ (160 mg, 0.495 mmol) and 2-iodo propane (0.08 ml, 0.825 mmol) were added. The reaction was stirred at 80° C. for 8 h. HPLC/MS analysis showed 50% of conversion, therefore an additional amount of reagents were added into the pot and stirred at the same temperature for further 8 h. The mixture was poured into H$_2$O (100 mL) and the product extracted with EtOAc (3×30 mL). The organic fractions were dried over Na$_2$SO$_4$, filtrated, and concentrated in vacuo. The crude solid was purified by flash chromatography on silica gel (eluant: AcOEt/hexane 1/9) to afford 75 mg (yield: 66%) of the title compound as an off-white solid.

LC/MS (254 nm) HPLC method 2 Rt 7.34 min.

$^1$H NMR (600 MHz, DMSO-d6) δ 1.28 (t, J=7.08 Hz, 3H) 1.55 (d, J=7.14 Hz, 6H) 2.51 (s, 3H) 2.66 (s, 3H) 2.70-2.74 (m, 2H) 2.87-2.91 (m, 2H) 4.20 (q, J=7.08 Hz, 2H) 5.90 (br. s., 1H) 8.28 (s, 1H).

HRMS (ESI) calcd for $C_{18}H_{24}N_3O_2S$ [M+H]$^+$ 346.1584 found 346.1595.

Example 11 (Conv. 2)

methyl 9-[1-(tert-butoxycarbonyl)piperidin-4-yl]-2-(methylsulfanyl)-6,9-dihydro-5H-pyrrolo[3,2-h]quinazoline-7-carboxylate [(I), R1=methyl, X=—S—, R2=—O-methyl, R3=1-(tert-butoxy carbonyl)piperidin-4-yl, R4=H, A=—CH$_2$CH$_2$—]

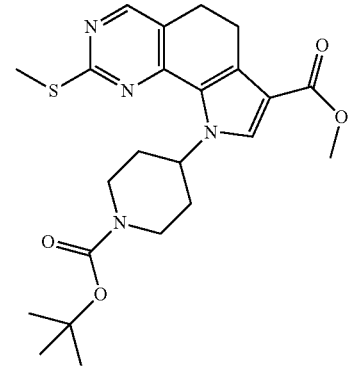

To a mixture of methyl 2-(methylsulfanyl)-6,9-dihydro-5H-pyrrolo[3,2-h]quinazoline-7-carboxylate (60 mg 0.218 mmol), tert-butyl-4-hydroxypiperidine-1-carboxylate (88 mg, 0.436 mmol), and triphenylphosphine (120 mg, 0.436 mmol), in anhydrous THF (5 mL) at room temperature, was added di tert-butyl-diazadicarboxylate (DTAD) (100 mg, 0.436 mmol). The mixture was stirred at room temperature for 18 h. HPLC/MS suggested 30% conversion and 70% SM remained, reagents were added, triphenylphosphine (120 mg, 0.436 mmol) and DTAD (100 mg, 0.436 mmol) in 5 mL of THF, the mixture was stirred for 6 hours. HPLC/MS showed 70% conversion and 30% SM remained. Reagents were re-added TPP (120 mg, 0.436 mmol) and DTAD (100 mg, 0.436 mmol) in 5 mL of THF, the solution was stirred for additional 18 hours. The volatiles were removed in vacuo, the crude solid was purified by flash chromatography on silica gel (hexane/EtOAc 7/3) to afford 69 mg (70% yield) of the title compound.

LC/MS (254 nm) HPLC method 2 Rt 8.10 min.

Applying the same method, the following compound was prepared:

methyl 9-[1-(tert-butoxycarbonyl)piperidin-4-yl]-8-iodo-2-(methylsulfanyl)-9H-pyrrolo[3,2-h]quinazoline-7-carboxylate [(I), R1=methyl, X=—S—, R2=—O-ethyl, R3=1-(tert-butoxy carbonyl)piperidin-4-yl, R4=I, A=—CH=CH—]

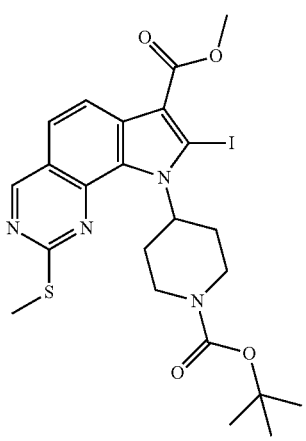 [SMILES: COC(=O)c1c(I)n(C2CCN(C(=O)OC(C)(C)C)CC2)c2c1ccc1cnc(SC)nc12]

Example 12 (Conv. 2)

methyl 9-{cis-4-[(tert-butoxycarbonyl)amino]cyclohexyl}-2-(methylsulfanyl)-6,9-dihydro-5H-pyrrolo[3,2-h]quinazoline-7-carboxylate [(I), R1=methyl, X=—S—, R2=O-methyl, R3=cis-4-[(tert-butoxycarbonyl)amino]cyclohexyl, R4=H, A=—CH$_2$CH$_2$—]

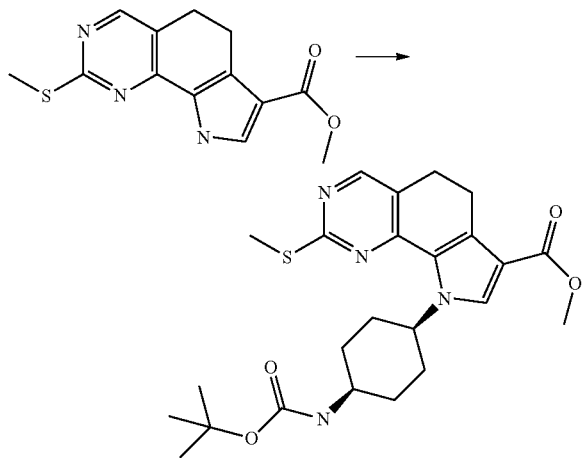

To a solution of methyl 2-(methylsulfanyl)-6,9-dihydro-5H-pyrrolo[3,2-h]quinazoline-7-carboxylate (100 mg 0.363 mmol) in THF (5 mL) trans-tert-butyl-4-hydroxycyclohexylcarbamate (156 mg 0.727 mmol), Ph$_3$P (190 mg, 0.727 mmol) and DEAD (113 μl, 0.727 mmol) were added. The mixture was stirred at room temperature for 16 hours, HPLC/MS suggested unreacted starting material (80%) and desired product (20%), then additional 190 mg of Ph$_3$P and 113 μL of DEAD were added. After 5 h, the solvent was removed by rotary evaporation to give a viscous orange oil. Mixture of SM (60%) and desired product (40%) was isolated by flash chromatography on silica gel using 20:80 EtOAc-hexane as eluant. The mixture dissolved in THF (5 mL) was submitted again with trans-tert-butyl-4-hydroxycyclohexylcarbamate (156 mg 0.727 mmol), Ph$_3$P (190 mg, 0.727 mmol), DEAD (113 μl, 0.727 mmol) and stirred at room temperature for 16 h. HPLC/MS suggested unreacted starting material (40%) and desired product (60%), then added an additional 95 mg of Ph$_3$P and 56 μL of DEAD and stirred for 4 h. The reaction needed five additional refresh of reagents before went to completion. The volatiles were removed under vacuo and the crude purified by silica gel chromatography (hexanes/EtOAc 8/2) to give the title compound as a yellow solid (160 mg 93% yield).

LC/MS (254 nm) HPLC method 2 Rt 8.11 min.

Example 13 (Conv. 3)

8-methyl-2-(methylsulfanyl)-6,9-dihydro-5H-pyrrolo[3,2-h]quinazoline-7-carboxylic acid [(I), R1=methyl, X=—S—, R2=OH, R3=H, R4=methyl, A=—CH$_2$CH$_2$—]

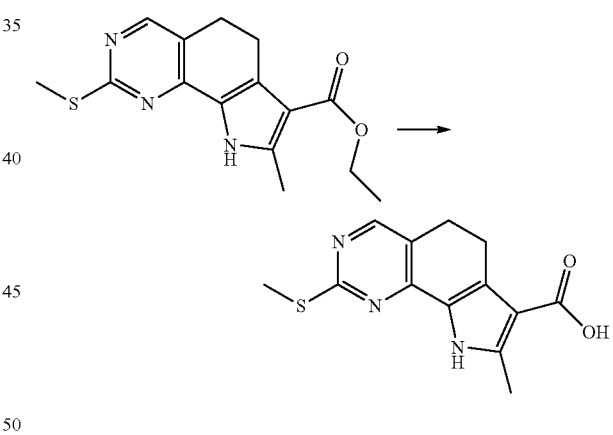

Ethyl 8-methyl-2-(methylsulfanyl)-6,9-dihydro-5H-pyrrolo[3,2-h]quinazoline-7-carboxylate (110 mg, 0.36 mmol) was suspended in dioxane (10 mL) and treated with a 2 N solution of NaOH (4.0 ml, 8 mmol) at 95° C. for 18 h. H$_2$O (20 mL) was added and the solution was acidified with HCl 2N. The mixture was portioned between ethyl acetate and water, the organic layer was dried over Na$_2$SO$_4$, filtered and concentrated, to provide 95 mg (95%) of the title compound as off-white solid.

LC/MS (254 nm) HPLC method 2 Rt 4.13 min.

$^1$H NMR (600 MHz, DMSO-d6) δ 2.48 (s, 3H) 2.52 (s, 3H) 2.77-2.83 (m, 2H) 2.92-2.96 (m, 2H) 8.24 (s, 1H) 12.05 (br. s., 1H).

HRMS (ESI) calcd for C$_{13}$H$_{14}$N$_3$O$_2$S [M+H]$^+$ 276.0801 found 276.0804.

Operating in an analogous way, the following compounds were prepared:

2-(methylsulfanyl)-6,9-dihydro-5H-pyrrolo[3,2-h]quinazoline-7-carboxylic acid [(I), R1=methyl, X=—S—, R2=OH, R3=R4=H, A=—CH₂CH₂—]

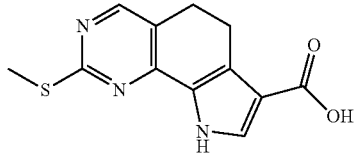 [SMILES: CSc1ncc2c(n1)-c1[nH]cc(C(=O)O)c1CC2]

LC/MS (254 nm) HPLC method 2 Rt 3.61 min.
¹H NMR (600 MHz, DMSO-d6) δ 2.53 (s, 3H) 2.85 (t, J=7.75 Hz, 2H), 2.98 (t, J=7.75 Hz, 2H) 7.48-7.52 (m, 1H) 8.30 (s, 1H) 12.32 (br. s., 1H).
HRMS (ESI) calcd for C₁₂H₁₂N₃O₂S [M+H]⁺ 262.0645 found 262.0649.

8-methyl-2-(methylsulfanyl)-9-(propan-2-yl)-6,9-dihydro-5H-pyrrolo[3,2-h]quinazoline-7-carboxylic acid [(I), R1=methyl, X=—S—, R2=OH, R3=isopropyl, R4=methyl, A=—CH₂CH₂—]

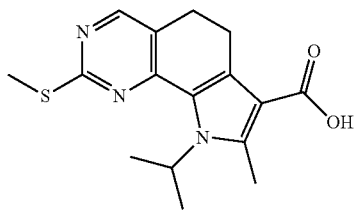 [SMILES: CSc1ncc2c(n1)-c1c(c(C(=O)O)c(C)n1C(C)C)CC2]

LC/MS (254 nm) HPLC method 2 Rt 5.43 min.
¹H NMR (600 MHz, DMSO-d6) δ 1.55 (d, J=6.96 Hz, 6H) 2.48 (s, 3H) 2.66 (s, 3H) 2.71 (t, J=7.78 Hz, 2H) 2.89 (t, J=7.75 Hz, 2H) 8.27 (s, 1H) 12.20 (br. s., 1H)
HRMS (ESI) calcd for C₁₆H₂₀N₃O₂S [M+H]⁺ 318.1271 found 318.1263.

2-(dimethylamino)-8-methyl-6,9-dihydro-5H-pyrrolo[3,2-h]quinazoline-7-carboxylic acid [(I), R1=methyl, X=—N(Me)-, R2=OH, R3=H, R4=methyl, A=—CH₂CH₂—]

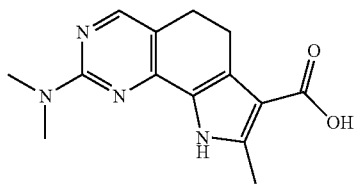 [SMILES: Cc1[nH]c2c(c1C(=O)O)CCc1cnc(N(C)C)nc1-2]

LC/MS (254 nm) HPLC method 2 Rt 3.17 min.
¹H NMR (600 MHz, DMSO-d6) δ 2.54 (s, 3H) 2.79 (t, J=7.20 Hz, 2H) 2.98 (t, J=7.20 Hz, 2H) 3.23 (s, 6H) 7.49 (s, 1H) 7.91 (s, 1H) 12.20 (br. s., 1H).

HRMS (ESI) calcd for C₁₄H₁₇N₄O₂ [M+H]⁺ 273.1346 found 273.1346.

9-[1-(tert-butoxycarbonyl)piperidin-4-yl]-2-(methylsulfanyl)-6,9-dihydro-5H-pyrrolo[3,2-h]quinazoline-7-carboxylic acid [(I), R1=methyl, X=—S—, R2=OH, R3=1-(tert-butoxycarbonyl)piperidin-4-yl, R4=H, A=—CH₂CH₂—]

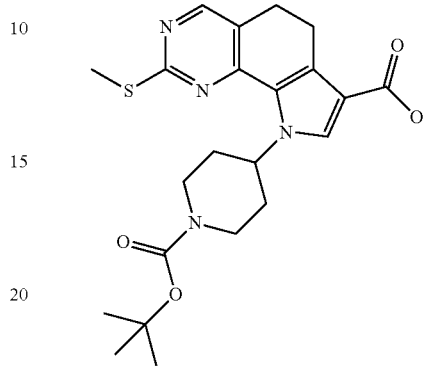

LC/MS (254 nm) HPLC method 2 Rt 6.13 min.
9-{cis 4-[(tert-butoxycarbonyl)amino]cyclohexyl}-2-(methylsulfanyl)-6,9-dihydro-5H-pyrrolo[3,2-h]quinazoline-7-carboxylic acid [(I), R1=methyl, X=—S—, R2=OH, R3=cis 4-[(tert-butoxycarbonyl)amino]cyclohexyl, R4=H, A=—CH₂CH₂—]

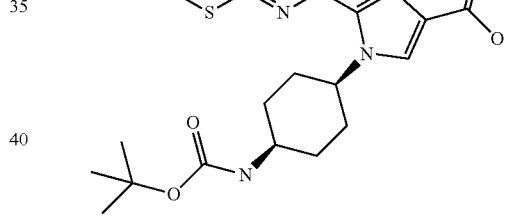

LC/MS (254 nm) HPLC method 2 Rt 6.38 min.
¹H NMR (600 MHz, DMSO-d6) δ 12.13 (br. s., 1H), 8.31 (s, 1H), 8.04 (s, 1H), 7.23 (d, J=8.97 Hz, 1H), 5.45 (ddd, J=4.03, 8.33, 12.00 Hz, 1H), 3.81 (br. s., 1H), 2.91-2.96 (m, 2H), 2.72-2.80 (m, 2H), 2.00-2.12 (m, 2H), 1.77-1.86 (m, 2H), 1.67-1.75 (m, 2H), 1.59 (m, 2H), 1.42 (s, 9H).
HRMS (ESI) calcd for C₂₃H₃₁N₄O₄S [M+H]⁺ 459.2061 found 459.2066.

2-methyl-6,9-dihydro-5H-pyrrolo[3,2-h]quinazoline-7-carboxylic acid [(I), R1=methyl, X=single bond, R2=OH, R3=H, R4=H, A=—CH₂CH₂—]

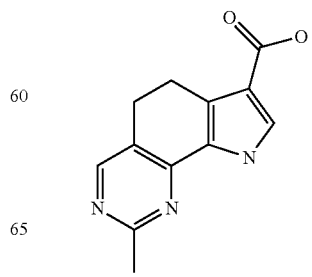

Example 14 (Conv. 4)

8-methyl-2-(methylsulfanyl)-9-(propan-2-yl)-6,9-dihydro-5H-pyrrolo[3,2-h]quinazoline-7-carboxamide [(I), R1=methyl, X=—S—, R2=NH$_2$, R3=is-propyl, R4=methyl, A=—CH$_2$CH$_2$—] (cmpd 19)

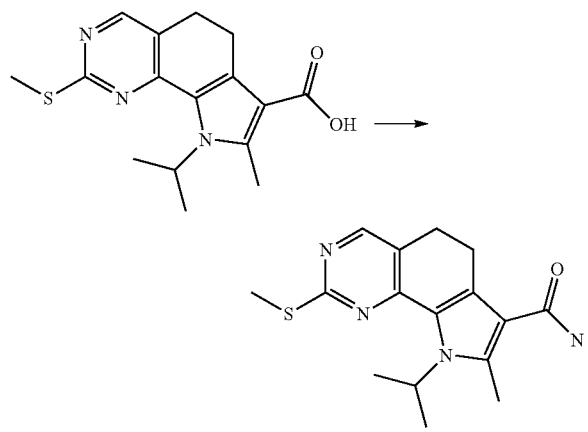

8-methyl-2-(methylsulfanyl)-9-(propan-2-yl)-6,9-dihydro-5H-pyrrolo[3,2-h]quinazoline-7-carboxylic acid (100 mg, 0.363 mmol) in dry DMA (2.0 mL) was treated with NH$_4$Cl (0.062 g 0.108 mmol), DIPEA (0.253 mL, 0.14 mmol) and TBTU (175 mg, 0.544 mmol). The reaction was stirred at room for 18 h. The reaction was diluted with sat. NaHCO$_3$ and the resulting precipitate was collected by filtration, washed with diethyl ether to afford 90 mg (yield: 90%) of the title compound as yellow solid.

LC/MS (254 nm) HPLC method 2 Rt 4.63 min.

HRMS (ESI) calcd for C$_{16}$H$_{21}$N$_4$OS [M+H]$^+$ 317.1431 found 317.1435.

By working according to this method, the following compounds were prepared:

8-methyl-2-(methylsulfanyl)-6,9-dihydro-5H-pyrrolo[3,2-h]quinazoline-7-carboxamide [(I), R1=methyl, X=—S—, R2=NH$_2$, R3=H, R4=methyl, A=—CH$_2$CH$_2$—] (cmpd 20)

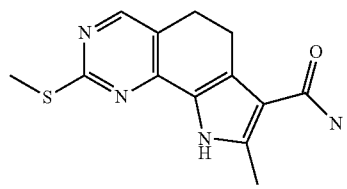 [SMILES: CSc1ncc2c(n1)-c1[nH]c(C)c(C(N)=O)c1CC2]

LC/MS (254 nm) HPLC method 3 Rt 4.63 min.

$^1$H NMR (500 MHz, DMSO-d6) δ 2.42 (s, 3H) 2.52 (s, 3H) 2.79 (t, J=8.05 Hz, 2H) 2.87 (t, J=8.05 Hz, 2H) 6.53-7.04 (m, 2H) 8.21 (s, 1H) 11.79 (br. s., 1H)

HRMS (ESI) calcd for C$_{13}$H$_{15}$N$_4$OS [M+H]$^+$ 275.0961 found 275.0968.

2-(methylsulfanyl)-6,9-dihydro-5H-pyrrolo[3,2-h]quinazoline-7-carboxamide [(I), R1=methyl, X=—S—, R2=NH$_2$, R3=R4=H, A=—CH$_2$CH$_2$—] (cmpd 21)

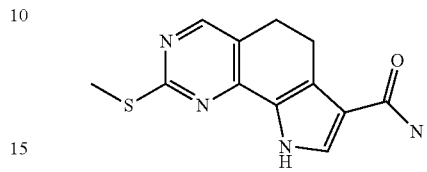

LC/MS (254 nm) HPLC method 3 Rt 5.43 min.

$^1$H NMR (500 MHz, DMSO-d6) δ 2.52 (s, 3H) 2.81 (t, J=7.78 Hz, 2H) 3.00 (t, J=7.78 Hz, 2H) 6.79 (br. s., 1H) 7.31 (br. s., 1H) 7.61 (d, J=3.11 Hz, 1H) 8.27 (s, 1H) 12.02 (br. s., 1H)

HRMS (ESI) calcd for C$_{12}$H$_{13}$N$_4$OS [M+H]$^+$ 261.0805 found 261.0814.

2-(methylsulfanyl)-9-(propan-2-yl)-6,9-dihydro-5H-pyrrolo[3,2-h]quinazoline-7-carboxamide [(I), R1=methyl, X=—S—, R2=NH$_2$, R3=is-propyl, R4=H, A=—CH$_2$CH$_2$—] (cmpd 22)

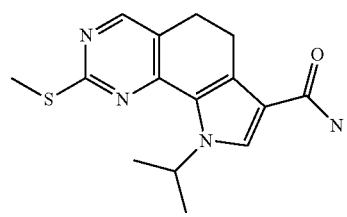 [SMILES: CSc1ncc2c(n1)-c1c(c(C(N)=O)cn1C(C)C)CC2]

LC/MS (254 nm) HPLC method 3 Rt 4.48 min.

$^1$H NMR (600 MHz, DMSO-d6) δ 1.44 (d, J=6.59 Hz, 6H) 2.75 (t, J=7.78 Hz, 2H) 2.98 (t, J=7.78 Hz, 2H) 5.63-5.74 (m, 1H) 6.81 (br. s., 1H) 7.30 (br. s., 1H) 7.88 (s, 1H) 8.28 (s, 1H)

HRMS (ESI) calcd for C$_{15}$H$_{19}$N$_4$OS [M+H]$^+$ 303.1274 found 303.1277.

2-(dimethylamino)-8-methyl-6,9-dihydro-5H-pyrrolo[3,2-h]quinazoline-7-carboxamide [(I), R1=methyl, X=—N(Me)-, R2=NH$_2$, R3=H, R4=methyl, A=—CH$_2$CH$_2$—] (cmpd 23)

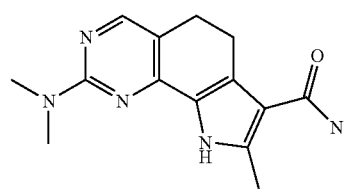 [SMILES: Cc1[nH]c2c(c1C(N)=O)CCc1cnc(N(C)C)nc1-2]

LC/MS (254 nm) HPLC method 3 Rt 2.65 min.

$^1$H NMR (600 MHz, DMSO-d6) δ 2.43 (s, 3H) 2.67 (t, J=7.69 Hz, 2H) 2.81 (t, J=7.69 Hz, 2H) 3.13 (s, 6H) 6.50-6.95 (m, 2H) 7.96 (s, 1H) 11.45 (br. s., 1H).

HRMS (ESI) calcd for $C_{14}H_{18}N_5O$ [M+H]$^+$ 272.1506 found 272.1509.

tert-butyl 4-[7-carbamoyl-2-(methylsulfanyl)-5,6-dihydro-9H-pyrrolo[3,2-h]quinazolin-9-yl]piperidine-1-carboxylate [(I), R1=methyl, X=—S—, R2=NH$_2$, R3=1-(tert-butoxycarbonyl)piperidin-4-yl, R4=H, A=—CH$_2$CH$_2$—]

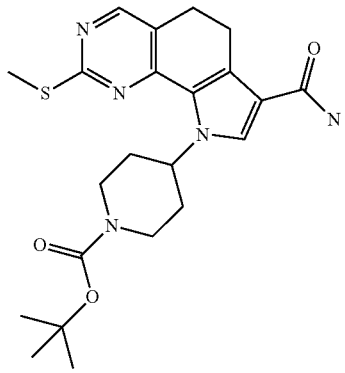 [SMILES: CSc1ncc2c(n1)-c1c(c(C(N)=O)cn1C1CCN(C(=O)OC(C)(C)C)CC1)CC2]

LC/MS (254 nm) HPLC method 1 Rt 1.473 min.

tert-butyl {cis-4-[7-carbamoyl-2-(methylsulfanyl)-5,6-dihydro-9H-pyrrolo[3,2-h]quinazolin-9-yl]cyclohexyl}carbamate [(I), R1=methyl, X=—S—, R2=NH$_2$, R3=cis 4-[(tert-butoxycarbonyl)amino]cyclohexyl, R4=H, A=—CH$_2$CH$_2$—]

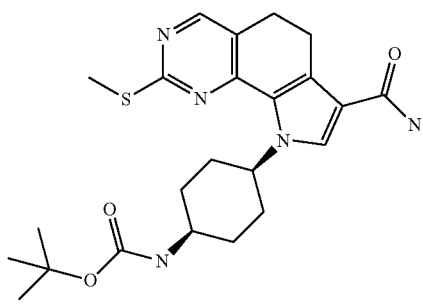 [SMILES: CSc1ncc2c(n1)-c1c(c(C(N)=O)cn1[C@H]1CC[C@@H](NC(=O)OC(C)(C)C)CC1)CC2]

LC/MS (254 nm) HPLC method 1 Rt 1.501 min.

2-methyl-6,9-dihydro-5H-pyrrolo[3,2-h]quinazoline-7-carboxamide [(I), R1=methyl, X=single bond, R2=NH$_2$, R3=H, R4=H, A=—CH$_2$CH$_2$—] (cmpd 37)

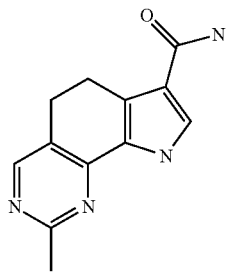 [SMILES: Cc1ncc2c(n1)-c1[nH]cc(C(N)=O)c1CC2]

HRMS (ESI) calcd for $C_{14}H_{18}N_5O$ [M+H]$^+$ 229.1084 found 229.1085.

tert-butyl 4-(2-amino-7-carbamoyl-5,6-dihydro-9H-pyrrolo[3,2-h]quinazolin-9-yl)piperidine-1-carboxylate [(I), R1=H, X=—NH—, R2=NH$_2$, R3=4-[(tert-butoxycarbonyl)amino]cyclohexyl, R4=H, A=—CH$_2$CH$_2$—]

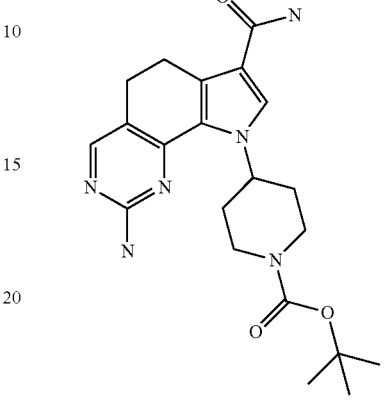

$^1$H NMR (600 MHz, DMSO-d6) d ppm 1.43 (s, 9H) 1.56-1.67 (m, 2H) 1.98-2.05 (m, 2H) 2.61 (t, J=7.69 Hz, 2H) 2.92 (t, J=7.69 Hz, 2H) 2.95-3.05 (m, 2H) 4.01-4.16 (m, 2H) 5.57-5.68 (m, 1H) 6.37 (br. s., 2H) 6.75 (br. s., 2H) 7.80 (s, 1H) 7.95 (s, 1H)

HRMS (ESI) calcd for $C_{15}H_{18}N_4O_2S$ [M+H]$^+$ 413.2296. found 413.2296.

Example 15 (Conv. 2)

9-(2-hydroxyethyl)-8-methyl-2-(methylsulfanyl)-6,9-dihydro-5H-pyrrolo[3,2-h]quinazoline-7-carboxamide [(I), R1=methyl, X=—S—, R2=NH$_2$, R3=2-hydroxyethyl, R4=methyl, A=—CH$_2$CH$_2$—] (cmpd 24)

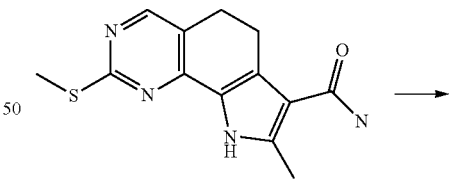

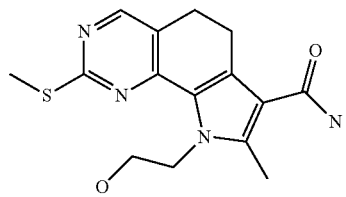

To a solution of 8-methyl-2-(methylsulfanyl)-6,9-dihydro-5H-pyrrolo[3,2-h]quinazoline-7-carboxamide (30 mg, 0.109 mmol) in dry dimethylformamide (2 mL), 2-iodo ethanol (37 µL, 0.437 mmol) and cesium carbonate (106 mg 0.327 mmol) were added. The resulting mixture was heated at 90° C. for 8 hours. After cooling to room temperature, the mixture was poured into water and extracted with EtOAc. The organic layer washed with brine, dried over Na$_2$SO$_4$ and concentrated. The crude was purified by silica gel chromatography eluting with DCM/MeOH 95/5 to give the title compound 8 mg (25%).

LC/MS (254 nm) HPLC method 2 Rt 3.32 min.

$^1$H NMR (400 MHz, DMSO-d6) δ 2.45 (s, 3H) 2.47 (s, 3H) 2.74 (t, J=8.05 Hz, 2H) 2.83 (t, J=8.05 Hz, 2H) 3.68 (q, J=5.90 Hz, 2H) 4.54 (t, J=5.90 Hz, 2H) 4.86 (t, J=5.90 Hz, 1H) 6.70-7.09 (m, 2H) 8.22 (s, 1H).

HRMS (ESI) calcd for C$_{15}$H$_{18}$N$_4$O$_2$S [M+H]$^+$ 319.1223 found 319.1215.

By working according to this method, the following compound was prepared:

9-(2-hydroxyethyl)-2-(methylsulfanyl)-6,9-dihydro-5H-pyrrolo[3,2-h]quinazoline-7-carboxamide [(I), R1=methyl, X=—S—, R2=NH$_2$, R3=2-hydroxyethyl, R4=H, A=—CH$_2$CH$_2$—] (cmpd 25)

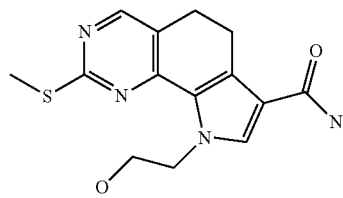 [SMILES: CSc1ncc2c(n1)-c1c(c(C(N)=O)cn1CCO)CC2]

LC/MS (254 nm) HPLC method 2 Rt 4.21 min.

$^1$H NMR (400 MHz, DMSO-d6) δ 2.47 (s, 3H) 2.77 (t, J=7.80 Hz, 2H) 2.99 (t, J=7.80 Hz, 2H) 3.71 (q, J=5.50 Hz, 2H) 4.52 (t, J=5.50 Hz, 2H) 4.90 (t, J=5.50 Hz, 1H) 6.81 (br. s., 1H) 7.30 (br. s., 1H) 7.63 (s, 1H) 8.27 (s, 1H).

HRMS (ESI) calcd for C$_{14}$H$_{17}$N$_4$O$_2$S [M+H]$^+$ 305.1067 found 305.1062.

Example 16 (Conv. 23)

methyl 2-(methylsulfanyl)-9H-pyrrolo[3,2-h]quinazoline-7-carboxylate [(I), R1=methyl, X=—S—, R2=—O-methyl, R3=R4=H, A=—CH=CH—]

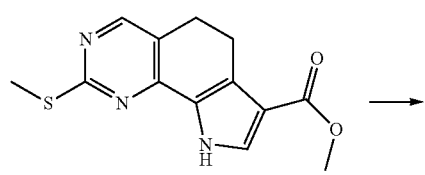

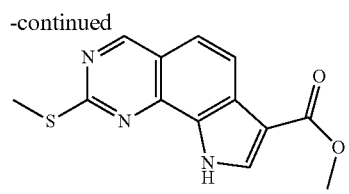

A solution of methyl 2-(methylsulfanyl)-6,9-dihydro-5H-pyrrolo[3,2-h]quinazoline-7-carboxylate 250 mg (0.91 mmol) and 330 mg (1.82 mmol) of DDQ in chlorobenzene was heated at 140° C. for 2 hours. The volatiles were removed in vacuo, the residue was dissolved with ethyl acetate, and washed with sat. aqueous solution of NaHCO$_3$. The organic phase was dried with Na$_2$SO$_4$, filtered and concentrated. The crude material was purified by silica gel column chromatography eluting with ethyl acetate and hexane (1:4) yielding the title compound 180 mg (90%).

LC/MS (254 nm) HPLC method 2 Rt 5.72 min.

$^1$H NMR (400 MHz, DMSO-d6) δ 2.73 (s, 3H) 3.86 (s, 3H) 7.74 (d, J=8.61 Hz, 1H) 8.20 (d, J=8.61 Hz, 1H) 8.26 (d, J=3.11 Hz, 1H) 9.37 (s, 1H) 13.23 (br. s., 1H).

HRMS (ESI) calcd for C$_{13}$H$_{12}$N$_3$O$_2$S [M+H]$^+$ 274.0645 found 274.065.

Using the same method as described in the above example, the following analogs were also synthesized:

Ethyl 8-methyl-2-(methylsulfanyl)-9H-pyrrolo[3,2-h]quinazoline-7-carboxylate [(I), R1=methyl, X=—S—, R2=—O-methyl, R3=H, R4=methyl, A=—CH=CH—]

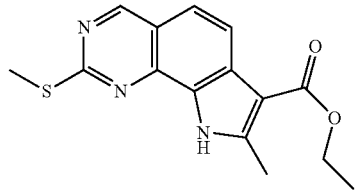 [SMILES: CCOC(=O)c1c(C)[nH]c2c1ccc1cnc(SC)nc12]

LC/MS (254 nm) HPLC method 2 Rt 5.95 min.

$^1$H NMR (400 MHz, DMSO-d6) δ 1.38 (t, J=7.14 Hz, 3H) 2.73 (s, 3H) 2.77 (s, 3H) 4.33 (q, J=7.14 Hz, 2H) 7.68 (d, J=8.61 Hz, 1H) 8.15 (d, J=8.61 Hz, 1H) 9.32 (s, 1H) 12.93 (br. s., 1H).

HRMS (ESI) calcd for C$_{15}$H$_{14}$N$_3$O$_2$S [M+H]$^+$ 302.0958 found 302.0957.

2-(dimethylamino)-8-methyl-9H-pyrrolo[3,2-h]quinazoline-7-carboxamide [(I), R1=methyl, X=—S—, R2=NH$_2$, R3=H, R4=methyl, A=—CH=CH—] (cmpd 26)

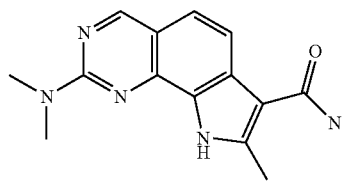 [SMILES: Cc1[nH]c2c(ccc3cnc(N(C)C)nc32)c1C(N)=O]

LC/MS (254 nm) HPLC method 2 Rt 3.52 min.

$^1$H NMR (400 MHz, DMSO-d6) δ 2.67 (s, 3H) 3.30 (s, 6H) 7.01 (s, 2H) 7.35 (d, J=8.61 Hz, 1H) 7.67 (d, J=8.61 Hz, 1H) 9.04 (s, 1H) 12.08 (br. s., 1H).

HRMS (ESI) calcd for $C_{14}H_{16}N_5OS$ [M+H]$^+$ 270.1350 found 270.1352.

Example 17 (Conv. 2)

methyl 9-methyl-2-(methylsulfanyl)-9H-pyrrolo[3,2-h]quinazoline-7-carboxylate [(I), R1=methyl, X=—S—, R2=—O-methyl, R3=methyl, R4=H, A=—CH=CH—]

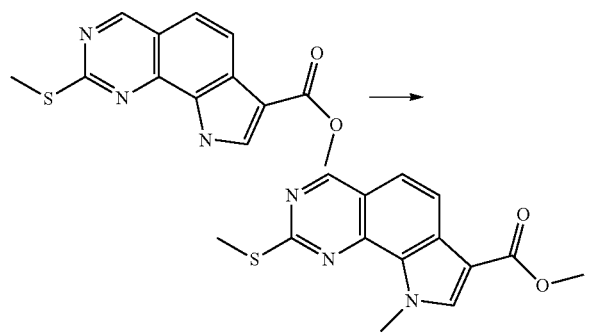

To a solution of methyl 2-(methylsulfanyl)-9H-pyrrolo[3,2-h]quinazoline-7-carboxylate (80 mg 0.29 mmol) in DMF (1.5 mL), $Cs_2CO_3$ (191 mg, 0.58 mmol) and methyl iodide (18 μL, 0.29 mmol) were added. The mixture was stirred at room temperature for 8 h, solvent was removed under vacuo, then DCM (10 mL) was added and the organic phase washed with water (2×15 mL). The organic fraction was dried over $Na_2SO_4$, filtrated and concentrated in vacuo. Purification by flash chromatography on silica gel (eluant: AcOEt/hexane 4/6) provided 58 mg (yield: 70%) of the title compound as a pale yellow solid.

LC/MS (254 nm) HPLC method 2 Rt 6.4 min.

$^1$H NMR (400 MHz, DMSO-d6) δ 2.68 (s, 3H) 3.86 (s, 3H) 4.49 (s, 3H) 7.75 (d, J=8.67 Hz, 1H) 8.21 (d, J=8.67 Hz, 1H) 8.35 (s, 1H) 9.35 (s, 1H).

HRMS (ESI) calcd for $C_{14}H_{14}N_3O_2S$ [M+H]$^+$ 288.0801 found 288.0802.

Example 18 (Conv. 3)

9-methyl-2-(methylsulfanyl)-9H-pyrrolo[3,2-h]quinazoline-7-carboxylic acid [(I), R1=methyl, X=—S—, R2=—OH, R3=R4=H, A=—CH=CH—]

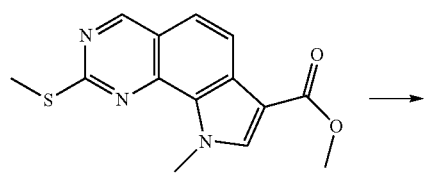

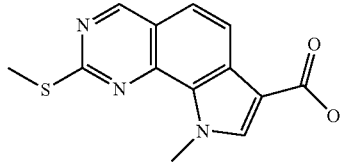

Methyl 9-methyl-2-(methylsulfanyl)-9H-pyrrolo[3,2-h]quinazoline-7-carboxylate (50 mg, 0.174 mmol) was suspended in dioxane (5 mL) and treated with a 2 N solution of NaOH (2.0 mL, 4 mmol) at 95° C. for 2 h. $H_2O$ (20 mL) was added and the solution was acidified (pH ~6) with HCl 2N. The solid was filtrated and washed with water and diethyl ether to provide 40 mg (85%) of the title compound as off-white solid.

LC/MS (254 nm) HPLC method 2 Rt 4.13 min.

$^1$H NMR (600 MHz, DMSO-d6) δ 2.68 (s, 3H) 4.48 (s, 3H) 7.71 (d, J=8.61 Hz, 1H) 8.23 (d, J=8.61 Hz, 1H) 8.26 (s, 1H) 9.34 (s, 1H) 12.35 (br. s., 1H).

HRMS (ESI) calcd for $C_{13}H_{12}N_3O_2S$ [M+H]$^+$ 274.0645 found 274.064.

Working according to the same method the following compounds were prepared:

8-methyl-2-(methylsulfanyl)-9H-pyrrolo[3,2-h]quinazoline-7-carboxylic acid [(I), R1=methyl, X=—S—, R2=—OH, R3=H, R4=methyl, A=—CH=CH—]

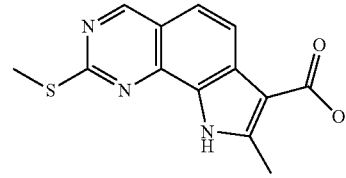

LC/MS (254 nm) HPLC method 2 Rt 4.21 min.

$^1$H NMR (600 MHz, DMSO-d6) δ 2.73 (s, 3H) 2.76 (s, 3H) 7.65 (d, J=8.61 Hz, 1H) 8.18 (d, J=8.61 Hz, 1H) 9.31 (s, 1H) 12.23 (br. s., 1H) 12.83 (br. s., 1H).

HRMS (ESI) calcd for $C_{13}H_{12}N_3O_2S$ [M+H]$^+$ 274.0645 found 274.065.

9-[1-(tert-butoxycarbonyl)piperidin-4-yl]-2-(methylsulfanyl)-9H-pyrrolo[3,2-h]quinazoline-7-carboxylic acid [(I), R1=methyl, X=—S—, R2=—OH, R3=1-(tert-butoxycarbonyl)piperidin-4-yl, R4=H, A=—CH=CH—]

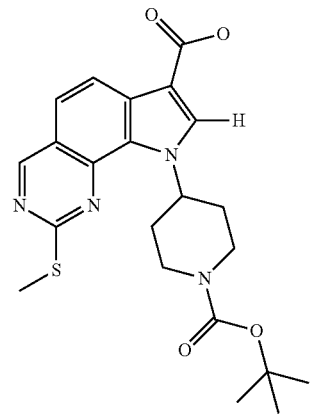

2-(methylsulfanyl)-9H-pyrrolo[3,2-h]quinazoline-7-carboxylic acid [(I), R1=methyl, X=—S—, R2=—OH, R3=H, R4=methyl, A=—CH=CH—]

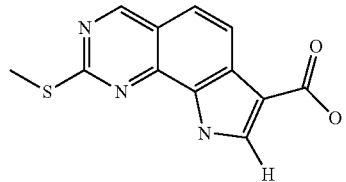 [SMILES: CSc1ncc2ccc3c(C(=O)O)c[nH]c3c2n1]

Example 19 (Conv. 4)

9-methyl-2-(methylsulfanyl)-9H-pyrrolo[3,2-h]quinazoline-7-carboxamide [(I), R1=methyl, X=—S—, R2=NH$_2$, R3=Methyl, R4=H, A=—CH=CH—] (cmpd 27)

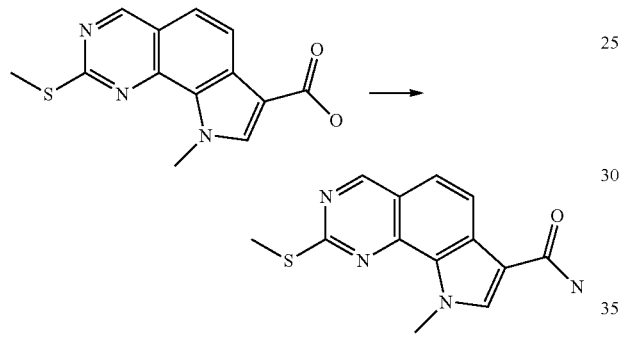

9-methyl-2-(methylsulfanyl)-9H-pyrrolo[3,2-h]quinazoline-7-carboxylic acid (30 mg, 0.109 mmol) in dry DMA (2.0 mL) was treated with NH$_4$Cl (0.040 g 0.74 mmol), DIPEA (0.120 ml, 0.68 mmol) and TBTU (70 mg, 0.218 mmol). The reaction was stirred at room temperature for 3 h. The reaction was diluted with sat. NaHCO$_3$ and the product extracted with EtOAc (3×30 mL). The organic fractions were dried over Na$_2$SO$_4$, filtered and evaporated in vacuo to afford 27 mg (yield: 93%) of the title compound as off-white solid.

LC/MS (254 nm) HPLC method 2 Rt 3.84 min.
$^1$H NMR (500 MHz, DMSO-d6) δ 2.68 (s, 3H) 4.46 (s, 3H) 7.01 (br. s., 1H) 7.58 (br. s., 1H) 7.64 (d, J=8.61 Hz, 1H) 8.19 (s, 1H) 8.39 (d, J=8.61 Hz, 1H) 9.31 (s, 1H).
HRMS (ESI) calcd for C$_{13}$H$_{13}$N$_4$OS [M+H]$^+$ 273.0805 found 273.0814.

Working according to the same method the following compounds were prepared:

8-methyl-2-(methylsulfanyl)-9H-pyrrolo[3,2-h]quinazoline-7-carboxamide [(I), R1=methyl, X=—S—, R2=NH$_2$, R3=H, R4=methyl, A=—CH=CH—] (cmpd 28)

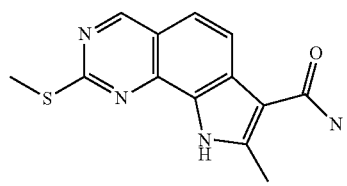 [SMILES: CSc1ncc2ccc3c(C(N)=O)c(C)[nH]c3c2n1]

LC/MS (254 nm) HPLC method 2 Rt 3.54 min.
$^1$H NMR (600 MHz, DMSO-d6) δ 2.71 (s, 3H) 2.72 (s, 3H) 7.14 (s, 2H) 7.58 (d, J=8.61 Hz, 1H) 8.04 (d, J=8.61 Hz, 1H) 9.29 (s, 1H) 12.57 (s, 1H).
HRMS (ESI) calcd for C$_{13}$H$_{13}$N$_3$O$_2$S [M+H]$^+$ 273.0805 found 273.0807.

tert-butyl 4-[7-carbamoyl-2-(methylsulfanyl)-9H-pyrrolo[3,2-h]quinazolin-9-yl]piperidine-1-carboxylate [(I), R1=methyl, X=—S—, R2=—NH$_2$, R3=1-(tert-butoxycarbonyl)piperidin-4-yl, R4=H, A=—CH=CH—]

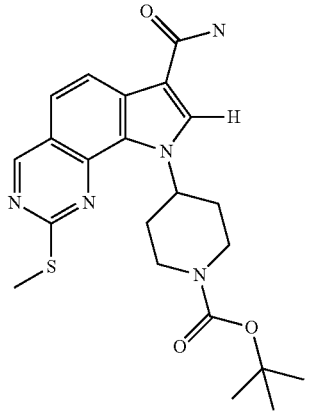 [SMILES: CSc1ncc2ccc3c(C(N)=O)cn(C4CCN(C(=O)OC(C)(C)C)CC4)c3c2n1]

2-(methylsulfanyl)-9H-pyrrolo[3,2-h]quinazoline-7-carboxamide [(I), R1=methyl, X=—S—, R2=—NH$_2$, R3=H, R4=H, A=—CH=CH—] (cmpd 36)

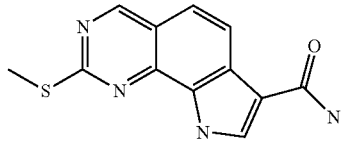 [SMILES: CSc1ncc2ccc3c(C(N)=O)c[nH]c3c2n1]

$^1$H NMR (600 MHz, DMSO-d6) d ppm 2.72 (s, 3H) 6.98 (br. s., 1H) 7.62 (d, J=8.61 Hz, 1H) 7.64 (br. s., 1H) 8.28 (s, 1H) 8.37 (d, J=8.61 Hz, 1H) 9.33 (s, 1H) 12.80 (br. s., 1H)
HRMS (ESI) calcd for C$_{13}$H$_{13}$N$_3$O$_2$S [M+H]$^+$ 259.0648. found 259.0646.

Example 20 (Conv. 2)

9-(2-hydroxyethyl)-8-methyl-2-(methylsulfanyl)-9H-pyrrolo[3,2-h]quinazoline-7-carboxamide [(I), R1=methyl, X=—S—, R2=NH$_2$, R3=2-hydroxyethyl, R4=methyl, A=—CH=CH—] (cmpd 29)

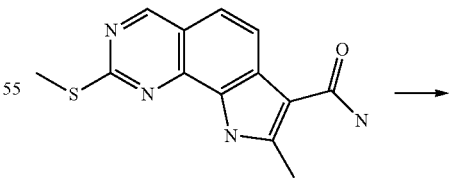

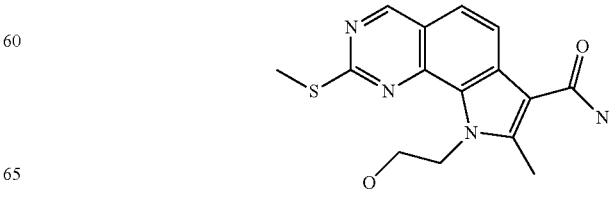

To a solution of 8-methyl-2-(methylsulfanyl)-9H-pyrrolo[3,2-h]quinazoline-7-carboxamide (20 mg 0.072 mmol) in DMF (1.5 mL), 2-iodo ethanol (24 µL, 0.288 mmol) and cesium carbonate (70 mg 0.216 mmol) were added. The resulting mixture was heated at 80° C. for 8 hours. After cooling to room temperature, the reaction mixture was poured in water (10 mL) and portioned with ethyl acetate. The organic layers were washed with brine, dried over $Na_2SO_4$ and concentrated. The crude was purified by silica gel chromatography (DCM/MeOH/acetone 85/0.5/1) to give the title compound 10 mg (45%) as a white solid.

LC/MS (254 nm) HPLC method 2 Rt 4.31 min.

$^1$H NMR (400 MHz, DMSO-d6) 2.62 (s, 3H) 2.73 (s, 3H) 3.85 (q, J=5.50 Hz, 2H) 4.92 (t, J=5.50 Hz, 1H) 4.98 (t, J=5.50 Hz, 2H) 7.29 (br. s., 2H) 7.62 (d, J=8.61 Hz, 1H) 8.01 (d, J=8.61 Hz, 1H) 9.28 (s, 1H).

HRMS (ESI) calcd for $C_{15}H_{17}N_4O_2S$ $[M+H]^+$ 317.1067 found 317.1064.

Operating in an analogous way, the following compounds were prepared:

8-methyl-2-(methylsulfanyl)-9-(propan-2-yl)-9H-pyrrolo[3,2-h]quinazoline-7-carboxamide [(I), R1=methyl, X=—S—, R2=$NH_2$, R3=is-propyl, R4=methyl, A=—CH=CH—] (cmpd 30)

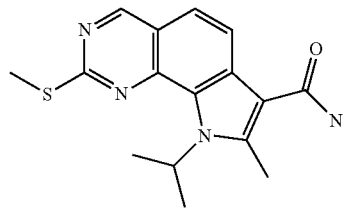 [SMILES: CSc1ncc2ccc3c(C(N)=O)c(C)n(C(C)C)c3c2n1]

LC/MS (254 nm) HPLC method 2 Rt 6.1 min.

$^1$H NMR (400 MHz, DMSO-d6) δ 1.54-1.93 (m, 6H) 2.63 (s, 3H) 2.79 (s, 3H) 4.96-5.10 (m, 1H) 7.35 (br. s., 2H) 7.57-7.68 (m, 1H) 7.90-8.04 (m, 1H) 9.28 (s, 1H).

HRMS (ESI) calcd for $C_{16}H_{19}N_4OS$ $[M+H]^+$ 315.1274 found 315.1281.

9-ethyl-2-(methylsulfanyl)-9H-pyrrolo[3,2-h]quinazoline-7-carboxamide [(I), R1=methyl, X=—S—, R2=$NH_2$, R3=ethyl, R4=H, A=—CH=CH—] (cmpd 31)

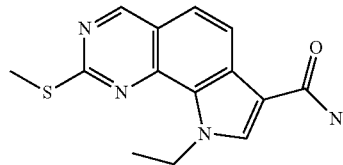 [SMILES: CCn1cc(C(N)=O)c2ccc3cnc(SC)nc3c21]

LC/MS (254 nm) HPLC method 2 Rt 4.13 min.

$^1$H NMR (600 MHz, DMSO-d6) δ 1.51 (t, J=7.14 Hz, 3H) 2.66 (s, 3H) 4.94 (q, J=7.14 Hz, 2H) 7.02 (br. s., 1H) 7.56 (br. s., 1H) 7.65 (d, J=8.61 Hz, 1H) 8.28 (s, 1H) 8.41 (d, J=8.61 Hz, 1H) 9.32 (s, 1H).

HRMS (ESI) calcd for $C_{14}H_{15}N_4OS$ $[M+H]^+$ 287.0961; 287.0961.

Example 21 (Conv. 23)

tert-butyl {cis-4-[7-carbamoyl-2-(methylsulfanyl)-9H-pyrrolo[3,2-h]quinazolin-9-yl]cyclohexyl}carbamate [(I), R1=methyl, X=—S—, R2=$NH_2$, R3=cis 4-[(tert-butoxycarbonyl)amino]cyclohexyl, R4=H, A=—CH=CH—]

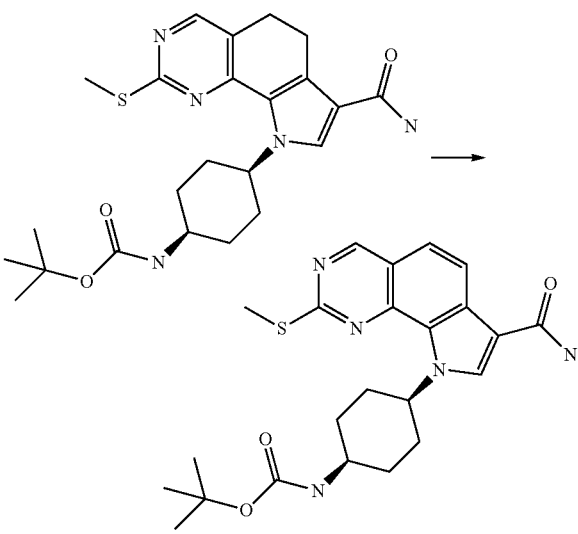

A solution of tert-butyl {cis-4-[7-carbamoyl-2-(methylsulfanyl)-5,6-dihydro-9H-pyrrolo[3,2-h]quinazolin-9-yl]cyclohexyl}carbamate 15 mg (0.032 mmol) and 15 mg (0.064 mmol) of DDQ in chlorobenzene was heated at 140° C. for 2 hours. The volatiles were removed in vacuo, the residue was dissolved with ethyl acetate, and washed with sat. aqueous solution of $NaHCO_3$. The organic phase was dried with $Na_2SO_4$, filtered and concentrated. The crude material was purified by silica gel column chromatography eluting with DCM/MeOH (97:3) yielding the title compound 10 mg (71%).

LC/MS (254 nm) HPLC method 2 Rt 5.72 min.

Example 22 (Conv. 24)

methyl 2-(methylsulfanyl)-9-(piperidin-4-yl)-6,9-dihydro-5H-pyrrolo[3,2-h]quinazoline-7-carboxylate hydrochloride [(I), R1=methyl, X=—S—, R2=—O-methyl, R3=piperidin-4-yl, R4=H, A=—$CH_2CH_2$—]

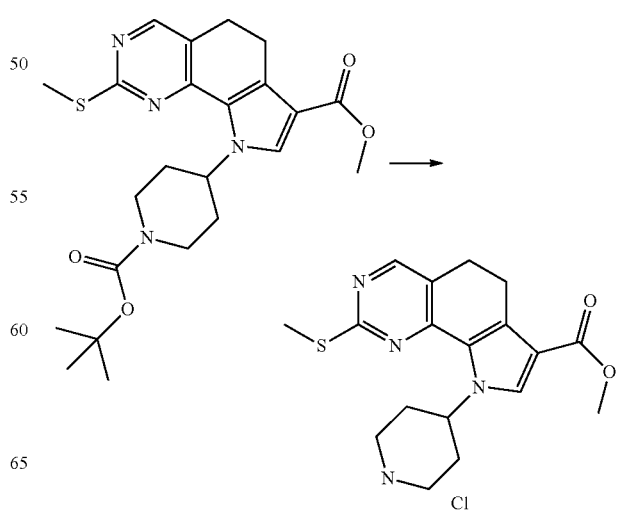

Methyl 9-[1-(tert-butoxycarbonyl)piperidin-4-yl]-2-(methylsulfanyl)-6,9-dihydro-5H-pyrrolo[3,2-h]quinazoline-7-carboxylate 10 mg (0.021 mmol) was dissolved in 1,4 dioxane (2 mL) and 4 M HCl in 1,4-dioxane 3 mL (3 mmol) was added. The mixture was stirred at room temperature for 1 h. The volatiles were removed in vacuo and the obtained residue was triturated with diethyl ether, filtered and dried, to afford the title compound 8 mg (97%).

LC/MS (254 nm) HPLC method 2 Rt 3.64 min.
$^1$H NMR (600 MHz, DMSO-d6) δ 82.08-2.19 (m, 2H) 2.22-2.29 (m, 2H) 2.54 (s, 3H) 2.81 (t, J=7.88 Hz, 2H) 2.97 (t, J=7.88 Hz, 2H) 2.99-3.03 (m, 2H) 3.44-3.51 (m, 2H) 3.75 (s, 3H) 5.51-5.59 (m, 1H) 7.71 (s, 1H) 8.38 (s, 1H) 8.78 (br. s., 1H) 8.83 (br. s., 1H).

HRMS (ESI) calcd for $C_{18}H_{24}N_4O_2S$ [M+H]$^+$ 359.1536 found 359.1531.

Operating in an analogous way, the following compounds were prepared:

2-(methylsulfanyl)-9-(piperidin-4-yl)-6,9-dihydro-5H-pyrrolo[3,2-h]quinazoline-7-carboxamide hydrochloride [(I), R1=methyl, X=—S—, R2=NH$_2$, R3=piperidin-4-yl, R4=H, A=—CH$_2$CH$_2$—] (cmpd 32)

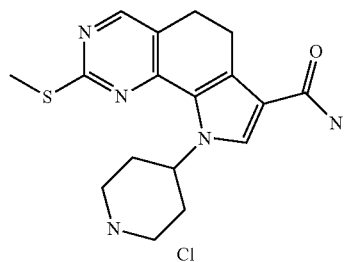 [SMILES: CSc1ncc2c(n1)-c1c(c(C(N)=O)cn1C1CCNCC1)CC2 ; Cl]

LC/MS (254 nm) HPLC method 2 Rt 3.61 min.
$^1$H NMR (600 MHz, DMSO-d6) δ 1.91-2.11 (m, 2H) 2.23-2.32 (m, 2H) 2.53 (s, 3H) 2.76 (t, J=7.60 Hz, 2H) 2.89-3.06 (m, 4H) 3.45-3.56 (m, 2H) 5.40-5.50 (m, 1H) 6.89 (br. s., 1H) 7.45 (br. s., 1H) 7.83 (s, 1H) 8.33 (s, 1H) 8.85 (br. s., 2H).

HRMS (ESI) calcd for $C_{17}H_{23}N_5OS$ [M+H]$^+$ 344.154 found 344.1544.

9-(cis 4-aminocyclohexyl)-2-(methylsulfanyl)-6,9-dihydro-5H-pyrrolo[3,2-h]quinazoline-7-carboxamide hydrochloride [(I), R1=methyl, X=—S—, R2=NH$_2$, R3=cis 4-aminocyclohexyl, R4=H, A=—CH$_2$CH$_2$—] (cmpd 33)

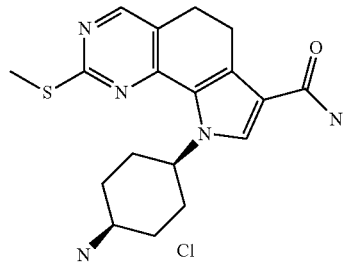 [SMILES: CSc1ncc2c(n1)-c1c(c(C(N)=O)cn1[C@H]1CC[C@@H](N)CC1)CC2 ; Cl]

LC/MS (254 nm) HPLC method 2 Rt 3.91 min.
$^1$H NMR (600 MHz, DMSO-d6) δ 1.72-1.86 (m, 2H) 1.89-2.01 (m, 4H) 2.01-2.13 (m, 2H) 2.76 (t, J=7.70 Hz, 2H) 2.94 (t, J=7.70 Hz, 2H) 3.43-3.54 (m, 1H) 5.31-5.44 (m, 1H) 6.93 (br. s., 1H) 7.16 (br. s., 1H) 8.00 (s, 1H) 8.08 (br. s., 3H) 8.30 (s, 1H).

HRMS (ESI) calcd for $C_{18}H_{24}N_5OS$ [M+H]$^+$ 358.1696 found 358.1694.

9-(cis-4-aminocyclohexyl)-2-(methylsulfanyl)-9H-pyrrolo[3,2-h]quinazoline-7-carboxamide [(I), R1=methyl, X=—S—, R2=NH$_2$, R3=cis 4-aminocyclohexyl, R4=H, A=—CH=CH—] (cmpd 34)

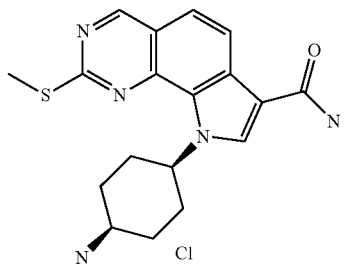 [SMILES: CSc1ncc2ccc3c(C(N)=O)cn([C@H]4CC[C@@H](N)CC4)c3c2n1 ; Cl]

LC/MS (254 nm) HPLC method 2 Rt 3.15 min.
$^1$H NMR (600 MHz, DMSO-d6) δ 1.85-1.96 (m, 2H) 2.00-2.07 (m, 2H) 2.07-2.14 (m, 2H) 2.17-2.29 (m, 2H) 2.68 (s, 3H) 3.51-3.58 (m, 1H) 6.01-6.11 (m, 1H) 7.11 (br. s., 1H) 7.54 (br. s., 1H) 7.67 (d, J=8.61 Hz, 1H) 8.13 (br. s., 3H) 8.38 (d, J=8.61 Hz, 1H) 8.64 (s, 1H) 9.33 (s, 1H).

HRMS (ESI) calcd for $C_{18}H_{22}N_5OS$ [M+H]$^+$ 356.1696 found 356.1694.

9-(3-amino-2,2-dimethylpropyl)-2-(methylsulfanyl)-9H-pyrrolo[3,2-h]quinazoline-7-carboxamide hydrochloride [(I), R1=methyl, X=—S—, R2=NH$_2$, R3=3-amino-2,2-dimethylpropyl, R4=H, A=—CH=CH—] (cmpd 38)

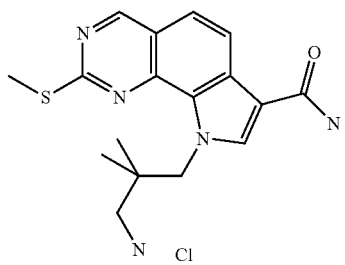 [SMILES: CSc1ncc2ccc3c(C(N)=O)cn(CC(C)(C)CN)c3c2n1 ; Cl]

LC/MS (254 nm) HPLC method 2 Rt 3.89 min.
$^1$H NMR (600 MHz, DMSO-d6) δ 9.35 (s, 1H), 8.47 (d, J=8.61 Hz, 1H), 8.28 (s, 1H), 7.83 (br. s., 4H), 7.69 (d, J=8.79 Hz, 1H), 7.08 (br. s., 1H), 5.11 (s, 2H), 2.76 (d, J=5.86 Hz, 2H), 2.71 (s, 3H), 1.02-1.07 (m, 6H). HRMS (ESI) calcd for $C_{17}H_{22}N_5OS$ [M+H]$^+$ 344.1540 found 344.1544.

9-(azepan-3-yl)-2-(methylsulfanyl)-9H-pyrrolo[3,2-h]quinazoline-7-carboxamide hydrochloride [(I), R1=methyl, X=—S—, R2=NH$_2$, R3=azepan-3-yl, R4=H, A=—CH=CH—] (cmpd 39)

85

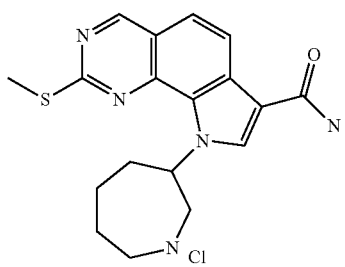 [SMILES: CSc1ncc2ccc3c(C(N)=O)cn(C4CCCCNC4)c3c2n1 ; Cl]

LC/MS (254 nm) HPLC method 2 Rt 3.82 min.

¹H NMR (600 MHz, DMSO-d6) δ 9.34 (s, 1H), 8.80-9.09 (m, 2H), 8.50 (s, 1H), 8.43 (d, J=8.61 Hz, 1H), 7.72-7.75 (m, 1H), 7.67 (d, J=8.61 Hz, 1H), 6.90-7.17 (m, 1H), 6.26 (br. s., 1H), 3.21 (m, 2H), 2.69 (s, 3H), 2.32-2.46 (m, 3H), 2.07-2.11 (m, 2H), 1.91 (m, 1H).

HRMS (ESI) calcd for $C_{18}H_{22}N_5OS$ [M+H]⁺ 356.1540 found 356.1538.

2-amino-9-(piperidin-4-yl)-6,9-dihydro-5H-pyrrolo[3,2-h]quinazoline-7-carboxamide hydrochloride [(I), R1=H, X=—NH—, R2=NH₂, R3=piperidin-4-yl, R4=H, A=—CH₂CH₂—]

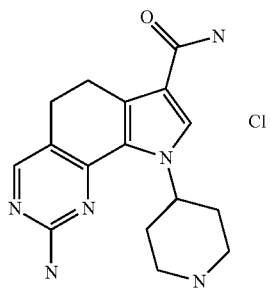 [SMILES: NC(=O)c1cn(C2CCNCC2)c2c1CCc1cnc(N)nc1-2 ; Cl]

¹H NMR (600 MHz, DMSO-d6) d ppm 1.95-2.11 (m, 2H) 2.22-2.33 (m, 2H) 2.53 (s, 3H) 2.76 (t, J=7.60 Hz, 1H) 2.89-3.06 (m, 4H) 3.45-3.55 (m, 2H) 5.40-5.50 (m, 1H) 6.89 (br. s., 1H) 7.45 (br. s., 1H) 7.83 (s, 1H) 8.33 (s, 1H) 8.85 (br. s., 2H)

HRMS (ESI) calcd for $C_{18}H_{22}N_5O$ [M+H]⁺ 344.1540. found 344.1544.

2-(methylsulfanyl)-9-(piperidin-4-yl)-9H-pyrrolo[3,2-h]quinazoline-7-carboxamide [(I), R1=methyl, X=—S—, R2=NH₂, R3=piperidin-4-yl, R4=H, A=—CH=CH—] (cmpd 35)

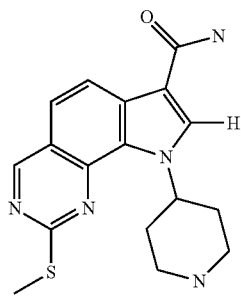 [SMILES: CSc1ncc2ccc3c(C(N)=O)cn(C4CCNCC4)c3c2n1]

86

1H NMR (600 MHz, DMSO-d6) d ppm 1.80-1.94 (m, 2H) 2.11-2.19 (m, 2H) 2.71 (s, 3H) 2.72-2-80 (m, 2H) 3.15-3.24 (m, 2H) 6.07-6-17 (m, 1H) 7.01 (br. s., 1H) 7.63 (br. s., 1H) 7.66 (d, J=8.61 Hz, 1H) 8.45 (d, J=8.61 Hz, 1H) 8.55 (s, 1H) 9.32 (s, 1H)

HRMS (ESI) calcd for $C_{18}H_{22}N_5O$ [M+H]⁺ 245.1033. found 245.1041.

Example 23 (Step G)

methyl 2-methyl-6,9-dihydro-5H-pyrrolo[3,2-h]quinazoline-7-carboxylate [(I), R1=methyl, X=single bond, R2=—O-methyl, R3=H, R4=H, A=—CH₂CH₂—]

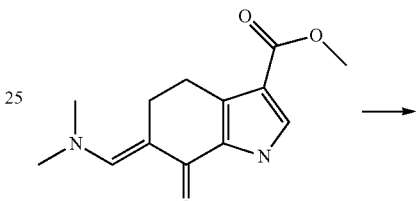

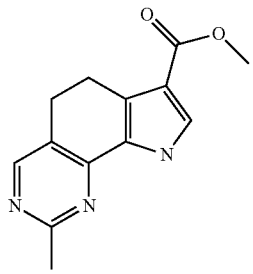

To a solution of methyl (6E)-6-[(dimethylamino)methylidene]-7-oxo-4,5,6,7-tetrahydro-1H-indole-3-carboxylate (50 mg, 0.2 mmol) in DMF (4 mL) acetamidine hydrochloride (190 mg, 2.0 mmol) and K₂CO₃ (275 mg, 2.0 mmol) were added and the mixture was heated at 180° C. for 1 h under microwave irradiation. Volatiles were removed in vacuo, the residue was dissolved with DCM, and washed with H₂O. The organic phase was dried with Na₂SO₄, filtered and concentrated. The crude material was purified by silica gel column chromatography eluting with DCM/MeOH (10:1) yielding the title compound 20 mg (40%) as a dark yellow solid.

1H NMR (600 MHz, DMSO-d6) d ppm 2.55 (s, 3H) 2.85-2.90 (m, 2H) 2.96-2.99 (m, 2H) 3.72 (s, 3H) 7.50 (s, 1H) 8.35 (s, 1H) 12.40 (br. s., 1H)

HRMS (ESI) calcd for $C_{18}H_{22}N_5O$ [M+H]$^+$ 244.1081. found 244.1087.

Example 24 (Step G)

methyl 2-amino-9-[1-(tert-butoxycarbonyl)piperidin-4-yl]-6,9-dihydro-5H-pyrrolo[3,2-h]quinazoline-7-carboxylate [(I), R1=H, X=—NH—, R2=—O-methyl, R3=1-(tert-butoxycarbonyl)piperidin-4-yl, R4=H, A=—CH$_2$CH$_2$—]

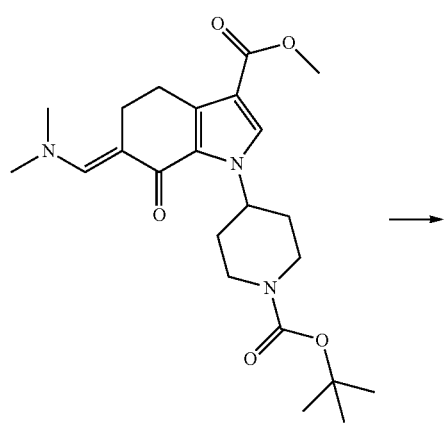

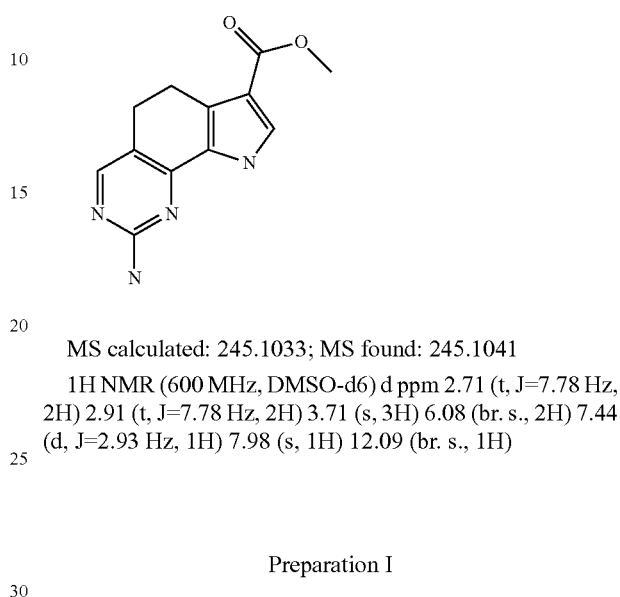

Operating in an analogous way, the following compound was prepared:

methyl 2-amino-6,9-dihydro-5H-pyrrolo[3,2-h]quinazoline-7-carboxylate [(I), R1=H, X=—NH—, R2=—O-methyl, R3=H, R4=H, A=—CH$_2$CH$_2$—]

MS calculated: 245.1033; MS found: 245.1041

1H NMR (600 MHz, DMSO-d6) d ppm 2.71 (t, J=7.78 Hz, 2H) 2.91 (t, J=7.78 Hz, 2H) 3.71 (s, 3H) 6.08 (br. s., 2H) 7.44 (d, J=2.93 Hz, 1H) 7.98 (s, 1H) 12.09 (br. s., 1H)

Preparation I methyl 2-(methylsulfanyl)-8-iodo-9H-pyrrolo[3,2-h]quinazoline-7-carboxylate [(I), R1=methyl, X=—S—, R2=—O-methyl, R3=H, R4=I, A=—CH=CH—]

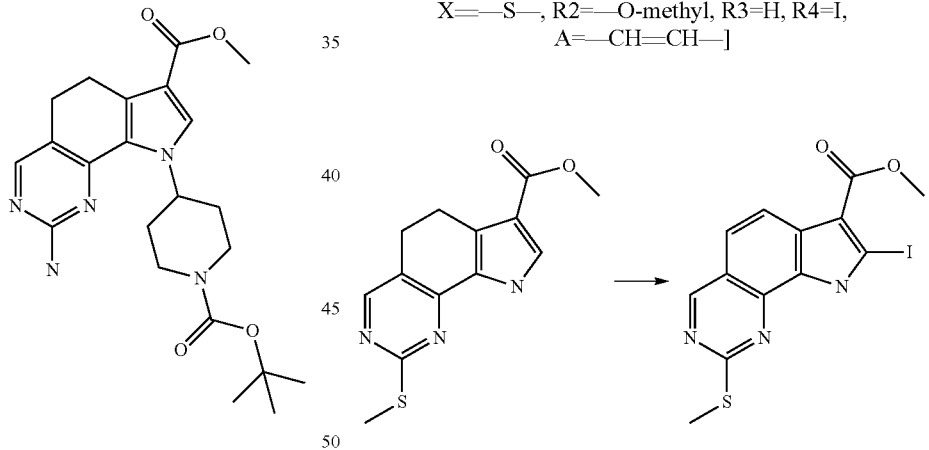

To a solution of methyl (6E)-1-[1-(tert-butoxycarbonyl)piperidin-4-yl]-6-[(dimethylamino)methylidene]-7-oxo-4,5,6,7-tetrahydro-1H-indole-3-carboxylate (10 mg, 0.023 mmol) in DMF (1 mL) guanidine carbonate (10 mg, 0.055 mmol) was added. The mixture was stirred at 110° C. for 8 hours. The resulting mixture was cooled at room temperature and evaporated to dryness. The crude solid was purified by flash chromatography on silica gel (eluant: AcOEt) to afford 8 mg (yield: 80%) of the title compound as a brown solid.

MS calculated: 428.2293; MS found: 428.2292

1H NMR (401 MHz, DMSO-d6) d ppm 1.43 (s, 9H) 1.66-1.84 (m, 2H) 1.92-2.04 (m, 2H) 2.62-2.69 (m, 2H) 2.86-2.92 (m, 2H) 2.92-3.10 (m, 2H) 3.71 (s, 3H) 3.98-4.07 (m, 2H) 5.59-5.72 (m, 1H) 6.28 (s, 2H) 7.72 (s, 1H) 7.99 (s, 1H)

To a solution of methyl 2-(methylsulfanyl)-6,9-dihydro-5H-pyrrolo[3,2-h]quinazoline-7-carboxylate (100 mg, 0.363 mmol) in DMF (5 mL) N-iodosuccinimide (3.25 mg, 1.44 mmol) was added and the mixture was stirred at room temperature for 24 h. Volatiles were removed in vacuo, the residue was dissolved with DCM and washed with H$_2$O. The organic phase was dried with Na$_2$SO$_4$, filtered and concentrated. The crude material was purified by silica gel column chromatography eluting with Hexane/AcOEt (4:2) yielding the title compound 85 mg (60%) as a yellow solid.

1H NMR (600 MHz, DMSO-d6) d ppm 2.75 (s, 3H) 3.89 (s, 3H) 7.69 (d, J=8.79 Hz, 1H) 8.15 (d, J=8.79 Hz, 1H) 9.35 (s, 1H) 13.75 (s, 1H)

MS calculated: 399.9611; MS found: 399.9610

Example 25 (Conv. 23)

methyl 9-[1-(tert-butoxycarbonyl)piperidin-4-yl]-2-(methylsulfanyl)-9H-pyrrolo[3,2-h]quinazoline-7-carboxylate [(I), R1=methyl, X=—S—, R2=—O-methyl, R3=1-(tert-butoxycarbonyl)piperidin-4-yl, R4=H, A=—CH=CH—]

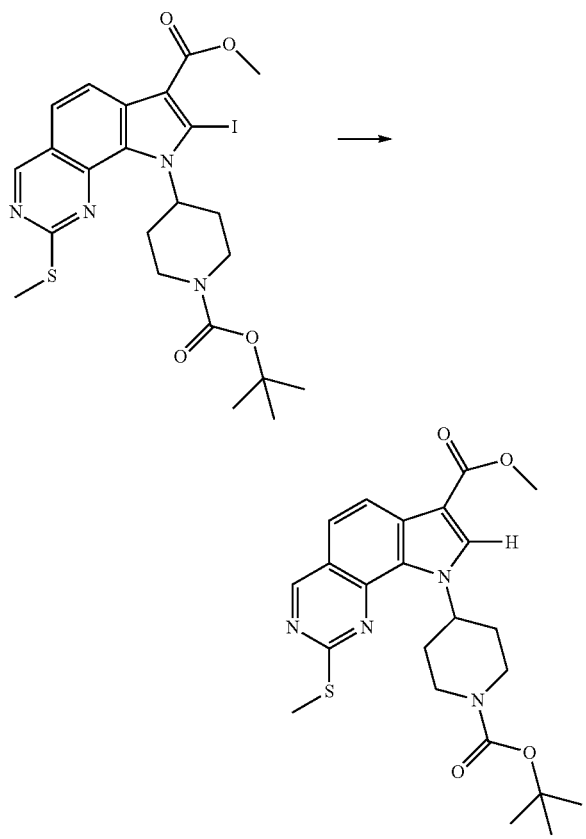

To a solution of methyl 9-[1-(tert-butoxycarbonyl)piperidin-4-yl]-8-iodo-2-(methylsulfanyl)-9H-pyrrolo[3,2-h]quinazoline-7-carboxylate (30 mg, 0.05 mmol) in DMF (2 mL) sodium formiate (7 mg, 10 mmol) and Pd(PPh$_3$)$_4$ (50 mg, 0.004 mmol) were added and the mixture was heated at 120° C. for 3 hours. Volatiles were removed in vacuo. The crude material was purified by silica gel column chromatography eluting with DCM/MeOH (95:5) yielding the title compound 15 mg (65%) as a white solid.

Operating in an analogous way, the following compound was prepared:

methyl 2-(methylsulfanyl)-9H-pyrrolo[3,2-h]quinazoline-7-carboxylate [(I), R1=methyl, X=—S—, R2=—O-methyl, R3=H, R4=H, A=—CH=CH—]

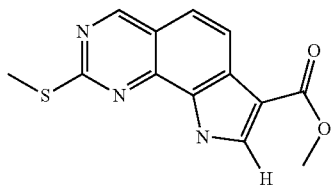 [SMILES: COC(=O)c1c[nH]c2c1ccc1cnc(SC)nc12]

Pharmacology

The compounds of the formula (I) are active as protein kinase inhibitors and are therefore useful, for instance, to restrict the unregulated proliferation of tumour cells.

In therapy, they may be used in the treatment of various tumours, such as those formerly defined, as well as in the treatment of other cell proliferative disorders such as benign prostate hyperplasia, familial adenomatosis polyposis, neurofibromatosis, psoriasis, vascular smooth cell proliferation associated with atherosclerosis, pulmonary fibrosis, arthritis, glomerulonephritis and post-surgical stenosis and restenosis.

The inhibiting activity of putative MPS1 inhibitors and the potency of selected compounds were determined through the assays below described.

The short forms and abbreviations used herein have the following meaning:

Ci Curie
DMSO dimethylsulfoxide
KDa kiloDalton
microCi microCurie
mg milligram
microg microgram
ng nanogram
L liter
mL milliliter
microL microliter
M molar
mM millimolar
microM micromolar
nM nanomolar
Et ethyl Cloning, Expression and Purification of Recombinant MPS1 Full Length Protein.

MPS1 full length (corresponding to residues 2-857 of the full length sequence, see Swiss-Prot accession number P33981) was PCR amplified from the full-length human MPS1 gene present in house as clone pGEX4t_MPS1.

Amplification was performed using the forward oligonucleotide: 5'ggggacaagtttgtacaaaaaagcag-gcttactggaagttctgttccaggggcccgaatccgaggatttaagtggcagag3' and the reverse oligonucleotide: 5'ggggaccactttgtacaa-gaaagctgggttttattttttcccctttttttttcaaaagtcttggaggatgaaga3'].

Both the oligonucleotides are described in WO2009/156315 published on 30 Dec. 2009.

For cloning purposes, the oligonucleotides included attB sites in order to obtain an attB-flanked PCR product suitable for cloning using the Gateway® technology (Invitrogen). Furthermore, for purification purposes, forward primer included a protease cleavage site. The resulting PCR product was cloned in the pDONR201 plasmid and then transferred in the baculovirus expression vector pVL1393GST (Invitrogen) Gateway®-modified. Cloning was performed according to the protocols described in the Gateway® manual.

Baculoviruses were generated by cotransfecting Sf9 insect cells with the expression vector and the viral DNA using the BaculoGold® transfection kit (Pharmingen). Viral supernatant was recovered after 5 days and subjected to 3 rounds of amplification to increase viral titer. Recombinant protein was produced by infecting High5 insect cells. After 72 hours of infection at 21° C., cells were recovered, pelleted and freezed at −80° C. For purification of recombinant protein, pellet was thawed, resuspended in lysis buffer (PBS, NaCl 150 mM, Glycerol 10%, CHAPS 0.1%, DTT 20 mM, protease and phosphatase inhibitors) and lysed by Gaulin. Lysate was cleared by centrifugation and loaded on a GST affinity column. After extensive wash, recombinant protein was cleaved by a specific protease and eluted by incubation.

To get a fully activated enzyme, the protein was then subjected to auto-phosphorylation in presence of ATP 1 mM at 25° C. for 2 hours in kinase buffer (Hepes pH7.5 50 mM, $MgCl_2$ 2.5 mM, $MnCl_2$ 1 mM, DTT 1 mM, phosphatase inhibitors); ATP was then removed whit a desalting column.

Biochemical Assay for Inhibitors of MPS1 Kinase Activity

The inhibitory activity of putative kinase inhibitors and the potency of selected compounds were determined using a trans-phosphorylation assay.

Specific peptide or protein substrates are trans-phosphorylated by their specific ser-thr or tyr kinase in the presence of ATP traced with $^{33}$P-γ-ATP, and in the presence of their own optimal buffer and cofactors.

At the end of the phosphorylation reaction, more than 98% unlabeled ATP and radioactive ATP is captured by an excess of the ion exchange dowex resin; the resin then settles down to the bottom of the reaction plate by gravity. Supernatant is subsequently withdrawn and transferred into a counting plate, then evaluated by β-counting.

Reagents/Assay Conditions i. Dowex Resin Preparation 500 g of wet resin (SIGMA, custom prepared resin DOWEX 1×8 200-400 mesh, 2.5 Kg) are weighed out and diluted to 2 L in 150 mM sodium formate, pH 3.00.

The resin is allowed to settle down (some hours) and then the supernatant is discarded.

After three washes as above over a couple of days, the resin is allowed to settle and two volumes (wrt the resin volume) of 150 mM sodium formate buffer are added.

The pH is then measured and should be around 3.00

The washed resin is stable for more than one week; the stock resin is kept at 4° C. before use.

ii. Kinase Buffer (KB)

The buffer for MPS1 assay was composed of HEPES 50 mM, at pH 7.5, with 2.5 mM $MgCl_2$, 1 mM $MnCl_2$, 1 mM DTT, 3 microM $Na_3VO_4$, 2 mM β-glycerophosphate and 0.2 mg/mL BSA.

iii. Assay Conditions

The assay was run with a final concentration MPS1 of 5 nM, in the presence of 15 microM ATP and 1.5 nM $^{33}$P-γ-ATP; the substrate was P38-βtide, used at 200 microM.

Robotized Dowex Assay

The test mix consisted of:

1) 3× Enzyme mix (done in Kinase Buffer 3×), 5 microL/well
2) 3× substrate and ATP mix (done in ddH2O), together with $^{33}$P-γ-ATP, 5 microL/well
3) 3× test compounds (diluted into ddH2O-3% DMSO)-5 microL/well See below for compound dilution and assay scheme
Compound Dilution and Assay Scheme is Defined Below:
i. Dilution of Compounds Test compounds are received as a 1 mM solution in 100% DMSO, distributed into 96 or 384 well plates:

a) for percent inhibition studies (HTS), individual dilution plates at 1 mM are diluted at a 3× concentration (30 microM) in $ddH_2O$ (3% DMSO=final concentration) using a Beckman NX automated pipetting platform. The same instrument is used for distributing the diluted mother plates into the test plates.

b) for IC50 determination (KSS platform), 100 microL of each compound at 1 mM in 100% DMSO are transferred from the original plate into the first column of another 96 well plate (A1 to G1); well H1 is left empty for the internal standard inhibitor, usually staurosporine.

An automated station for serial dilutions (Biomek FX, Beckman) is used for producing 1:3 dilutions in 100% DMSO, from line A1 to A10, and for all the seven compounds in the column. Moreover, 4-5 copies of daughter plates are prepared by reformatting 5 microL of this first set of 100% DMSO dilution plates into 384 deep well-plates: one copy of the daughter plates with the serial dilutions of test compounds will be thaw the day of the experiments, reconstituted at a 3× concentration with water and used in the IC50 determination assays. In a standard experiment, the highest concentration (3×) of all compounds is 30 microM, while the lowest one is 1.5 nM.

Each 384 well-plate will contain reference wells (total enzyme activity vs. no enzymatic activity) for the Z' and signal to background evaluation.

ii. Assay Scheme 384-well plates, V bottom (test plates) are prepared with 5 microL of the compound dilution (3×) and then placed onto a PlateTrak 12 robotized station (Perkin Elmer; the robot has one 384-tips pipetting head for starting the assay plus one 96-tips head for dispensing the resin) together with one reservoir for the Enzyme mix (3×) and one for the ATP mix (3×).

At the start of the run, the robot aspirates 5 microL of ATP mix, makes an air gap inside the tips (2 microL) and aspirates 5 microL of MPS1 mix. The following dispensation into the plates allows the kinase reaction to start upon 3 cycles of mixing, done by the robot itself.

At this point, the correct concentration is restored for all reagents.

The robot incubates the plates for 60 minutes at room temperature, and then stops the reaction by pipetting 70 microL of dowex resin suspension into the reaction mix. Three cycles of mixing are done immediately after the addition of the resin.

The resin suspension is very dense; in order to avoid tip clogging, wide bore tips are used to dispense it.

Another mixing cycle is performed after all the plates are stopped, this time using normal tips: the plates are then allowed to rest for about one hour in order to maximize ATP capture. At this point, 22 microL of the supernatant are transferred into 384-Optiplates (Perkin-Elmer), with 50 microL of Microscint 40 (Perkin-Elmer); after 5 min of orbital shaking the plates are read on a Perkin-Elmer Top Count radioactivity counter.

iii. Data Analysis

Data are analysed by an internally customized version of the SW package "Assay Explorer" that provides either % inhibition for primary assays or sigmoidal fittings of the tendilutions curves for IC50 determination in the secondary assays/hit confirmation routines.

In Vitro Cell Proliferation Assay

A2780 human ovarian cancer cells, MCF7 human breast cancer cells and MV-4-11 (biphenotypic B myelomonocytic leukemia) cells (1250 cells/well) were seeded in white 384 well-plates in complete medium (RPMI 1640 or EMEM plus 10% Fetal bovine serum) and treated with compounds dissolved in 0.1% DMSO, 24 h after seeding. The cells were incubated at 37° C. and 5% $CO_2$ and after 72 hours the plates were processed using CellTiter-Glo assay (Promega) following the manufacturer's instruction.

CellTiter-Glo is a homogenous method based on the quantification of the ATP present, an indicator of metabolitically active cells. ATP is quantified using a system based on luciferase and D-luciferin resulting into light generation. The luminescent signal is proportional to the number of cells present in culture.

Briefly 25 microL/well of reagent solution were added to each well and, after 5 minutes shacking, microplates were read by Envision (PerkinElmer) luminometer. The luminescent signal was proportional to the number of cells present in culture.

Inhibitory activity was evaluated comparing treated versus control data using Assay Explorer (MDL) program. $IC_{50}$ was calculated using sigmoidal interpolation curve.

Given the above inhibition assays, the compounds of the formula (I) of the invention resulted to possess a good MPS1 inhibitory activity, typically with an $IC_{50}$ in the range between 0.001 and 5 microM.

Moreover, the compounds of the formula (I) of the invention show good cellular proliferation inhibitory activity, typically with an $IC_{50}$ in the range of from 0.010 to 5 μM in A2780 cells.

Biochemical Assay for Inhibitors of PIM-1 Kinase Activity

The inhibitory activity of putative kinase inhibitors and the potency of selected compounds were determined using a trans-phosphorylation assay.

Specific peptide or protein substrates are trans-phosphorylated by their specific ser-thr or tyr kinase in the presence of ATP traced with $^{33}P$-γ-ATP, and in the presence of their own optimal buffer and cofactors.

At the end of the phosphorylation reaction, more than 98% unlabeled ATP and radioactive ATP is captured by an excess of the ion exchange dowex resin; the resin then settles down to the bottom of the reaction plate by gravity.

Supernatant is subsequently withdrawn and transferred into a counting plate, then evaluated by β-counting.

Reagents/Assay Conditions
Dowex Resin Preparation 500 g of wet resin (SIGMA, custom prepared resin DOWEX 1×8 200-400 mesh, 2.5 Kg) are weighed out and diluted to 2 L in 150 mM sodium formate, pH 3.00.

The resin is allowed to settle down (some hours) and then the supernatant is discarded.

After three washes as above over a couple of days, the resin is allowed to settle and two volumes (wrt the resin volume) of 150 mM sodium formate buffer are added.

The pH is then measured and should be around 3.00

The washed resin is stable for more than one week; the stock resin is kept at 4° C. before use.

Kinase Buffer (KB)

The buffer for PIM-1 assay was composed of HEPES 50 mM, at pH 7.5, with 10 mM $MgCl_2$, 1 mM DTT, 3 microM $NaVO_3$, and 0.2 mg/ml BSA Full-length human PIM-1 was expressed and purified as described in Bullock A N, et al., J. Biol. Chem. 2005, 280, 41675-82.

The enzyme showed a linear kinetic after a step of pre-activation by auto-phosphorylation in the following conditions: 1.7 microM PIM1 was incubated 1 hour RT at 28° C. in the presence of 125 microM ATP Assay Conditions ATP concentration: 200 microM $^{33}P$-γ-ATP: 6 nM Enzyme concentration: 1 nM Substrate concentration Aktide (Chemical Abstract Service Registry Number 324029-01-8): 25 microM Robotized Dowex Assay The test mix consisted of:

1) 3× Enzyme mix (done in Kinase Buffer 3×), 5 microL/well
2) 3× substrate and ATP mix (done in $ddH_2O$), together with $^{33}P$-γ-ATP, 5 microL/well
3) 3× test compounds (diluted into ddH2O-3% DMSO-) 5 μmicro/well See below for compound dilution and assay scheme Dilution of Compounds For $IC_{50}$ determination, test compounds are received as a 1 mM solution in 100% DMSO and distributed into 96-well plates: compounds are then plated into the first column of a new 96-well plate (A1 to G1), 100 microL/well.

An automated station (Biomek FX, Beckman) is used for serial dilutions, producing 1:3 dilutions in 100% DMSO, from line A1 to A10, for all the compounds in the column. Moreover, 4-5 copies of daughter plates are prepared by reformatting 5 microL of this first set of 100% DMSO dilution plates into 384-deep well plates: one copy of these serial dilution plates with the test compounds is thawed on the day of study, reconstituted at the working concentration (3-fold the final concentration) with 162 microL/well of water and used for $IC_{50}$ determination assays. In a standard experiment, the highest concentration (3×) of compounds is typically 30 microM, while the lowest one is typically 1.5 nM.

Each 384-well plate generates at least one curve of the standard inhibitor staurosporine and reference wells (total enzyme activity vs. no enzymatic activity) for evaluation of Z' and signal to background (S/B) ratio.

Assay Scheme 384-well plates, V bottom (test plates) are prepared with 5 microL of compound diluted as previously described (3×) and then placed onto a PlateTrak 12 robotized station (Perkin Elmer; the robot has one 384-tip pipetting head for assay start, plus one 96-tip head for dispensing resin) together with one reservoir for Enzyme mix (3×) and one for ATP mix (3×).

Data are analyzed by an internally customized version of the "Assay Explorer" SW package, which provides sigmoidal fitting of the ten-dilution curves for IC50 determination in secondary assay/hit confirmation routines.

Method for PIM-2 Kinase Inhibition Assay: Dowex Technique

Kinase Buffer (KB)

The buffer for PIM-2 assay was composed of HEPES 50 mM, at pH 7.5, with 1 mM $MgCl_2$, 1 mM DTT, 3 microM $Na_3VO_4$, and 0.2 mg/mL BSA Full-length human PIM-2 was expressed and purified as described in Fedorov O, et al., PNAS 2007 104, 51, 20523-28.

Assay Conditions (Final Concentrations)

Enzyme concentration=1.5 nM

Aktide substrate (Chemical Abstract Service Registry Number 324029-01-8)=5 microM ATP=4 microM $^{33}P$-γ-ATP=1 nM Robotized Dowex Assay See above: same procedure as described for PIM-1.

The following Table A reports the experimental data of some representative compounds of the invention of formula (I) being tested on the MPS1, PIM-1 and PIM-2 enzymes in the specific in vitro kinase assays above described (IC$_{50}$ microM).

The following Table A also reports the inhibitory activity of some of the closest compounds of the prior art.

Ref. compound 1, 2, 3 and 4 corresponds respectively to compounds coded M3, N9, N4 and N10 in the patent application WO2008/065054 cited above; these compounds correspond respectively to the third, the fifth, the seventh and the sixth disclaimed compounds of the present invention.

TABLE A

| Compound no. | Name | IC$_{50}$ MPS1 (microM) | IC$_{50}$ PIM-1 (microM) | IC$_{50}$ PIM-2 (microM) |
| --- | --- | --- | --- | --- |
| Ref. cmpound 1 | 2-amino-9-methyl-6,9-dihydro-5H-pyrrolo[3,2-h]quinazoline-7-carboxamide | >10 | >10 | >10 |
| Ref. compound 2 | 2-amino-8-phenyl-9H-pyrrolo[3,2-h]quinazoline-7-carboxamide (N9) | >5 | >5 | >10 |
| Ref. compound 3 | 2-amino-9-methyl-8-phenyl-6,9-dihydro-5H-pyrrolo[3,2-h]quinazoline-7-carboxamide (N4) | >5 | >5 | >10 |
| Ref. compound 4 | 2-amino-9-methyl-8-phenyl-9H-pyrrolo[3,2-h]quinazoline-7-carboxamide (N10) | >5 | >5 | >10 |
| 3 | N-(2,6-diethylphenyl)-2-({2-methoxy-4-[4-(pyrrolidin-1-yl)piperidin-1-yl]phenyl}amino)-8,9-dimethyl-6,9-dihydro-5H-pyrrolo[3,2-h]quinazoline-7-carboxamide | 0.099 | >10 | >10 |
| 7 | 2-{[2-methoxy-4-(4-methylpiperazin-1-yl)phenyl]amino}-8,9-dimethyl-6,9-dihydro-5H-pyrrolo[3,2-h]quinazoline-7-carboxamide | 0.023 | 0.748 | >5 |
| 16 | N-(2,6-diethylphenyl)-2-{[2-methoxy-4-(4-methylpiperazin-1-yl)phenyl]amino}-10-methyl-5,6,7,10-tetrahydropyrrolo[3',2':6,7]cyclohepta[1,2-d]pyrimidine-8-carboxamide | 0.132 | >10 | >10 |
| 22 | 2-(methylsulfanyl)-9-(propan-2-yl)-6,9-dihydro-5H-pyrrolo[3,2-h]quinazoline-7-carboxamide | 0.382 | 0.016 | 0.024 |
| 25 | 9-(2-hydroxyethyl)-2-(methylsulfanyl)-6,9-dihydro-5H-pyrrolo[3,2-h]quinazoline-7-carboxamide | 2.443 | 0.133 | 0.540 |
| 29 | 9-(2-hydroxyethyl)-8-methyl-2-(methylsulfanyl)-9H-pyrrolo[3,2-h]quinazoline-7-carboxamide | 2.940 | 0.087 | 0.408 |
| 30 | 8-methyl-2-(methylsulfanyl)-9-(propan-2-yl)-9H-pyrrolo[3,2-h]quinazoline-7-carboxamide | 0.622 | 0.004 | 0.012 |
| 32 | 2-(methylsulfanyl)-9-(piperidin-4-yl)-6,9-dihydro-5H-pyrrolo[3,2-h]quinazoline-7-carboxamide | >10 | 0.074 | 0.159 |
| 33 | 9-(cis 4-aminocyclohexyl)-2-(methylsulfanyl)-6,9-dihydro-5H-pyrrolo[3,2-h]quinazoline-7-carboxamide | 1.550 | 0.005 | 0.007 |
| 34 | 9-(cis-4-aminocyclohexyl)-2-(methylsulfanyl)-9H-pyrrolo[3,2-h]quinazoline-7-carboxamide | 0.855 | 0.0008 | 0.001 |
| 35 | 2-(methylsulfanyl)-9-(piperidin-4-yl)-9H-pyrrolo[3,2-h]quinazoline-7-carboxamide | 4.552 | 0.007 | 0.023 |
| 36 | 2-(methylsulfanyl)-9H-pyrrolo[3,2-h]quinazoline-7-carboxamide | 0.814 | 0.013 | 0.046 |
| 38 | 9-(3-amino-2,2-dimethylpropyl)-2-(methylsulfanyl)-9H-pyrrolo[3,2-h]quinazoline-7-carboxamide hydrochloride | 2.944 | 0.024 | 0.034 |

The invention claimed is:
1. A compound of formula (I):

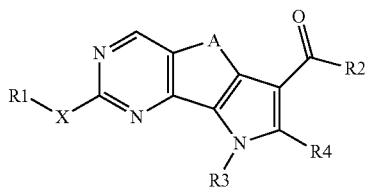

wherein
R1 is hydrogen, halogen or an optionally substituted group selected from amino, straight or branched $C_1$-$C_6$ alkyl, $C_3$-$C_7$ cycloalkyl, cycloalkyl-alkyl, aryl, arylalkyl, heterocyclyl and heterocyclylalkyl;
R2 is a group selected from —NHR" and —N(OR''')R" wherein R" and R''' are, each independently, hydrogen or an optionally substituted group selected from straight or branched $C_1$-$C_6$ alkyl, $C_3$-$C_7$ cycloalkyl, cycloalkyl-alkyl, aryl, arylalkyl, heterocyclyl and heterocyclylalkyl;
R3 is hydrogen or optionally substituted group selected from straight or branched $C_1$-$C_6$ alkyl, $C_3$-$C_7$ cycloalkyl, cycloalkyl-alkyl, aryl, arylalkyl, heterocyclyl and heterocyclylalkyl;
R4 is hydrogen or an optionally substituted group selected from straight or branched $C_1$-$C_6$ alkyl, $C_3$-$C_7$ cycloalkyl, cycloalkyl-alkyl, aryl, arylalkyl, heterocyclyl and heterocyclylalkyl;
X is a group selected from —NR'—, —O— and —S—, wherein R' is hydrogen or an optionally substituted group selected from straight or branched $C_1$-$C_6$ alkyl, $C_3$-$C_7$ cycloalkyl, cycloalkyl-alkyl, aryl, arylalkyl, heterocyclyl and heterocyclylalkyl or, together with the nitrogen atom to which they are bound, R1 and R' may form a 5 to 6 membered heteroaryl or heterocyclyl group optionally containing one additional heteroatom selected from N, O and S;
A is a group selected from —(CH$_2$)$_2$—, —CH═CH—, —C(CH$_3$)$_2$—CH$_2$— and —CH$_2$—C(CH$_3$)$_2$;
or a pharmaceutically acceptable salt thereof,
with the proviso that the following compounds are excluded:
2-amino-9-methyl-6,9-dihydro-5H-pyrrolo[3,2-h]quinazoline-7-carboxamide,
2-amino-8-phenyl-9H-pyrrolo[3,2-h]quinazoline-7-carboxamide,
2-amino-9-methyl-8-phenyl-9H-pyrrolo[3,2-h]quinazoline-7-carboxamide and
2-amino-9-methyl-8-phenyl-6,9-dihydro-5H-pyrrolo[3,2-h]quinazoline-7-carboxamide.

2. A compound of formula (I) as defined in claim 1 wherein: X is a group —NR'—; R2 is a group —NHR" or —N(OR''')R", wherein R" is hydrogen or an optionally substituted group selected from straight or branched $C_1$-$C_4$ alkyl group and aryl; and R1 is an optionally substituted group selected from straight or branched $C_1$-$C_6$ alkyl, $C_3$-$C_7$ cycloalkyl, cycloalkyl-alkyl, aryl, arylalkyl, heterocyclyl and heterocyclylalkyl.

3. A compound of formula (I) as defined in claim 1 wherein:
X is a group —O—; R2 is a group —NHR" or —N(OR''')R", wherein R" is hydrogen or an optionally substituted group selected from straight or branched $C_1$-$C_4$ alkyl and aryl; and R1 is an optionally substituted group selected from straight or branched $C_1$-$C_6$ alkyl, $C_3$-$C_7$ cycloalkyl, cycloalkyl-alkyl, aryl, arylalkyl, heterocyclyl and heterocyclylalkyl.

4. A compound of formula (I) as defined in claim 1 wherein: X is a group —S—; R2 is a group —NHR" or —N(OR''')R", wherein R" is hydrogen or an optionally substituted group selected from straight or branched $C_1$-$C_4$ alkyl and aryl; and R1 is an optionally substituted group selected from straight or branched $C_1$-$C_6$ alkyl, $C_3$-$C_7$ cycloalkyl, cycloalkyl-alkyl, aryl, arylalkyl, heterocyclyl and heterocyclylalkyl.

5. A compound of formula (I) or a pharmaceutically acceptable salt thereof as defined in claim 1 which is selected from the group consisting of:
N-(2,6-diethylphenyl)-9-(methoxymethyl)-2-{[2-methoxy-4-(4-methylpiperazin-1-yl)phenyl]amino}-8-methyl-6,9-dihydro-5H-pyrrolo[3,2-h]quinazoline-7-carboxamide,
2-[(4-bromo-2-methoxyphenyl)amino]-N-(2,6-diethylphenyl)-8,9-dimethyl-6,9-dihydro-5H-pyrrolo[3,2-h]quinazoline-7-carboxamide,
N-(2,6-diethylphenyl)-2-({2-methoxy-4-[4-(pyrrolidin-1-yl)piperidin-1-yl]phenyl}amino)-8,9-dimethyl-6,9-dihydro-5H-pyrrolo[3,2-h]quinazoline-7-carboxamide,
N-(2,6-diethylphenyl)-2-({4-[4-(dimethylamino)piperidin-1-yl]-2-methoxyphenyl}amino)-8,9-dimethyl-6,9-dihydro-5H-pyrrolo[3,2-h]quinazoline-7-carboxamide,
N-(2,6-diethylphenyl)-2-{[2-methoxy-4-(4-methylpiperazin-1-yl)phenyl]amino}-8,9-dimethyl-6,9-dihydro-5H-pyrrolo[3,2-h]quinazoline-7-carboxamide,
N-(2,6-diethylphenyl)-2-({4-[4-(2-hydroxyethyl)piperazin-1-yl]-2-methoxyphenyl}amino)-8,9-dimethyl-6,9-dihydro-5H-pyrrolo[3,2-h]quinazoline-7-carboxamide,
2-{[2-methoxy-4-(4-methylpiperazin-1-yl)phenyl]amino}-8,9-dimethyl-6,9-dihydro-5H-pyrrolo[3,2-h]quinazoline-7-carboxamide,
2-[(4-bromo-2-methoxyphenyl)amino]-N-(2,6-diethylphenyl)-9-methyl-6,9-dihydro-5H-pyrrolo[3,2-h]quinazoline-7-carboxamide,
N-(2,6-diethylphenyl)-2-{[2-methoxy-4-(4-methylpiperazin-1-yl)phenyl]amino}-9-methyl-6,9-dihydro-5H-pyrrolo[3,2-h]quinazoline-7-carboxamide,
N-(2,6-diethylphenyl)-2-({4-[4-(dimethylamino)piperidin-1-yl]-2-methoxyphenyl}amino)-9-methyl-6,9-dihydro-5H-pyrrolo[3,2-h]quinazoline-7-carboxamide,
N-(2,6-diethylphenyl)-2-({2-methoxy-4-[4-(pyrrolidin-1-yl)piperidin-1-yl]phenyl}amino)-9-methyl-6,9-dihydro-5H-pyrrolo[3,2-h]quinazoline-7-carboxamide,
N-(2,6-diethylphenyl)-2-{(4-[3-(dimethylamino)propyl](methyl)amino}-2-methoxyphenyl)amino]-9-methyl-6,9-dihydro-5H-pyrrolo[3,2-h]quinazoline-7-carboxamide,
N-(2,6-diethylphenyl)-2-({4-[4-(2-hydroxyethyl)piperazin-1-yl]-2-methoxyphenyl}amino)-9-methyl-6,9-dihydro-5H-pyrrolo[3,2-h]quinazoline-7-carboxamide,
2-[(4-bromo-2-methoxyphenyl)amino]-N-[(1S)-2-(1,3-dioxo-1,3-dihydro-2H-isoindol-2-yl)-1-phenylethyl]-9-methyl-6,9-dihydro-5H-pyrrolo[3,2-h]quinazoline-7-carboxamide,
2-[(4-bromo-2-methoxyphenyl)amino]-N-(2,6-diethylphenyl)-10-methyl-5,6,7,10-tetrahydropyrrolo[3',2':6,7]cyclohepta[1,2-d]pyrimidine-8-carboxamide, 8-methyl-2-(methylsulfanyl)-9-(propan-2-yl)-6,9-dihydro-5H-pyrrolo[3,2-h]quinazoline-7-carboxamide, 8-methyl-2-(methylsulfanyl)-6,9-dihydro-5H-pyrrolo[3,2-h]quinazoline-7-carboxamide, 2-(methylsulfanyl)-6,9-dihydro-5H-pyrrolo[3,2-h]quinazoline-7-carboxamide, 2-(methylsulfanyl)-9-(propan-2-yl)-6,9-dihydro-5H-pyrrolo[3,2-h]quinazoline-7-carboxamide, 2-(dimethylamino)-8-methyl-6,9-dihydro-5H-pyrrolo[3,2-h]quinazoline-7-carboxamide, 9-(2-hydroxyethyl)-8-methyl-2-(methylsulfanyl)-6,9-dihydro-5H-pyrrolo[3,2-h]quinazoline-7-carboxamide, 9-(2-hydroxyethyl)-2-(methylsulfanyl)-6,9-dihydro-5H-pyrrolo[3,2-h]quinazoline-7-carboxamide, 2-(dimethylamino)-8-methyl-9H-pyrrolo[3,2-h]quinazoline-7-carboxamide, 9-methyl-2-(methylsulfanyl)-9H-pyrrolo[3,2-h]quinazoline-7-carboxamide, 8-methyl-2-(methylsulfanyl)-9H-pyrrolo[3,2-h]quinazoline-7-carboxamide, 9-(2-hydroxyethyl)-8-methyl-2-(methylsulfanyl)-9H-pyrrolo[3,2-h]quinazoline-7-carboxamide, 8-methyl-2-(methylsulfanyl)-9-(propan-2-yl)-9H-pyrrolo[3,2-h]quinazoline-7-carboxamide, 9-ethyl-2-(methylsulfanyl)-9H-pyrrolo[3,2-h]quinazoline-7-carboxamide, 2-(methylsulfanyl)-9-(piperidin-4-yl)-6,9-dihydro-5H-pyrrolo[3,2-h]quinazoline-7-carboxamide, 9-(cis 4-aminocyclohexyl)-2-(methylsulfanyl)-6,9-dihydro-5H-pyrrolo[3,2-h]quinazoline-7-carboxamide, 9-(cis-4-aminocyclohexyl)-2-(methylsulfanyl)-9H-pyrrolo[3,2-h]quinazoline-7-carboxamide, 2-(methylsulfanyl)-9-(piperidin-4-yl)-9H-pyrrolo[3,2-h]quinazoline-7-carboxamide, 2-(methylsulfanyl)-9H-pyrrolo[3,2-h]quinazoline-7-carboxamide, 2-methyl-6,9-dihydro-5H-pyrrolo[3,2-h]quinazoline-7-carboxamide, 9-(3-amino-2,2-dimethylpropyl)-2-(methylsulfanyl)-9H-pyrrolo[3,2-h]quinazoline-7-carboxamide hydrochloride and 9-(azepan-3-yl)-2-(methylsulfanyl)-9H-pyrrolo[3,2-h]quinazoline-7-carboxamide hydrochloride.

6. A process for preparing a compound of formula (I) as defined in claim 1 or a pharmaceutically acceptable salt thereof wherein the process comprises the following steps:

st.A) reacting a compound of formula (II)

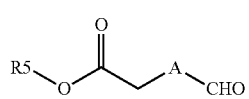

(II)

wherein A is as defined in claim 1 except —CH=CH— and R5 is an optionally substituted $C_1$-$C_6$ alkyl with a compound of formula (III)

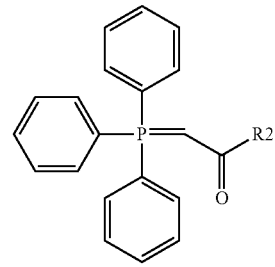

(III)

wherein R2 is an optionally substituted alkoxy;

st.B) reacting the resultant compound of the formula (IV):

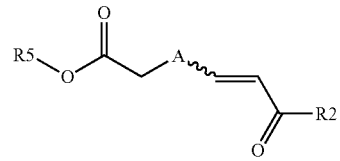

(IV)

wherein R2 is an optionally substituted alkoxy, R5 is an optionally substituted $C_1$-$C_6$ alkyl and A is as defined in claim 1 except —CH=CH—, with toluenesulfonylmethyl isocyanide in presence of a strong base;

st.C) hydrolyzing selectively in acidic or basic condition the resultant compound of formula (V)

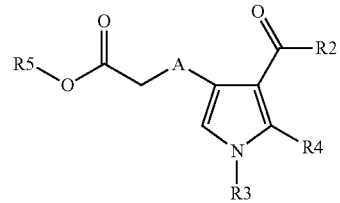

(V)

wherein R3 and R4 are hydrogen, A is as defined in claim 1 except —CH=CH—, R2 is an optionally substituted alkoxy and R5 is an optionally substituted $C_1$-$C_6$ alkyl so to obtain a compound of formula (VI)

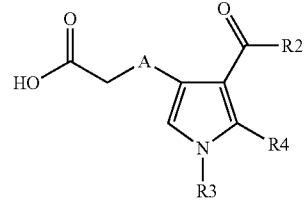

(VI)

wherein R3 and R4 are hydrogen, A is as defined in claim 1 except —CH—CH—, and R2 is an optionally substituted alkoxy;

alternatively, st.Ca) a compound of formula (VI) wherein R3 is hydrogen, R4 is as defined in claim 1 except hydrogen, A is as defined in claim 1 except —CH=CH—, and R2 is an optionally substituted alkoxy, can be obtained reacting a compound of formula (VII)

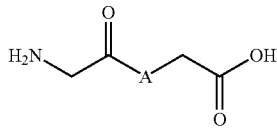
(VII)

wherein A is as defined in claim 1 except —CH=CH— with a compound of formula (VIII)

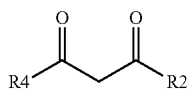
(VIII)

wherein R2 is an optionally substituted alkoxy and R4 is as defined in claim 1 except hydrogen;

st.D) cyclizing the resultant compound of formula (VI) wherein R2 is an optionally substituted alkoxy, R3 is hydrogen, R4 is as defined in claim 1, and A is as defined in claim 1 except —CH=CH—, in acidic condition so as to obtain a compound of formula (IX)

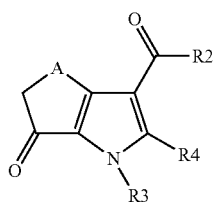
(IX)

wherein R2 is an optionally substituted alkoxy, R3 is hydrogen, R4 is as defined in claim 1, and A is as defined in claim 1 except —CH=CH—;

if needed or desired, st.E) alkylating, a compound of formula (IX) wherein R3 is hydrogen, with a compound of the formula (X):

R3-L (X)

wherein L is a suitable leaving group such as mesyl, tosyl, halogen atom, and R3 is as defined in claim 1 except hydrogen;

st.F) reacting the resultant compound of formula (IX)

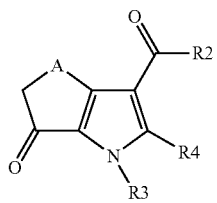
(IX)

wherein R2 is an optionally substituted alkoxy, R3 and R4 are as defined in claim 1, and A is as defined in claim 1 except —CH=CH—, with an N,N-dimethylformamide derivative;

st.G) reacting the resultant compound of formula (XI)

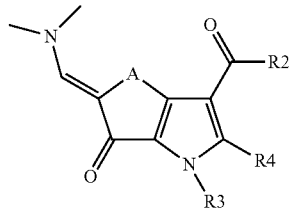
(XI)

wherein R2 is an optionally substituted alkoxy, R3 and R4 are as defined in claim 1, and A is as defined in claim 1 except —CH=CH—, with a compound of formula (XII)

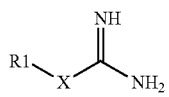
(XII)

wherein X is a single bond or a divalent radical selected from —NR'—, —O— and —S—; and R1 and R' are as defined in claim 1, so as to obtain a compound of formula (Ia):

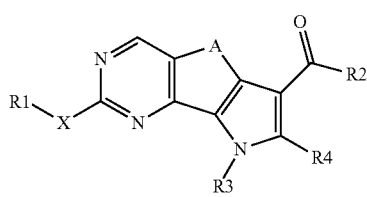
(Ia)

wherein X is a single bond or a divalent radical selected from —NR'—, —O— and —S—; R2 is an optionally substituted alkoxy; A is as defined in claim 1 except —CH=CH—; and R1, R3, R4 and R' are as defined in claim 1; converting the compound of the formula (Ia) into a compound of the formula (I), and, if desired, converting a compound of the formula (I) into a pharmaceutically acceptable salt thereof or converting a salt into the free compound (I).

7. A method for treating a disease caused by and/or associated with a dysregulated protein kinase activity, the disease selected from the group consisting of ovarian cancer, breast cancer, melanoma, colon cancer, leukemia, pancreatic cancer and myeloma, which comprises administering to a mammal in need thereof an effective amount of a compound of formula (I) as defined in claim 1.

8. The method according to claim 7 further comprising subjecting the mammal in need thereof to a radiation therapy or chemotherapy regimen in combination with at least one cytostatic or cytotoxic agent.

9. The method according to claim 7 wherein the mammal in need thereof is a human.

10. An in vitro method for inhibiting kinase protein activity which comprises contacting the said protein with an effective amount of a compound of formula (I) as defined in claim 1, wherein the kinase protein is selected from the group consisting of MPS 1, PIM-1 and PIM-2.

11. The method according to claim 7 which provides tumor angiogenesis and metastasis inhibition.

12. A pharmaceutical composition comprising one or more compounds of the formula (I) or a pharmaceutically acceptable salt thereof, as defined in claim 1, and at least one pharmaceutically acceptable excipient, carrier and/or diluent.

13. A pharmaceutical composition according to claim 12 further comprising one or more chemotherapeutic agents.

14. A product or kit comprising a compound of formula (I) or a pharmaceutically acceptable salt thereof, as defined in claim 1, or pharmaceutical compositions thereof as defined in claim 12 and one or more chemotherapeutic agents, as a combined preparation for simultaneous, separate or sequential use in anticancer therapy.

\* \* \* \* \*